(12) United States Patent
Spuhler et al.

(10) Patent No.: US 11,976,269 B2
(45) Date of Patent: May 7, 2024

(54) PRECISE DELIVERY OF COMPONENTS INTO FLUIDS

(71) Applicant: Cellular Research, Inc., Menlo Park, CA (US)

(72) Inventors: Philipp Spuhler, Redwood City, CA (US); Sixing Li, Mountain View, CA (US); Dennis Prosen, Foster City, CA (US)

(73) Assignee: CELLULAR RESEARCH, INC., Menlo Park, CA (US)

( * ) Notice: Subject to any disclaimer, the term of this patent is extended or adjusted under 35 U.S.C. 154(b) by 177 days.

(21) Appl. No.: 16/799,464

(22) Filed: Feb. 24, 2020

(65) Prior Publication Data
US 2020/0299672 A1 Sep. 24, 2020

Related U.S. Application Data

(60) Provisional application No. 62/820,259, filed on Mar. 18, 2019.

(51) Int. Cl.
| | | |
|---|---|---|
| *C12Q 1/68* | (2018.01) | |
| *C12N 15/10* | (2006.01) | |
| *B01L 3/00* | (2006.01) | |

(52) U.S. Cl.
CPC ........ *C12N 15/1003* (2013.01); *B01L 3/5027* (2013.01)

(58) Field of Classification Search
CPC ....................................................... B01L 3/00
USPC ............................................................ 435/6
See application file for complete search history.

(56) References Cited

U.S. PATENT DOCUMENTS

| | | | | |
|---|---|---|---|---|
| 6,899,137 | B2 * | 5/2005 | Unger | C12Q 1/6832 |
| | | | | 137/833 |
| 8,831,887 | B2 * | 9/2014 | Gorfinkel | C12Q 1/686 |
| | | | | 702/19 |
| 8,852,920 | B2 * | 10/2014 | Park | B01L 3/5085 |
| | | | | 435/287.8 |
| 9,512,466 | B2 * | 12/2016 | Abbyad | B01J 19/0046 |
| 10,415,084 | B2 * | 9/2019 | Chiou | B01L 3/50851 |
| 2006/0121624 | A1 * | 6/2006 | Huang | G01N 1/38 |
| | | | | 436/180 |

(Continued)

FOREIGN PATENT DOCUMENTS

| | | | | | |
|---|---|---|---|---|---|
| JP | S6324157 A | * | 2/1988 | ............... | C12Q 1/68 |
| JP | H02284061 | * | 11/1990 | ............... | C12Q 1/68 |

(Continued)

OTHER PUBLICATIONS

Catoen, It's Time to Reevaluate Co-Injection Technology, MoldMaking Technology, available at https://www.moldmakingtechnology.com/articles/its-time-to-reevaluate-co-injection-technology, Feb. 2, 2013.*

*Primary Examiner* — Aaron A Priest
(74) *Attorney, Agent, or Firm* — Nicholas D. Cervenka; Bret E. Field; BOZICEVIC, FIELD & FRANCIS LLP

(57) ABSTRACT

Disclosed herein include systems, apparatuses, devices, and methods for introducing one or more components into a fluid. A first fluid and a second fluid can be co-injected into a fluidic channel of a flow cell. In some embodiments, the first fluid and a second fluid are immiscible (e.g. an aqueous buffer and a non-aqueous liquid). In some embodiments, the second fluid is less dense than the first fluid.

22 Claims, 13 Drawing Sheets

(56) References Cited

U.S. PATENT DOCUMENTS

| | | | |
|---|---|---|---|
| 2008/0124726 A1* | 5/2008 | Monforte | G01N 33/56966 435/7.1 |
| 2008/0169184 A1* | 7/2008 | Brown | C12Q 1/686 204/164 |
| 2009/0059222 A1* | 3/2009 | Tan | B01L 3/502753 356/318 |
| 2010/0233696 A1* | 9/2010 | Joseph | B01L 3/502715 422/547 |
| 2011/0000796 A1* | 1/2011 | Situ | G01N 33/4915 204/435 |
| 2011/0053151 A1* | 3/2011 | Hansen | G06F 3/017 435/6.19 |
| 2011/0091877 A1* | 4/2011 | Murphy | B01L 7/525 435/6.1 |
| 2012/0028342 A1* | 2/2012 | Ismagilov | B01F 13/0094 435/283.1 |
| 2012/0196314 A1* | 8/2012 | Nawaz | G01N 21/05 356/338 |
| 2013/0280725 A1* | 10/2013 | Ismagilov | B01L 3/50273 435/6.12 |
| 2014/0017687 A1* | 1/2014 | Wimberger-Friedl | C12Q 1/6869 435/6.11 |
| 2014/0038193 A1* | 2/2014 | Spoto | B01L 3/5027 435/6.12 |
| 2014/0087958 A1* | 3/2014 | Chiang | C12Q 1/6876 506/9 |
| 2014/0295421 A1* | 10/2014 | Link | B01F 5/0653 435/6.11 |
| 2014/0342375 A1* | 11/2014 | Grisham | B01L 3/502753 435/7.24 |
| 2015/0140563 A1* | 5/2015 | Conoci | G01N 21/6452 29/458 |
| 2015/0225777 A1* | 8/2015 | Hindson | B01L 3/508 506/4 |
| 2015/0352547 A1* | 12/2015 | Breinlinger | B01L 3/5027 435/395 |
| 2016/0266105 A1* | 9/2016 | Ismagilov | G01N 33/54386 |
| 2016/0273032 A1* | 9/2016 | Esfandyarpour | G16B 25/00 |
| 2016/0333400 A1* | 11/2016 | Makino | B01L 3/502746 |
| 2016/0354777 A1* | 12/2016 | Chiu | B01L 3/5027 |
| 2017/0128947 A1* | 5/2017 | Liu | B01L 7/54 |
| 2017/0209864 A1* | 7/2017 | Grisham | B01L 3/502753 |
| 2018/0010179 A1* | 1/2018 | Hansen | B01L 3/505 |
| 2018/0024096 A1* | 1/2018 | Christey | C12Q 1/6853 204/451 |
| 2018/0200710 A1 | 7/2018 | Spuhler et al. | |
| 2018/0221875 A1* | 8/2018 | Glauser | C12Q 1/6806 |
| 2018/0311671 A1* | 11/2018 | Cook | B01L 3/5088 |
| 2019/0060902 A1* | 2/2019 | Handique | C12M 47/04 |
| 2020/0270674 A1* | 8/2020 | Hirase | C12Q 1/686 |
| 2020/0354777 A1* | 11/2020 | Grabmayr | C12Q 1/6816 |

FOREIGN PATENT DOCUMENTS

| | | | | |
|---|---|---|---|---|
| JP | H0643163 A | * | 2/1994 | G03G 9/09708 |
| WO | WO-2012106658 A1 | * | 8/2012 | B01F 13/0059 |
| WO | WO-2016118915 A1 | * | 7/2016 | B01L 3/502746 |
| WO | WO2016118915 A1 | | 7/2016 | |
| WO | WO2016138496 A1 | | 9/2016 | |
| WO | WO2016149639 A1 | | 9/2016 | |
| WO | WO-2018132610 A1 | * | 7/2018 | C12Q 1/6874 |
| WO | WO2018132610 A1 | | 7/2018 | |

* cited by examiner

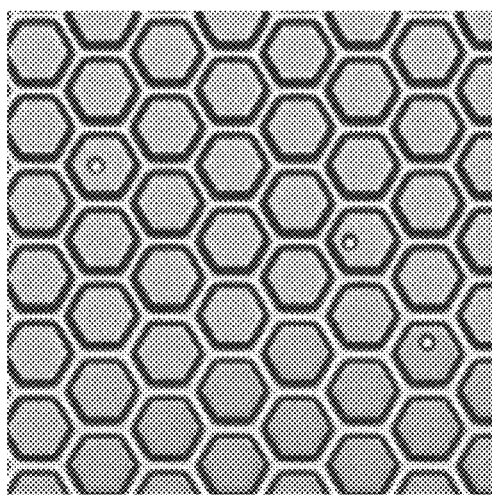
FIG. 12A1
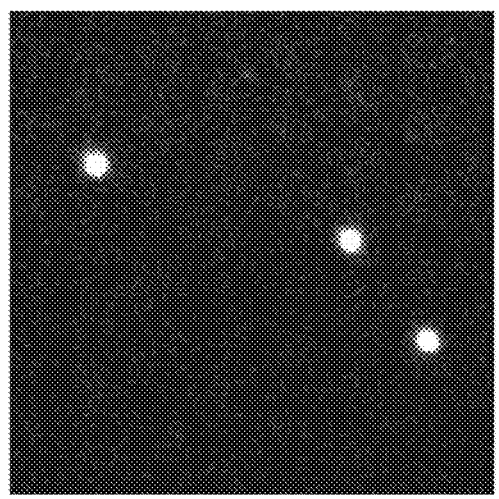
FIG. 12A2
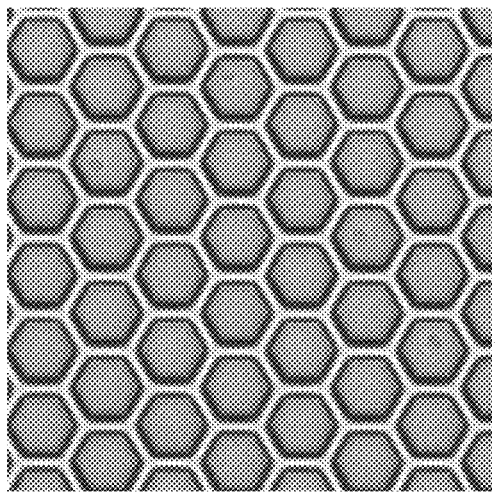
FIG. 12B1
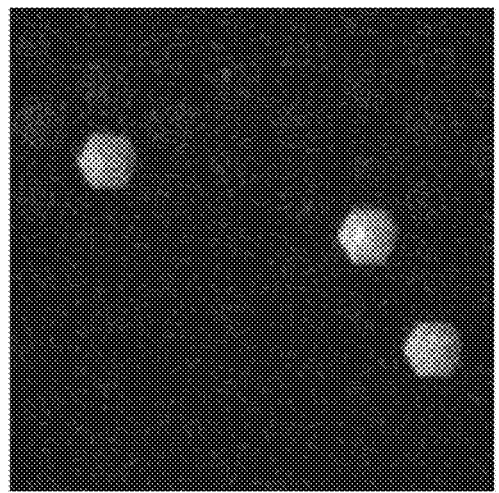
FIG. 12B2
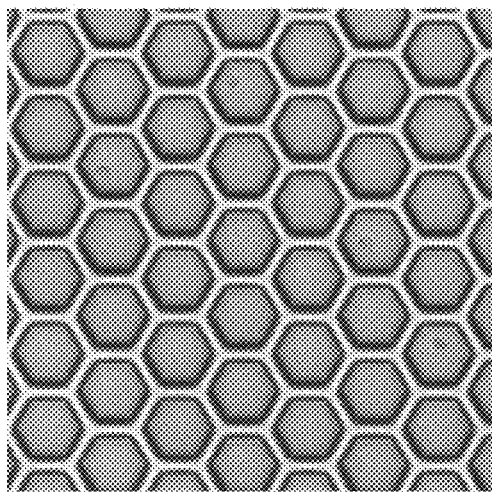
FIG. 12C1
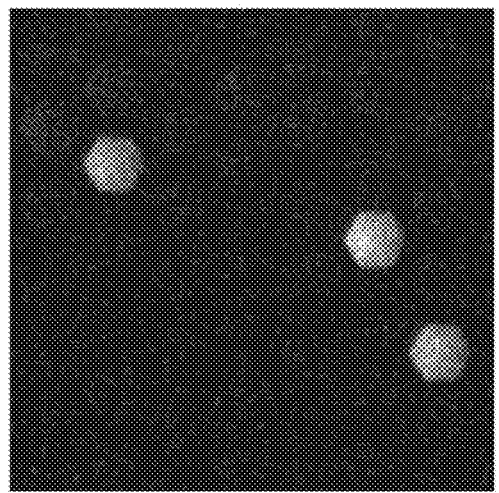
FIG. 12C2

US 11,976,269 B2

PRECISE DELIVERY OF COMPONENTS INTO FLUIDS

BACKGROUND

Field

The present disclosure relates generally to the field of molecular biology, for example determining gene expression using molecular barcoding.

Description of the Related Art

Current technology allows measurement of gene expression of single cells in a massively parallel manner (e.g., >10000 cells) by attaching cell specific oligonucleotide barcodes to poly(A) mRNA molecules from individual cells as each of the cells is co-localized with a barcoded reagent bead in a compartment. There is a need for systems and methods of introducing one or more components into a fluid (e.g., the fluid of a microwell comprising a single bead and a single cell).

SUMMARY

Disclosed herein include systems, apparatuses, devices, and methods for introducing one or more components to contents of microwells. In some embodiments, the method comprises: (a) introducing a first fluid into a fluidic channel comprising a ceiling, a first sidewall, and a bottom, wherein the bottom of the fluidic channel comprises a plurality of microwells, and wherein the ceiling, the first sidewall, and the bottom of the fluidic channel surround a fluidic channel volume of the fluidic channel excluding the volume of each of the plurality of microwells (e.g., above the microwells), whereby the fluidic channel volume and each microwell of the plurality of microwells comprise the first fluid; (b) introducing a first displacement fluid into the fluidic channel to displace the first fluid from the fluidic channel volume at a first flow rate; (c) introducing a second fluid, immediately followed by and/or simultaneously with, a second displacement fluid, into the fluidic channel at a second flow rate, wherein one or more components of the second fluid enters the content in the microwell when the second fluid comes into contact with the content in the microwell for a first duration, and wherein the second displacement fluid displaces the second fluid from the fluidic channel volume and/or seals the content of the microwell. In some embodiments, the method comprises (c) introducing a third fluid, immediately followed by and/or simultaneously with a third displacement fluid, into the fluidic channel at a third flow rate, wherein one or more components of the third fluid enters the content in the microwell when the third fluid comes into contact with the content in the microwell for a second duration, and wherein the third displacement fluid displaces the third fluid from the fluidic channel volume and/or seals the content of the microwell.

Disclosed herein include methods for introducing one or more components. In some embodiments, the method comprises: (a) introducing a first fluid into a fluidic channel comprising a ceiling, a first sidewall, and a bottom, wherein the bottom of the fluidic channel comprises a plurality of microwells, and wherein the ceiling, the first sidewall, and the bottom of the fluidic channel surround a fluidic channel volume of the fluidic channel excluding the volume of each of the plurality of microwells (e.g., above the microwells), whereby the fluidic channel volume and each microwell of the plurality of microwells comprise the first fluid; (b) introducing a first displacement fluid into the fluidic channel to displace the first fluid from the fluidic channel volume; (d) introducing a plurality of second fluids, each immediately followed by and/or simultaneously with a second displacement fluid, into the fluidic channel at a second flow rate, wherein one or more components of each of the plurality of second fluids enters the content in the microwell when the second fluid comes into contact with the content in the microwell for a first duration, and wherein the second displacement fluid displaces the second fluid from the fluidic channel volume and/or seals the content of the microwell.

Disclosed herein include methods for introducing one or more components. In some embodiments, the method comprises: (a) providing a fluidic channel comprising a ceiling, a first sidewall, and a bottom, wherein the bottom of the fluidic channel comprises a plurality of microwells comprising a first fluid, wherein the ceiling, the first sidewall, and the bottom of the fluidic channel surround a fluidic channel volume of the fluidic channel excluding the volume of each of the plurality of microwells (above the microwells), and wherein the fluidic channel volume lacks the first fluid; (b) introducing a plurality of second fluids, each immediately followed by and/or simultaneously with a second displacement fluid, into the fluidic channel at a second flow rate, wherein one or more components of each of the plurality of second fluids enters the content in the microwell when the second fluid comes into contact with the content in the microwell for a first duration, and wherein the second displacement fluid displaces the second fluid from the fluidic channel volume and/or seals the content of the microwell.

In some embodiments, providing the fluidic channel comprises: introducing the first fluid into the fluidic channel, whereby the fluidic channel volume and each microwell of the plurality of microwells comprise the first fluid; and (b) introducing a first displacement fluid into the fluidic channel to displace the first fluid from the fluidic channel volume. In some embodiments, the method comprises introducing a third displacement fluid immediately prior to introducing a second fluid of the plurality of second fluids. In some embodiments, the method comprises introducing a third displacement fluid immediately after introducing the second displacement fluid. In some embodiments, the method comprises introducing a third displacement fluid immediately prior to introducing the second displacement fluid. In some embodiments, the method comprises introducing a third fluid immediately prior to introducing a second fluid of the plurality of second fluids. In some embodiments, the method comprises introducing a third fluid immediately after introducing the second displacement fluid. In some embodiments, the method comprises introducing a third fluid immediately prior to introducing the second displacement fluid. In some embodiments, the second fluid and/or the third fluid enters the content of the microwell by diffusion.

In some embodiments, the concentrations of the one or more components of the second fluid in the content of the microwell is related to the first duration of the contact, and/or the concentrations of the one or more components of the third fluid in the content of the microwell is related to the second duration of the contact. In some embodiments, the first duration of the contact is related to the first speed of the second fluid in the flow channel and the volume of the second fluid, and/or the second duration of the contact is related to the second speed of the third fluid in the flow channel and the volume of the third fluid. In some embodiments, the first duration of the contact depends on the first speed of the second fluid in the flow channel and the longitudinal length of the second fluid in the flow channel, and/or the second duration of the contact depends on the second speed of the third fluid in the flow channel and the longitudinal length of the third fluid in the flow channel.

In some embodiments, the longitudinal length of the second fluid in the flow channel depends on the volume of the second fluid introduced, the volume of the fluidic channel volume, the volume of the flowcell, or a combination thereof, and/or the longitudinal length of the third fluid in the flow channel depends on the volume of the third fluid introduced, the volume of the fluidic channel volume, the volume of the flowcell, or a combination thereof. In some embodiments, the first flow rate is a fixed flow rate, the second flow rate is a fixed flow rate, and/or the third flow rate is a fixed flow rate. In some embodiments, the first flow rate is a variable flow rate, the second flow rate is a variable flow rate, and/or the third flow rate is a variable flow rate. In some embodiments, the first flow rate is an increasing flow rate, the second flow rate is an increasing flow rate, and/or the third flow rate is an increasing flow rate. In some embodiments, the first flow rate is a decreasing flow rate, the second flow rate is a decreasing flow rate, and/or the third flow rate is a decreasing flow rate. In some embodiments, introducing the first fluid and/or the first displacement fluid comprises co-injecting the first fluid immediately followed by and/or simultaneously with the first displacement fluid at the first flow rate.

In some embodiments, introducing the first fluid and/or the first displacement fluid comprises introducing the first fluid and/or the first displacement fluid using a pump. In some embodiments, introducing the second fluid, immediately followed by and/or simultaneously with the second displacement fluid, into the fluidic channel comprises co-injecting the second fluid followed by the second displacement fluid. In some embodiments, introducing the second fluid, immediately followed by and/or simultaneously with the third displacement fluid, comprises introducing the third fluid, immediately followed by and/or simultaneously with the third fluid using a pump. In some embodiments, introducing the third fluid, immediately followed by and/or simultaneously with the third displacement fluid, into the fluidic channel comprises co-injecting the third fluid followed by the third displacement fluid. In some embodiments, introducing the third fluid, immediately followed by and/or simultaneously with the third displacement fluid, comprises introducing the third fluid, immediately followed by and/or simultaneously with the third fluid using a pump.

In some embodiments, the first fluid and/or the first displacement fluid are introduced into the fluidic channel via non-laminar flow, the second fluid and/or the second displacement fluid are introduced into the fluidic channel via non-laminar flow, and/or the third fluid and/or the third displacement fluid are introduced into the fluidic channel via non-laminar flow. In some embodiments, the fluidic channel is configured for introducing the first fluid, the first displacement fluid, the second fluid, the second displacement fluid, the third fluid, and/or the third displacement fluid via non-laminar flow. In some embodiments, the non-laminar flow is plug flow or is approximately plug flow.

In some embodiments, the first fluid is introduced into the fluidic channel via a first opening of a flowcell comprising the fluidic channel, and the first fluid is displaced from the fluidic channel volume via a second opening of the flowcell. In some embodiments, the second fluid is introduced into the fluidic channel via a first opening of a flowcell comprising the fluidic channel, and the second fluid is displaced from the fluidic channel volume via a second opening of the flowcell. In some embodiments, the third fluid is introduced into the fluidic channel via a first opening of a flowcell comprising the fluidic channel, and the third fluid is displaced from the fluidic channel volume via a second opening of the flowcell. In some embodiments, the third fluid is introduced into the fluidic channel via a second opening of a flowcell comprising the fluidic channel, and the third fluid is displaced from the fluidic channel volume via a first opening of the flowcell. In some embodiments, the third fluid is introduced into the fluidic channel via a third opening of a flowcell comprising the fluidic channel, and the third fluid is displaced from the fluidic channel volume via a fourth opening of the flowcell.

In some embodiments, the method comprises re-orienting the direction of the fluidic channel relative to the bottom of the fluidic channel prior to introducing the third fluid. In some embodiments, the method comprises re-orienting the direction of the fluidic channel relative to the bottom of the fluidic channel by 80, 180, or 270 degrees. In some embodiments, the microwell, after introducing the first displacement fluid, comprises a single cell, a particle, or a combination thereof. In some embodiments, the first fluid comprises an aqueous liquid, a plurality of single cells, a plurality of particles, or a combination thereof. In some embodiments, the aqueous liquid comprises a priming liquid. In some embodiments, the first displacement fluid, the second displacement fluid comprise, and/or the third displacement fluid comprises a gas, a non-aqueous liquid, or a combination thereof. In some embodiments, the second fluid and/or the third fluid comprises an aqueous liquid. In some embodiments, the first content liquid, the second content liquid, and/or the third content liquid comprises a non-aqueous liquid. In some embodiments, the first displacement liquid, the second displacement liquid, and/or the third displacement liquid comprises a gas, an aqueous liquid, or a combination thereof.

In some embodiments, the density of the first content liquid is higher than the density of the second content liquid, wherein the density of the second content liquid is higher than the density of the third content liquid, and/or wherein the density of the first content liquid is higher than the density of the third content liquid. In some embodiments, the density of the first content liquid is higher than the density of the first displacement liquid, the density of the second displacement liquid, and/or the density of the third displacement liquid. In some embodiments, the density of the second content liquid is higher than the density of the first displacement liquid, the density of the second displacement liquid, and/or the density of the third displacement liquid. In some embodiments, the density of the third content liquid is higher than the density of the first displacement liquid, the density of the second displacement liquid, and/or the density of the third displacement liquid. In some embodiments, the density of the first content liquid is lower than the density of the first displacement liquid, the density of the second displacement liquid, and/or the density of the third displacement liquid. In some embodiments, the density of the second content liquid is lower than the density of the first displacement liquid, the density of the second displacement liquid, and/or the density of the third displacement liquid. In some embodiments, the density of the third content liquid is lower than the density of the first displacement liquid, the density of the second displacement liquid, and/or the density of the third displacement liquid.

In some embodiments, the first displacement fluid, the second displacement fluid, and/or the third displacement fluid are different. In some embodiments, the first displacement fluid, the second displacement fluid, and/or the third displacement fluid are different types. In some embodiments, the first displacement fluid, the second displacement fluid, and/or the third displacement fluid are identical. In some embodiments, the first displacement fluid, the second displacement fluid, and/or the third displacement fluid are of the same type. In some embodiments, the first fluid, the second fluid, and/or the third fluid are different. In some embodiments, the first fluid, the second fluid, and/or the third fluid are different types. In some embodiments, the first fluid, the second fluid, and/or the third fluid are identical. In some embodiments, the first fluid, the second fluid, and/or the third fluid are of the same type.

In some embodiments, the first fluid, the second fluid, and/or the third fluid comprise an analyte, a buffer component, a small molecule, a biomolecule, a reagent, an agent, or a combination thereof. In some embodiments, the first fluid, the second fluid, and/or the third fluid comprise a lysis buffer. In some embodiments, upon exposure to the lysis buffer, the content of the cell is released into the microwell. In some embodiments, target molecules associated with the cell hybridize to target binding regions of barcodes associated with the particle. In some embodiments, the method comprises performing a reaction. In some embodiments, the reaction comprises a reverse transcription reaction, a nucleic acid extension reaction, polymerase chain reaction, and/or a combination thereof. In some embodiments, the first fluid is a first plug and the second fluid is a second plug.

Disclosed herein include methods for introducing one or more components into a fluid. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; (b) priming the flowcell with a priming fluid; (c) displacing the priming fluid from the volume of the fluidic channel above the plurality microwells, whereby the content of each microwell of plurality of microwells comprises the priming fluid; and (d) co-injecting a first fluid and a second fluid into the fluidic channel, wherein the first fluid is introduced into the fluidic channel immediately before the second fluid, wherein one or more components of the first fluid enters the content of the microwell, and wherein the second fluid seals the content of the microwell.

In some embodiments, the first fluid interfaces with a surface of the content of the microwell for a duration. In some embodiments, the one or more components of the first fluid enter the microwell by diffusion. In some embodiments, during the duration when the first fluid interfaces with the surface of the microwell, the one or more components initiates a reaction in the content of the microwell. In some embodiments, after the first fluid interfaces with the surface of the microwell, the one or more components initiates a reaction in the content of the microwell.

Disclosed herein include methods of performing a reaction. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; and (b) co-injecting a first fluid and a second fluid into the fluidic channel, wherein the first fluid is introduced into the fluidic channel immediately before the second fluid, wherein the first fluid interfaces with a surface of a microwell for a duration, wherein one or more components of the first fluid enters the content of the microwell, wherein the one or more components initiates a reaction in the content of the microwell, and wherein the second fluid seals the content of the microwell.

Disclosed herein include methods of delivering varying concentrations of an analyte to a plurality of microwells. In some embodiments, the method comprises: (a) providing a flowcell comprising a fluidic channel, wherein the fluidic channel comprises a ceiling, a first sidewall, and a bottom, wherein the bottom comprises a substrate which comprises a plurality of microwells; and (b) co-injecting a first fluid and a second fluid into the fluidic channel, wherein the first fluid is introduced into the fluidic channel immediately before the second fluid, wherein the first fluid interfaces with a surface of the content of the microwell for a duration, wherein the first fluid comprises one or more components, wherein the one or more components of the first fluid comprise an analyte, wherein the flow rate of the first fluid is not uniform along the longitudinal path of the fluidic channel, wherein the analyte enters the content of the microwell, wherein the final concentration of the analyte in the microwell is unequal for at least two microwells of the plurality of microwells, and wherein the second fluid seals the content of the microwell.

In some embodiments, the first fluid is a first plug and the second fluid is a second plug. In some embodiments, during the duration when the first fluid interfaces with the surface of the microwell, the one or more components initiates a reaction in the content of the microwell. In some embodiments, the method comprises, prior to the co-injecting, priming the flowcell with a priming fluid. In some embodiments, the method comprises, prior to the co-injecting, displacing the priming fluid from the volume of the fluidic channel above the plurality microwells. In some embodiments, the volume of the first fluid is at most 10% the volume of the second fluid. In some embodiments, following the co-injecting, the volume of the fluidic channel above the plurality microwells comprises the second fluid. In some embodiments, following the co-injecting, the volume of the fluidic channel above the plurality microwells does not comprise the first fluid. In some embodiments, displacing the priming fluid from the volume of the fluidic channel above the plurality microwells comprises injection of a displacing fluid into the fluidic channel. In some embodiments, the displacing fluid is a gas. In some embodiments, the displacing fluid is a non-aqueous liquid. In some embodiments, the priming fluid is a first aqueous liquid. In some embodiments, the priming fluid is a first non-aqueous liquid. In some embodiments, the microwell comprises an initial microwell fluid prior to the co-injecting. In some embodiments, the initial microwell fluid comprises the priming fluid. In some embodiments, the initial microwell fluid is an aqueous liquid. In some embodiments, the initial microwell fluid is an aqueous buffer. In some embodiments, the initial microwell fluid is a non-aqueous liquid.

In some embodiments, the one or more components of the first fluid comprise an analyte. In some embodiments, the first fluid comprises a known concentration of an analyte. In some embodiments, the first fluid comprises an unknown concentration of an analyte. In some embodiments, the one or more components of the first fluid comprise an analyte, a buffer component, a small molecule, a biomolecule, a reagent, an agent, or any combination thereof. In some embodiments, the flow rate of the first fluid is equal to the flow rate of the second fluid. In some embodiments, the first fluid and the second fluid are immiscible.

In some embodiments, the density of the first fluid is greater than the density of the second fluid. In some embodiments, the density of the first fluid is greater than the density of the second fluid, and wherein the first fluid and the second fluid are immiscible. In some embodiments, the first fluid comprises a second aqueous liquid and the second fluid comprises a first non-aqueous fluid. In some embodiments, the first fluid comprises a second aqueous liquid and the second fluid comprises a gas. In some embodiments, the first fluid comprises a second non-aqueous liquid and the second fluid comprises a second aqueous liquid.

In some embodiments, the second fluid has the same composition as the displacing fluid. In some embodiments, the second fluid has a different composition than the displacing fluid. In some embodiments, the first fluid has a different composition than the displacing fluid. In some embodiments, the diffusion of one or more components of the first fluid into the microwell produces a first admixture of the first fluid and the initial microwell liquid. In some embodiments, one or more components of the first fluid are present at a lower concentration in the initial microwell liquid. In some embodiments, one or more components of the first fluid are absent in the initial microwell liquid. In some embodiments, the concentration of the one or more components of the first fluid within the first admixture comprises is at least 2-fold higher than the concentration of the one or more components of the first fluid in the initial microwell liquid.

In some embodiments, the duration is less than the reaction duration. In some embodiments, the reaction initiates after the duration has occurred. In some embodiments, the reaction initiates after the second fluid seals the content of the microwell. In some embodiments, the duration is short enough that one or more components of the microwell do not diffuse out of the microwell. In some embodiments, the one or more components of the microwell comprises a cell, a bead, a biomolecule, a buffer component, a small molecule, a biomolecule, a reagent, an agent, or any combination thereof. In some embodiments, the reaction duration is between about 1 second and about 3 hours. In some embodiments, the duration is dynamically controlled. In some embodiments, the duration is a function of the volume of the first fluid, the flow rate of the first fluid, the flowcell dimensions, or any combination thereof. In some embodiments, the duration is a dynamically controlled by adjusting the volume of the first fluid, the flow rate of the first fluid, or any combination thereof.

In some embodiments, the final concentration of the one or more components of the first fluid in the microwell following the duration is a function of the duration and/or flowcell dimensions. In some embodiments, the flow rate of the first fluid is uniform along the longitudinal path of the fluidic channel. In some embodiments, the flow rate of the first fluid is not uniform along the longitudinal path of the fluidic channel. In some embodiments, the flow rate of the first fluid changes along the longitudinal path of the fluidic channel. In some embodiments, the flow rate of the first fluid increases along the longitudinal path of the fluidic channel. In some embodiments, the flow rate of the first fluid decreases along the longitudinal path of the fluidic channel. In some embodiments, the change in the flow rate of the first fluid is linear. In some embodiments, the change in the flow rate of the first fluid is non-linear. In some embodiments, the change in the flow rate of the first fluid is exponential. In some embodiments, the change in the flow rate of the first fluid is logarithmic.

In some embodiments, the flow rate of the first fluid is higher at an anterior position along the longitudinal path of the fluidic channel relative a posterior position along the longitudinal path of the fluidic channel. In some embodiments, the flow rate of the first fluid is lower at an anterior position along the longitudinal path of the fluidic channel relative a posterior position along the longitudinal path of the fluidic channel. In some embodiments, the difference between the flow rate of the first fluid at the anterior position relative the posterior position is, is about, is at most about, or is at least about 1.1-fold. In some embodiments, the final concentration of the one or more components of the first fluid in the contents of the plurality of microwells following the co-injecting is uniform. In some embodiments, the coefficient of variation for the final concentration of the one or more components of the first fluid in the contents of the plurality of microwells following the co-injecting is less than 5%. In some embodiments, the final concentration of the one or more components of the first fluid in the contents of the plurality of microwells following the serial the co-injecting is non-uniform. In some embodiments, the final concentration of the one or more components of the first fluid in the content of each microwell changes along the longitudinal path of the fluidic channel. In some embodiments, the change in the final concentration of the one or more components of the first fluid in the content of each microwell is linear. In some embodiments, the change in the final concentration of the one or more components of the first fluid in the content of each microwell is non-linear. In some embodiments, the change in the final concentration of the one or more components of the first fluid in the content of each microwell is exponential. In some embodiments, the change in the final concentration of the one or more components of the first fluid in the content of each microwell is logarithmic.

In some embodiments, the difference between the final concentration of the one or more components of the first fluid in the content of a microwell at an anterior position along the longitudinal path of the fluidic channel relative a posterior position along the longitudinal path of the fluidic channel is, is about, is at most about, or is at least about 1.1-fold. In some embodiments, the final concentration of the one or more components of the first fluid in the content of each microwell increases along the longitudinal path of the fluidic channel. In some embodiments, final concentration of the one or more components of the first fluid in the content of each microwell decreases along the longitudinal path of the fluidic channel.

In some embodiments, the flowcell dimensions are uniform across the plurality of microwells. In some embodiments, the flowcell dimensions are not uniform across the plurality of microwells. In some embodiments, the flowcell dimensions comprise the volume of the microwell and/or the surface area of the microwell interfacing the volume of the fluidic channel above the plurality microwells. In some embodiments, the difference between the volume of a microwell at an anterior position along the longitudinal path of the fluidic channel relative a posterior position along the longitudinal path of the fluidic channel is, is about, is at most about, or is at least about 1.1-fold. In some embodiments, the difference between the surface area of a microwell interfacing the volume of the fluidic channel above the plurality microwells at an anterior position along the longitudinal path of the fluidic channel relative a posterior position along the longitudinal path of the fluidic channel is, is about, is at most about, or is at least about 1.1-fold.

In some embodiments, a speed of the flow at a boundary between the flow and the bottom is non-zero. In some embodiments, the relative flow velocity of a flow across a cross-section of the fluidic channel is approximately constant. In some embodiments, the flow is plug flow. In some embodiments, the ceiling comprises a hydrophilic coating, wherein the hydrophilic coating comprises polyethylene glycol (PEG), poly-Hema, pluronic acid F68, pluronic acid F108, pluronic acid F127, polysorbate 20, silicon dioxide ($SiO_2$), silicon nitride, or any combination thereof. In some embodiments, the angle of the ceiling is sufficiently smaller than the contact angle of the first sidewall.

In some embodiments, the second fluid sealing the content of the microwell reduces cross-talk. In some embodiments, the second fluid sealing the content of the microwell reduces cross-talk by, by about, by at most about, or at least about 5% as compared to comparable flowcell methods performed using a single fluid injection. In some embodiments, the cross-talk comprises the diffusion of nucleic acids, proteins, antibodies, biomolecules, or any combination thereof, from one microwell to another microwell. In some embodiments, the cross-talk comprises the diffusion of nucleic acids, proteins, antibodies, biomolecules, or any combination thereof, from the microwell to the volume of the fluidic channel above the plurality microwells.

In some embodiments, the substrate comprises a microwell array, wherein the microwell array comprises at least 100 microwells, wherein each microwell has a volume ranging from about 1,000 $\mu m^3$ to about 786,000 $\mu m^3$. In some embodiments, the reduced cross-talk enables use of a higher density microwell array without a concomitant increase in cross-talk. In some embodiments, the higher density microwell array comprises at least 100 more microwells per $inch^2$ as compared to a standard microwell array. In some embodiments, the use of the higher density microwell array increases cell loading efficiency as compared to a standard microwell array. In some embodiments, the use of the higher density microwell array increases bead loading efficiency as compared to a standard microwell array. The use of the higher density microwell array can decrease the number doublet events as compared to a standard microwell array.

In some embodiments, the method comprises, prior to the co-injecting, capturing single cells in the plurality of microwells. In some embodiments, the method comprises, prior to the co-injecting, capturing single cells and single beads in the plurality of microwells, wherein a single bead comprises a plurality of tethered barcodes, and wherein the plurality of tethered barcode further comprises: i) a bead-specific cellular label; ii) a diverse set of molecular labels; and iii) a plurality of target binding regions capable of hybridizing with nucleic acid molecules. In some embodiments, the reaction comprises cell lysis. In some embodiments, the first fluid comprises a lysis buffer. In some embodiments, the duration is a length of time sufficient to deliver an amount of lysis buffer to the microwell sufficient to lyse the cell. In some embodiments, the second fluid sealing the content of the microwell yields an increase in the number of mRNAs and/or cellular component-binding reagent oligonucleotides captured by barcodes as compared to comparable flowcell methods performed using a single fluid injection. In some embodiments, the second fluid sealing the content of the microwell yields an increase in the number of occurrences of unique molecular labels associated with each of the mRNAs and/or cellular component-binding reagent oligonucleotides determined as compared to comparable flowcell methods performed using a single fluid injection. In some embodiments, the second fluid sealing the content of the microwell yields an increase in the signal-to-noise ratio as compared to comparable flowcell methods performed using a single fluid injection.

In some embodiments, the flow rate of the first fluid is gradually decreased as it traverses the fluidic channel, wherein the final concentration of the one or more components of the first fluid in each microwell is uniform across the plurality of microwells. In some embodiments, one or more components of the first fluid entering the content of the microwell terminates a reaction. In some embodiments, the method comprises a second co-injecting of fluids into the fluidic channel. In some embodiments, the second co-injecting of fluids comprises co-injecting a first fluid of a second co-injection and a second fluid of a second co-injection into the fluidic channel, wherein the first fluid of the second co-injection is introduced into the fluidic channel immediately before the second fluid of a second co-injection, and wherein the second fluid of the second co-injection seals the content of the microwell. In some embodiments, the first fluid of the second co-injection and the second fluid of the second co-injection are immiscible. In some embodiments, the density of the first fluid of the second co-injection is greater than the density of the second fluid of the second co-injection. In some embodiments, the density of the first fluid of the second co-injection is greater than the density of the second fluid of the second co-injection, and wherein the first fluid of the second co-injection and the second fluid of the second co-injection are immiscible.

In some embodiments, the second co-injecting is performed in the reverse direction relative to the first co-injecting. In some embodiments, the first fluid of the second co-injection comprises an aqueous liquid and the second fluid of the second co-injection comprises a non-aqueous liquid. In some embodiments, the first fluid of the second co-injection comprises an aqueous liquid and the second fluid of the second co-injection comprises a gas. In some embodiments, the first fluid of the second co-injection comprises a non-aqueous liquid and the second fluid of the second co-injection comprises an aqueous liquid. In some embodiments, the first fluid of the first co-injection and the first fluid of the second co-injection are the same. In some embodiments, the first fluid of the first co-injection and the first fluid of the second co-injection are different. In some embodiments, the second fluid of the first co-injection and the second fluid of the second co-injection are the same. In some embodiments, the second fluid of the first co-injection and the second fluid of the second co-injection are different. In some embodiments, the method does not comprise the use of buffer additives to reduce cross-talk. In some embodiments, the buffer additives adjust the viscosity of fluids and/or reagents. In some embodiments, the buffer additives comprise sucrose, polyethylene glycol (PEG), Ficoll, glycerin, glycerol, dextran sulfate, histopaque, bovine serum albumin, or any combination thereof.

In some embodiments, a device is provided comprising the flowcell comprises at least one inlet port and at least one outlet port, wherein the at least one inlet port and at least one outlet port are capable of directing a flow of a fluid through the flow cell, thereby contacting the microwells with the fluid. In some embodiments, a device comprising the flowcell is a removable, consumable component of an instrument system configured to perform automated, barcoding assays on a plurality of single cells.

Disclosed herein include methods for determining the number of occurrences of a target nucleic acid molecule in single cells. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; (b)

capturing single cells and single beads in the plurality of microwells, wherein a single bead comprises a plurality of tethered barcodes, and wherein the plurality of tethered barcodes further comprises: i) a bead-specific cellular label; ii) a diverse set of molecular labels; and iii) a plurality of target binding regions capable of hybridizing with target nucleic acid molecules; (c) co-injecting a first fluid and a second fluid into the fluidic channel, wherein the first fluid is introduced into the fluidic channel immediately before the second fluid, wherein the first fluid interfaces with a surface of the content of the microwell for a duration, wherein the first fluid comprises a lysis buffer, wherein one or more components of the first fluid enter the microwell by diffusion and initiate cellular lysis, and wherein the second fluid seals the content of the microwell; (d) hybridizing target nucleic acid molecules released from single cells following cellular lysis with the plurality of target binding regions tethered to single beads in a stochastic manner; (e) performing an extension reaction to create a plurality of molecular conjugates each comprising a barcode and a portion of a complementary sequence of one of the target nucleic acid molecule; (f) amplifying and sequencing the molecular conjugates; and (g) determining the number of occurrences of the target nucleic acid molecule in the single cells. In some embodiments, the density of the first fluid is greater than the density of the second fluid, and wherein the first fluid and the second fluid are immiscible. In some embodiments, step (b) comprises priming the flow cell, loading the cells, and then loading the beads. In some embodiments, step (b) comprises priming the flow cell, displacing the priming buffer with an air injection, loading a cell suspension, displacing the cell suspension with an air injection, and loading the beads. In some embodiments, the plurality of tethered barcodes further comprise a universal primer sequence. In some embodiments, the plurality of target binding regions of the plurality of barcodes tethered to a bead comprise a mixture of sequences selected from the group consisting of gene-specific sequences, oligo-dT sequences, random multimer sequences, or any combination thereof.

In some embodiments, the target nucleic acid molecules comprise RNA molecules. In some embodiments, the target nucleic acid molecules comprise mRNA molecules. In some embodiments, the target nucleic acid molecules comprise cellular component-binding reagent oligonucleotides. In some embodiments, the cellular component-binding reagent oligonucleotides comprise sample indexing oligonucleotides. In some embodiments, the target nucleic acid molecules comprises cellular component-binding reagent oligonucleotides, and wherein determining the number of occurrences of the target nucleic acid molecule in the single cells indicates the number of copies of a cellular component target in the single cell. In some embodiments, the target nucleic acid molecules comprise sample indexing oligonucleotides, and wherein determining the number of occurrences of the target nucleic acid molecule in the single cells indicates identifies the sample origin of the cell. In some embodiments, the second fluid sealing the content of the microwell yields an increase in the number of mRNAs and/or cellular component-binding reagent oligonucleotides captured by the barcodes as compared to comparable flowcell methods performed using a single fluid injection. In some embodiments, the second fluid sealing the content of the microwell yields an increase in the number of occurrences of unique molecular labels associated with each of the mRNAs and/or cellular component-binding reagent oligonucleotides determined as compared to comparable flowcell methods performed using a single fluid injection. In some embodiments, the second fluid sealing the content of the microwell yields an increase in the signal-to-noise ratio as compared to comparable flowcell methods performed using a single fluid injection. In some embodiments, the first fluid is a first plug and the second fluid is a second plug.

Disclosed herein include methods of measuring the dose-dependent phenotypic effects of an agent on single cells. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; (b) capturing single cells in the plurality of microwells; (c) co-injecting a first fluid and a second fluid into the fluidic channel, wherein the first fluid is introduced into the fluidic channel immediately before the second fluid, wherein the first fluid interfaces with a surface of the content of the microwell for a duration, wherein the first fluid comprises one or more components, wherein the one or more components of the first fluid comprise an agent, wherein the flow rate of the first fluid is not uniform along the longitudinal path of the fluidic channel, wherein the agent enters the microwell by diffusion during the duration, wherein the final concentration of the agent in the content of the microwell is unequal for at least two microwells of the plurality of microwells, and wherein the second fluid seals the content of the microwell; and (d) measuring one or more phenotypic effects dependent on the final concentration of the agent in the microwell.

In some embodiments, the density of the first fluid is greater than the density of the second fluid, and wherein the first fluid and the second fluid are immiscible. In some embodiments, the method comprises a second co-injecting of fluids, wherein the second co-injecting comprises co-injecting a second first liquid of a second co-injection and a second liquid of a second co-injection into the fluidic channel, wherein the first liquid of the second co-injection is introduced into the fluidic channel immediately before the second liquid of the second co-injection, wherein the second liquid of the second co-injection seals the content of the microwell. In some embodiments, the density of the first liquid of the second co-injection is greater than the density of second liquid of the second co-injection, and wherein the first liquid of the second co-injection and the second liquid of the second co-injection are immiscible. In some embodiments, the second co-injecting is performed in the reverse direction relative to the first co-injecting. In some embodiments, the first fluid of the second co-injection comprises a second agent. In some embodiments, the first fluid is a first plug and the second fluid is a second plug.

In some embodiments, the flow rate of the first fluid is higher at an anterior position along the longitudinal path of the fluidic channel relative a posterior position along the longitudinal path of the fluidic channel. In some embodiments, the flow rate of the first fluid is lower at an anterior position along the longitudinal path of the fluidic channel relative a posterior position along the longitudinal path of the fluidic channel. In some embodiments, the difference between the flow rate of the first fluid at an anterior position along the longitudinal path of the fluidic channel relative a posterior position along the longitudinal path of the fluidic channel is, is about, is at most about, or is at least about 1.1-fold. In some embodiments, the final concentration of the agent in the contents of the plurality of microwells following the serial the co-injecting is non-uniform. In some embodiments, the final concentration of the agent in the content of each microwell changes along the longitudinal path of the fluidic channel. In some embodiments, the change in the final concentration of the agent in the content of each microwell is linear. In some embodiments, the change in the final concentration of the agent in the content of each microwell is non-linear. In some embodiments, the change in the final concentration of the agent in the content of each microwell is exponential. In some embodiments, the change in the final concentration of the agent in the content of each microwell is logarithmic. In some embodiments, the difference between the final concentration of the agent in the content of a microwell at an anterior position along the longitudinal path of the fluidic channel relative a posterior position along the longitudinal path of the fluidic channel is, is about, is at most about, or is at least about 1.1-fold.

In some embodiments, the agent comprises one or more components. In some embodiments, the second agent comprises one or more components. In some embodiments, the agent comprises one or more of a chemical agent, a pharmaceutical, small molecule, a biologic, a CRISPR single-guide RNA (sgRNA), a small interfering RNA (siRNA), CRISPR RNA (crRNA), a small hairpin RNA (shRNA), a microRNA (miRNA), a piwi-interacting RNA (piRNA), an antisense oligonucleotide, a peptide or peptidomimetic inhibitor, an aptamer, an antibody, an intrabody, or any combination thereof. In some embodiments, the agent comprises one or more of an epigenetic modifying agent, epigenetic enzyme, a bicyclic peptide, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis inhibitor, a nuclease, a protein fragment or domain, a tag or marker, an antigen, an antibody or antibody fragment, a ligand or a receptor, a synthetic or analog peptide from a naturally-bioactive peptide, an anti-microbial peptide, a pore-forming peptide, a targeting or cytotoxic peptide, a degradation or self-destruction peptide, a CRISPR component system or component thereof, DNA, RNA, artificial nucleic acids, a nanoparticle, an oligonucleotide aptamer, a peptide aptamer, or any combination thereof. In some embodiments, the agent possesses at least one effector activity selected from the group consisting of: modulating a biological activity, binding a regulatory protein, modulating enzymatic activity, modulating substrate binding, modulating receptor activation, modulating protein stability/degradation, modulating transcript stability/degradation, and any combination thereof.

In some embodiments, the agent comprises an infectious agent. In some embodiments, the agent comprises an anti-infectious agent. In some embodiments, the agent comprises a mixture of an infectious agent and an anti-infectious agent. In some embodiments, the infectious agent comprises a virus, a bacterium, a fungus, a protozoal parasite, or any combination thereof. In some embodiments, an anti-infectious agent comprises an anti-bacterial agent, an anti-fungal agent, an anti-parasitic agent, an anti-viral agent, or any combination thereof. In some embodiments, the agent comprises a cytotoxic agent. In some embodiments, the cytotoxic agent is selected from the group consisting of a chemotherapeutic agent, a biologic agent, a toxin, a radioactive isotope, or any combination thereof. In some embodiments, the agent comprises a non-active component of a therapeutic. In some embodiments, the non-active component of a therapeutic comprises an excipient, carrier, diluent, vehicle, adjuvant, empty vector, or any combination thereof. In some embodiments, the agent comprises an expression vector, wherein the expression vector encodes one or more of the following: an mRNA, an antisense nucleic acid molecule, a RNAi molecule, a shRNA, a mature miRNA, a pre-miRNA, a pri-miRNA, an anti-miRNA, a ribozyme, any combination thereof. In some embodiments, the single cells comprise a recombinant expression vector. In some embodiments, the recombinant expression vector comprises an inducible promoter, and wherein the expression of one or more of the following are under the control of said inducible promoter: an mRNA, an antisense nucleic acid molecule, a RNAi molecule, a shRNA, a mature miRNA, a pre-miRNA, a pri-miRNA, an anti-miRNA, a ribozyme, any combination thereof. In some embodiments, the agent is a dose-dependent inducer of the inducible promoter. In some embodiments, the dose-dependent inducer comprises tetracycline, pristinamycin, macrolide, ecdysone, mifepristone, or any combination thereof. In some embodiments, the agent modulates the expression of one or more target biomarkers. In some embodiments, the agent modulates the activity of one or more target biomarkers.

In some embodiments, the method comprises capturing single beads in the plurality of microwells, wherein a single bead comprises a plurality of tethered barcodes, and wherein the plurality of tethered barcodes further comprises: i) a bead-specific cellular label; ii) a diverse set of molecular labels; and iii) a plurality of target binding regions capable of hybridizing with target nucleic acid molecules. In some embodiments, measuring one or more phenotypic effects dependent on the final concentration of the agent in the microwell comprises mRNA expression profiling, wherein mRNA expression profiling comprises quantitative analysis of a plurality of mRNA targets in a cell. In some embodiments, measuring one or more phenotypic effects dependent on the final concentration of the agent in the microwell comprises protein expression profiling, wherein protein expression profiling comprises quantitative analysis of a plurality of protein targets in a cell. In some embodiments, measuring one or more phenotypic effects dependent on the final concentration of the agent in the microwell comprises simultaneous quantitative analysis of a plurality of protein targets and a plurality of nucleic acid target molecules in a cell.

In some embodiments, the method comprises a determination of the longitudinal flowcell position of each cell within the microwell array. In some embodiments, a determination of the longitudinal flowcell position of each cell within the microwell array comprises determining the microwell of origin of each cell. In some embodiments, each microwell of the microwell array comprises an array address code. In some embodiments, the array address code comprises a nucleic acid barcode unique for each microwell in the microwell array. In some embodiments, the array address code is covalently attached to one or more inner surfaces of the microwells. In some embodiments, the covalent attachment comprises the use of one or more cleavable linkers to enable release of the array address code. In some embodiments, the one or more cleavable linkers comprise acid-labile linkers, base-labile linkers, photocleavable linkers, enzyme-cleavable linkers, or any combination thereof. In some embodiments, the array address code comprises a restriction enzyme site. In some embodiments, a subset of the barcodes attached to the bead comprise an annealing site for the array address code. In some embodiments, upon release, the array address code hybridizes with the subset of the barcodes.

In some embodiments, association of the cellular label and the array address code during sequencing identifies the microwell of origin of each cell within the microwell array. In some embodiments, each of the plurality of beads comprises a plurality of stochastic barcodes, a first group of optical labels, and a second group of optical labels. In some embodiments, each optical label in the first group of optical labels comprises a first optical moiety and each optical label in the second group of optical labels comprises a second optical moiety. In some embodiments, each of the plurality of beads is associated with an optical barcode comprising the first optical moiety and the second optical moiety, and wherein the first optical moiety and the second optical moiety are selected from a group comprising two or more spectrally-distinct optical moieties. In some embodiments, at least two beads of the plurality of beads comprise a unique optical barcode, and wherein the optical barcode of each of the plurality of beads can be detected in the flowcell to determine the location of each of the plurality of beads. In some embodiments, the method comprises detecting the optical barcode of each of the plurality of beads to determine the location of each of the plurality of beads. In some embodiments, the method comprises determining the microwell locations of the plurality of single cells based on the locations of the plurality of beads.

In some embodiments, the method comprises an estimation of the concentration of the agent at each longitudinal flowcell position. In some embodiments, the first fluid comprises a fluorescent dye, wherein the proportion of the fluorescent dye to the agent is known. In some embodiments, the method comprises optical imaging of the flow cell after the co-injecting of the first fluid and the second fluid, wherein optical imaging comprises a measurement of the fluorescent dye in each microwell, wherein the flow cell comprises a transparent window for optical imaging. In some embodiments, the measurement of fluorescent dye in each microwell enables the estimation of the concentration of the agent in each microwell. In some embodiments, the method comprises deriving an estimation of a concentration of the agent each cell was exposed to based on the determination of the microwell of origin of each cell and the estimation of the concentration of the agent at each longitudinal flowcell position. In some embodiments, the method comprises correlation analysis of the estimated concentration of the agent each cell was exposed to and the RNA and/or DNA expression profiles of said cells. In some embodiments, the correlation analysis identifies one or more of the following: candidate therapeutic agents, candidate doses of candidate therapeutic agents, and cellular targets of candidate therapeutic agents.

BRIEF DESCRIPTION OF THE DRAWINGS

FIGS. 12A1-12C2 show exemplary bright-field images (FIGS. 12A1, 12B1, and 12C1) and fluorescent images (FIGS. 12A2, 12B2, and 12C2) of microwells 1 minute (FIGS. 12A1-12A2), 7 minutes (FIGS. 12B1-12B2), and 13 minutes (FIGS. 12C1-12C12) following a co-injection of a first fluid comprising CHAPS lysis buffer and a second fluid comprising GC2 oil. Prior to the co-injection, three microwells of the array comprise a single calcein-stained cell.

DETAILED DESCRIPTION

Figure 1:
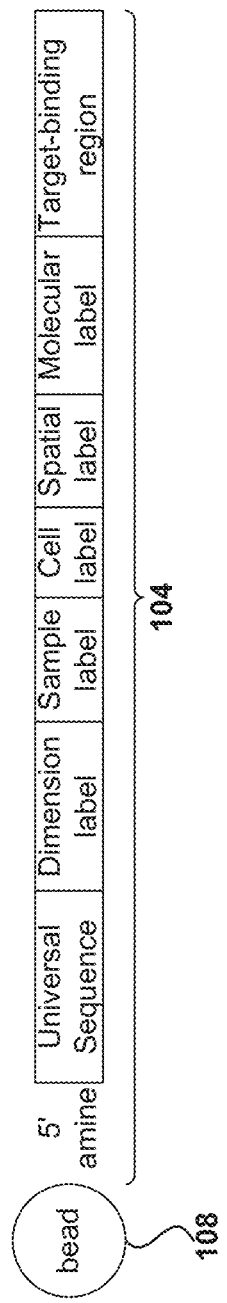
FIG. 1 illustrates a non-limiting exemplary barcode.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids, for example messenger ribonucleotide acid (mRNA) molecules, is clinically important for determining, for example, the genes that are expressed in a cell at different stages of development or under different environmental conditions. However, it can also be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements. Stochastic barcodes with unique molecular labels (also referred to as molecular indexes (MIs)) can be used to count the number of molecules and correct for amplification bias. Stochastic barcoding, such as the Precise™ assay (Cellular Research, Inc. (Palo Alto, CA)) and Rhapsody™ assay (Becton, Dickinson and Company (Franklin Lakes, NJ)), can correct for bias induced by PCR and library preparation steps by using molecular labels (MLs) to label mRNAs during reverse transcription (RT).

The Precise™ assay can utilize a non-depleting pool of stochastic barcodes with large number, for example 6561 to 65536, unique molecular label sequences on poly(T) oligonucleotides to hybridize to all poly(A)-mRNAs in a sample during the RT step. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate can be pooled into a single tube for PCR amplification and sequencing. Raw sequencing data can be analyzed to produce the number of reads, the number of stochastic barcodes with unique molecular label sequences, and the numbers of mRNA molecules.

Disclosed herein include methods for introducing one or more components. In some embodiments, the method comprises: (a) introducing a first fluid into a fluidic channel comprising a ceiling, a first sidewall, and a bottom, wherein the bottom of the fluidic channel comprises a plurality of microwells, and wherein the ceiling, the first sidewall, and the bottom of the fluidic channel surround a fluidic channel volume of the fluidic channel, whereby the fluidic channel volume and each microwell of the plurality of microwells comprise the first fluid; (b) introducing a first displacement fluid into the fluidic channel to displace the first fluid from the fluidic channel volume at a first flow rate; (c) introducing a second fluid (also referred to herein as a first fluid), immediately followed by and/or simultaneously with, a second displacement fluid (also referred to herein as a second fluid), into the fluidic channel at a second flow rate, wherein one or more components of the second fluid enters the content in the microwell when the second fluid comes into contact with the content in the microwell for a first duration, and wherein the second displacement fluid displaces the second fluid from the fluidic channel volume and/or seals the content of the microwell.

Disclosed herein include methods for introducing one or more components. In some embodiments, the method comprises: (a) introducing a first fluid into a fluidic channel comprising a ceiling, a first sidewall, and a bottom, wherein the bottom of the fluidic channel comprises a plurality of microwells, and wherein the ceiling, the first sidewall, and the bottom of the fluidic channel surround a fluidic channel volume of the fluidic channel, whereby the fluidic channel volume and each microwell of the plurality of microwells comprise the first fluid; (b) introducing a first displacement fluid into the fluidic channel to displace the first fluid from the fluidic channel volume; (c) introducing a plurality of second fluids (also referred to herein as first fluids), each immediately followed by and/or simultaneously with a second displacement fluid (also referred to herein as a second fluid), into the fluidic channel at a second flow rate, wherein one or more components of each of the plurality of second fluids enters the content in the microwell when the second fluid comes into contact with the content in the microwell for a first duration, and wherein the second displacement fluid displaces the second fluid from the fluidic channel volume and/or seals the content of the microwell.

Disclosed herein include methods for introducing one or more components. In some embodiments, the method comprises: (a) providing a fluidic channel comprising a ceiling, a first sidewall, and a bottom, wherein the bottom of the fluidic channel comprises a plurality of microwells comprising a first fluid, wherein the ceiling, the first sidewall, and the bottom of the fluidic channel surround a fluidic channel volume of the fluidic channel, and wherein the fluidic channel volume lacks the first fluid; (b) introducing a plurality of second fluids (also referred to herein as first fluids), each immediately followed by and/or simultaneously with a second displacement fluid (also referred to herein as a second fluid), into the fluidic channel at a second flow rate, wherein one or more components of each of the plurality of second fluids enters the content in the microwell when the second fluid comes into contact with the content in the microwell for a first duration, and wherein the second displacement fluid displaces the second fluid from the fluidic channel volume and/or seals the content of the microwell.

Disclosed herein include methods for introducing one or more components into a fluid. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; (b) priming the flowcell with a priming fluid; (c) displacing the priming fluid from the volume of the fluidic channel above the plurality microwells, whereby the content of each microwell of plurality of microwells comprises the priming fluid; and (d) co-injecting a first fluid and a second fluid into the fluidic channel, wherein the first fluid is introduced into the fluidic channel immediately before the second fluid, wherein one or more components of the first fluid enters the content of the microwell, and wherein the second fluid seals the content of the microwell.

Disclosed herein include methods of performing a reaction. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; and (b) co-injecting a first fluid and a second fluid into the fluidic channel, wherein the first fluid is introduced into the fluidic channel immediately before the second fluid, wherein the first fluid interfaces with a surface of a microwell for a duration, wherein one or more components of the first fluid enters the content of the microwell, wherein the one or more components initiates a reaction in the content of the microwell, and wherein the second fluid seals the content of the microwell.

Disclosed herein include methods of delivering varying concentrations of an analyte to a plurality of microwells. In some embodiments, the method comprises: (a) providing a flowcell comprising a fluidic channel, wherein the fluidic channel comprises a ceiling, a first sidewall, and a bottom, wherein the bottom comprises a substrate which comprises a plurality of microwells; and (b) co-injecting a first fluid and a second fluid into the fluidic channel, wherein the first fluid is introduced into the fluidic channel immediately before the second fluid, wherein the first fluid interfaces with a surface of the content of the microwell for a duration, wherein the first fluid comprises one or more components, wherein the one or more components of the first fluid comprise an analyte, wherein the flow rate of the first fluid is not uniform along the longitudinal path of the fluidic channel, wherein the analyte enters the content of the microwell, wherein the final concentration of the analyte in the microwell is unequal for at least two microwells of the plurality of microwells, and wherein the second fluid seals the content of the microwell.

Disclosed herein include methods for determining the number of occurrences of a target nucleic acid molecule in single cells. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; (b) capturing single cells and single beads in the plurality of microwells, wherein a single bead comprises a plurality of tethered barcodes, and wherein the plurality of tethered barcodes further comprises: i) a bead-specific cellular label; ii) a diverse set of molecular labels; and iii) a plurality of target binding regions capable of hybridizing with target nucleic acid molecules; (c) co-injecting a first fluid and a second fluid into the fluidic channel, wherein the first fluid is introduced into the fluidic channel immediately before the second fluid, wherein the first fluid interfaces with a surface of the content of the microwell for a duration, wherein the first fluid comprises a lysis buffer, wherein one or more components of the first fluid enter the microwell by diffusion and initiate cellular lysis, and wherein the second fluid seals the content of the microwell; (d) hybridizing target nucleic acid molecules released from single cells following cellular lysis with the plurality of target binding regions tethered to single beads in a stochastic manner; (e) performing an extension reaction to create a plurality of molecular conjugates each comprising a barcode and a portion of a complementary sequence of one of the target nucleic acid molecule; (f) amplifying and sequencing the molecular conjugates; and (g) determining the number of occurrences of the target nucleic acid molecule in the single cells.

Disclosed herein include methods of measuring the dose-dependent phenotypic effects of an agent on single cells. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; (b) capturing single cells in the plurality of microwells; (c) co-injecting a first fluid and a second fluid into the fluidic channel, wherein the first fluid is introduced into the fluidic channel immediately before the second fluid, wherein the first fluid interfaces with a surface of the content of the microwell for a duration, wherein the first fluid comprises one or more components, wherein the one or more components of the first fluid comprise an agent, wherein the flow rate of the first fluid is not uniform along the longitudinal path of the fluidic channel, wherein the agent enters the microwell by diffusion during the duration, wherein the final concentration of the agent in the content of the microwell is unequal for at least two microwells of the plurality of microwells, and wherein the second fluid seals the content of the microwell; and (d) measuring one or more phenotypic effects dependent on the final concentration of the agent in the microwell.

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, or barcode sequences (e.g., molecular labels). The adaptors can be linear. The adaptors can be pre-adenylated adaptors. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adaptor can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adaptors can comprise identical and/or universal nucleic acid sequences and the 3' adaptors can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adaptors (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" can mean that two or more species are identifiable as being co-located at a point in time. An association can mean that two or more species are or were within a similar container. An association can be an informatics association. For example, digital information regarding two or more species can be stored and can be used to determine that one or more of the species were co-located at a point in time. An association can also be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label. An association can comprise hybridization between two molecules (such as a target molecule and a label).

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, a "complementary" sequence can refer to a "complement" or a "reverse complement" of a sequence. It is understood from the disclosure that if a molecule can hybridize to another molecule it may be complementary, or partially complementary, to the molecule that is hybridizing.

As used herein, the term "digital counting" can refer to a method for estimating a number of target molecules in a sample. Digital counting can include the step of determining a number of unique labels that have been associated with targets in a sample. This methodology, which can be stochastic in nature, transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of barcodes (e.g., stochastic barcodes) made up of many different labels. A non-depleting reservoir can comprise large numbers of different barcodes such that when the non-depleting reservoir is associated with a pool of targets each target is likely to be associated with a unique barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of barcodes detected then allows calculation of the number of target molecules present in the original collection or sample. When the ratio of the number of copies of a target molecule present to the number of unique barcodes is low, the labeled target molecules are highly unique (i.e., there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (e.g., morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene ($—CH_2$), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g., adenine (A) and guanine (G)), and the pyrimidine bases, (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C\equiv C—CH3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g., 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo [2,3-d]pyrimidin-2-one).

As used herein, the term "sample" can refer to a composition comprising targets. Suitable samples for analysis by the disclosed methods, devices, and systems include cells, tissues, organs, or organisms. A sample can refer to a plurality of cells. The sample can refer to a monolayer of cells. The sample can refer to a thin section (e.g., tissue thin section). The sample can refer to a solid or semi-solid collection of cells that can be place in one dimension on an array.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A plurality of solid supports spaced in an array may not comprise a substrate. A solid support may be used interchangeably with the term "bead."

As used herein, the term "stochastic barcode" can refer to a polynucleotide sequence comprising labels of the present disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a barcode (e.g., a stochastic barcode). Exemplary suitable targets for analysis by the disclosed methods, devices, and systems include oligonucleotides, DNA, RNA, mRNA, microRNA, tRNA, and the like. Targets can be single or double stranded. In some embodiments, targets can be proteins, peptides, or polypeptides. In some embodiments, targets are lipids. As used herein, "target" can be used interchangeably with "species."

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize to barcodes (e.g., stochastic barcodes) to generate gene-specific barcodes. A universal adaptor sequence can, for example, be a known sequence that is universal across all barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a barcode. For example, a universal adaptor sequence may be part of an oligonucleotide comprising a target-specific sequence to generate a nucleotide sequence that is complementary to a target nucleic acid. A second oligonucleotide comprising a barcode and a complementary sequence of the universal adaptor sequence may hybridize with the nucleotide sequence and generate a target-specific barcode (e.g., a target-specific stochastic barcode). In some embodiments, a universal adaptor primer has a sequence that is different from a universal PCR primer used in the methods of this disclosure.

Barcodes

Barcoding, such as stochastic barcoding, has been described in, for example, Fu et al., *Proc Natl Acad Sci U.S.A.*, 2011 May 31, 108(22):9026-31; U.S. Patent Application Publication No. US2011/0160078; Fan et al., Science, 2015 Feb. 6, 347(6222):1258367; US Patent Application Publication No. US2015/0299784; and PCT Application Publication No. WO2015/031691; the content of each of these, including any supporting or supplemental information or material, is incorporated herein by reference in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5'amine that may link the barcode to a solid support 105. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g., seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequences (e.g., molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20, or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or be at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were barcoded. For example, a population of cells can be barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a bead), but different for different solid supports (e.g., beads). In some embodiments, at least 60%, 70%, 80%, 85%, 90%, 95%, 97%, 99% or 100%, of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or be at most, 1, 2, 3, 4, 5, 10, 15, 20, 25, 30, 35, 40, 45, 50, 100, 200, or 300, nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example, a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g., A well, a container, or a droplet). In some embodiments, multiple spatial labels are used together to encode one or more positions in space.

The spatial label can be identical for all barcodes attached to a given solid support (e.g., a bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or be at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode (e.g., a stochastic barcode) can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a bead), but different for different solid supports (e.g., beads).

In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or be at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or be at most, $10^2$, $10^3$, $10^4$, $10^5$, $10^6$, $10^7$, $10^8$, or $10^9$, unique barcode sequences. The unique molecular label sequences can be attached to a given solid support (e.g., a bead). In some embodiments, the unique molecular label sequence is partially or entirely encompassed by a particle (e.g., a hydrogel bead).

The length of a barcode can be different in different implementations. For example, a barcode can be, or be about, 1, 2, 3, 4, 5, 10, 15, 20, 25, 30, 35, 40, 45, 50, or a number or a range between any two of these values, nucleotides in length. As another example, a barcode can be at least, or be at most, 1, 2, 3, 4, 5, 10, 15, 20, 25, 30, 35, 40, 45, 50, 100, 200, or 300 nucleotides in length.

Molecular Labels

A barcode (e.g., a stochastic barcode) can comprise one or more molecular labels. Molecular labels can include barcode sequences. In some embodiments, a molecular label can comprise a nucleic acid sequence that provides identifying information for the specific type of target nucleic acid species hybridized to the barcode. A molecular label can comprise a nucleic acid sequence that provides a counter for the specific occurrence of the target nucleic acid species hybridized to the barcode (e.g., target-binding region).

In some embodiments, a diverse set of molecular labels are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, of unique molecular label sequences. For example, a plurality of barcodes can comprise about 6561 molecular labels with distinct sequences. As another example, a plurality of barcodes can comprise about 65536 molecular labels with distinct sequences. In some embodiments, there can be at least, or be at most, $10^2$, $10^3$, $10^4$, $10^5$, $10^6$, $10^7$, $10^8$, or $10^9$, unique molecular label sequences. Barcodes with unique molecular label sequences can be attached to a given solid support (e.g., a bead).

For barcoding (e.g., stochastic barcoding) using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or be at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g., target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g., an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, a poly(dA) sequence, a poly(dT) sequence, a poly(dG) sequence, a poly(dC) sequence, or a combination thereof. For example, the target binding region can be an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length. For example, an mRNA molecule can be reverse transcribed using a reverse transcriptase, such as Moloney murine leukemia virus (MMLV) reverse transcriptase, to generate a cDNA molecule with a poly(dC) tail. A barcode can include a target binding region with a poly(dG) tail. Upon base pairing between the poly(dG) tail of the barcode and the poly(dC) tail of the cDNA molecule, the reverse transcriptase switches template strands, from cellular RNA molecule to the barcode, and continues replication to the 5' end of the barcode. By doing so, the resulting cDNA molecule contains the sequence of the barcode (such as the molecular label) on the 3' end of the cDNA molecule.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A stochastic barcode (e.g., a stochastic barcode) can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode (e.g., a stochastic barcode) can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be labeled (e.g., stochastically labeled). The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequences, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10× Genomics (San Francisco, CA). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be disruptable (e.g., dissolvable, degradable). For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of cross-link bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
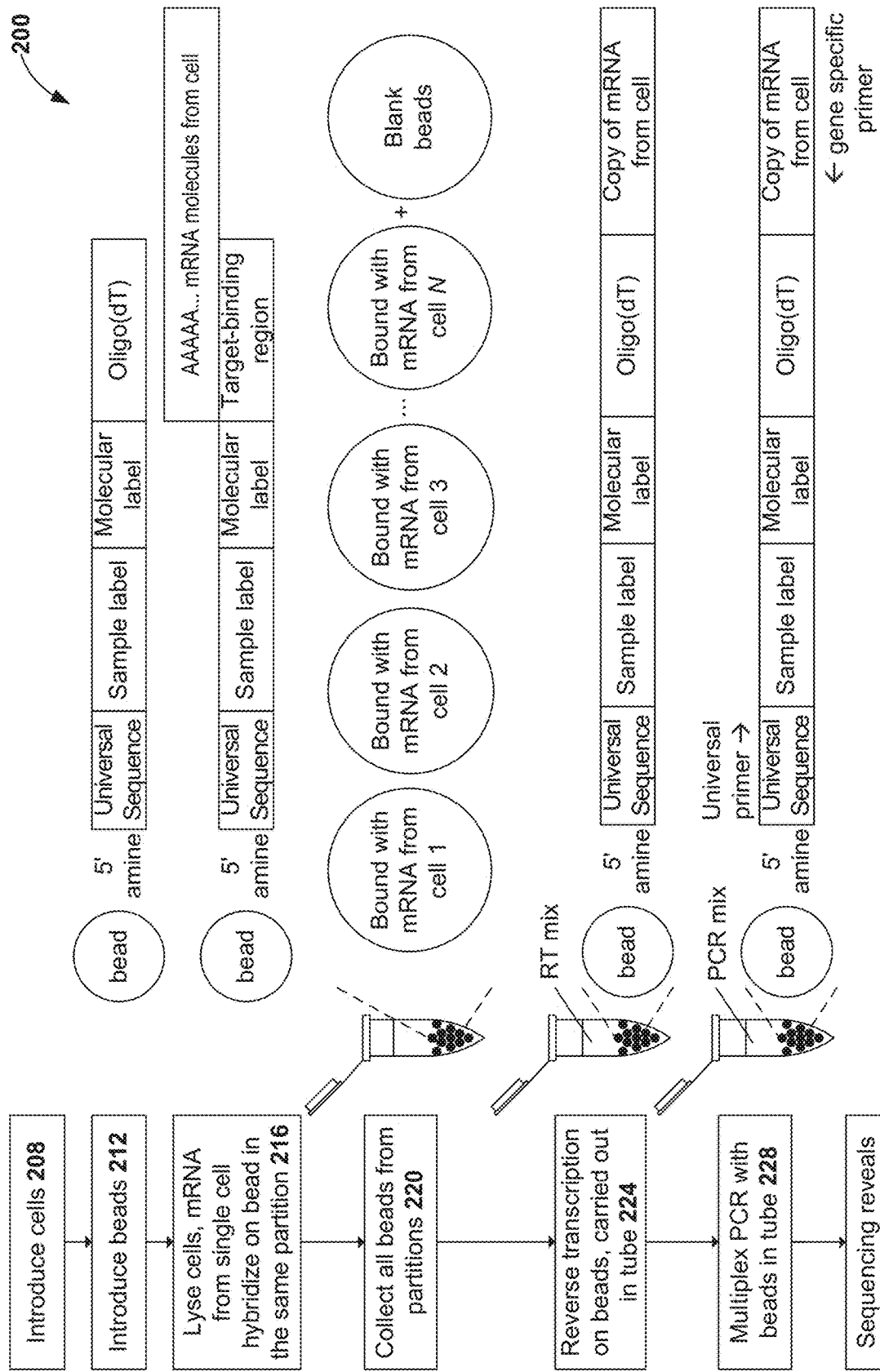
FIG. 2 shows a non-limiting exemplary workflow of barcoding and digital counting.

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode with different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or be at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized," are used interchangeably, and can refer to covalent or non-covalent means for attaching barcodes to a solid support. Any of a variety of different solid supports can be used as solid supports for attaching pre-synthesized barcodes or for in situ solid-phase synthesis of barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g., magnesium, molybdenum, lithium, and tantalum), superparamagnetic materials (e.g., ferrite ($Fe_3O_4$; magnetite) nanoparticles), ferromagnetic materials (e.g., iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example, beads). Each of the particles can comprise a plurality of oligonucleotides (e.g., barcodes). Each of the plurality of oligonucleotides can comprise a barcode sequence (e.g., a molecular label sequence), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometer. In some embodiments, the diameter of the bead can be, or be about, 0.1, 0.5, 1, 2, 3, 4, 5, 6, 7, 8, 9, 10, 20, 30, 40, 50 micrometer, or a number or a range between any two of these values.

The diameter of the bead can be related to the diameter of the wells of the substrate. In some embodiments, the diameter of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameter of the bead can be at least, or be at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameter of the bead can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameter of the beads can be at least, or be at most, 10%, 20%, 30%, 40%, 50%, 60%, 70%, 80%, 90%, 100%, 150%, 200%, 250%, or 300% longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g., impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example, due to swelling in an organic or inorganic solution. A bead can be hydrophobic. A bead can be hydrophilic. A bead can be biocompatible.

A solid support (e.g., a bead) can be visualized. The solid support can comprise a visualizing tag (e.g., fluorescent dye). A solid support (e.g., a bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

Substrates and Microwell Array

As used herein, a substrate can refer to a type of solid support. A substrate can refer to a solid support that can comprise barcodes or stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., a bead). A microwell can comprise barcode reagents of the disclosure.

Methods of Barcoding

The disclosure provides for methods for estimating the number of distinct targets at distinct locations in a physical sample (e.g., tissue, organ, tumor, cell). The methods can comprise placing barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two dimensional map or a three dimensional map of the sample. The two dimensional map and the three dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after barcoding the plurality of targets in the sample. in some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., formsa planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be cross-linked to barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, 10, or more. The pH of the lysis buffer can be at most about 1, 2, 3, 4, 5, 6, 7, 8, 9, 10, or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7%, or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7%, or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g., buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g., an EcoRI sticky-end overhang). The assay procedure can further comprise treating the target nucleic acids with a restriction enzyme (e.g., EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription or Nucleic Acid Extension

The disclosure provides for a method to create a target-barcode conjugate using reverse transcription (e.g., at block 224 of FIG. 2) or nucleic acid extension. The target-barcode conjugate can comprise the barcode and a complementary sequence of all or a portion of the target nucleic acid (i.e., a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of an mRNA molecule to a labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, a target is a cDNA molecule. For example, an mRNA molecule can be reverse transcribed using a reverse transcriptase, such as Moloney murine leukemia virus (MMLV) reverse transcriptase, to generate a cDNA molecule with a poly(dC) tail. A barcode can include a target binding region with a poly(dG) tail. Upon base pairing between the poly(dG) tail of the barcode and the poly(dC) tail of the cDNA molecule, the reverse transcriptase switches template strands, from cellular RNA molecule to the barcode, and continues replication to the 5' end of the barcode. By doing so, the resulting cDNA molecule contains the sequence of the barcode (such as the molecular label) on the 3' end of the cDNA molecule.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular label and/or barcode sequence (e.g., a molecular label). The amplification reactions can comprise amplifying at least a portion of a sample tag, a cell label, a spatial label, a barcode sequence (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled amplicon (e.g., a stochastically labeled amplicon). The labeled amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholine and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded targets (e.g., stochastically barcoded targets) or barcoded fragments of the targets. The barcode sequences of different barcodes (e.g., the molecular labels of different stochastic barcodes) can be different from one another. Generating an indexed library of the barcoded targets includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligo-nucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligo-nucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Barcoding (e.g., stochastic barcoding) can include using nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at block 232 of FIG. 2.

Figure 3:
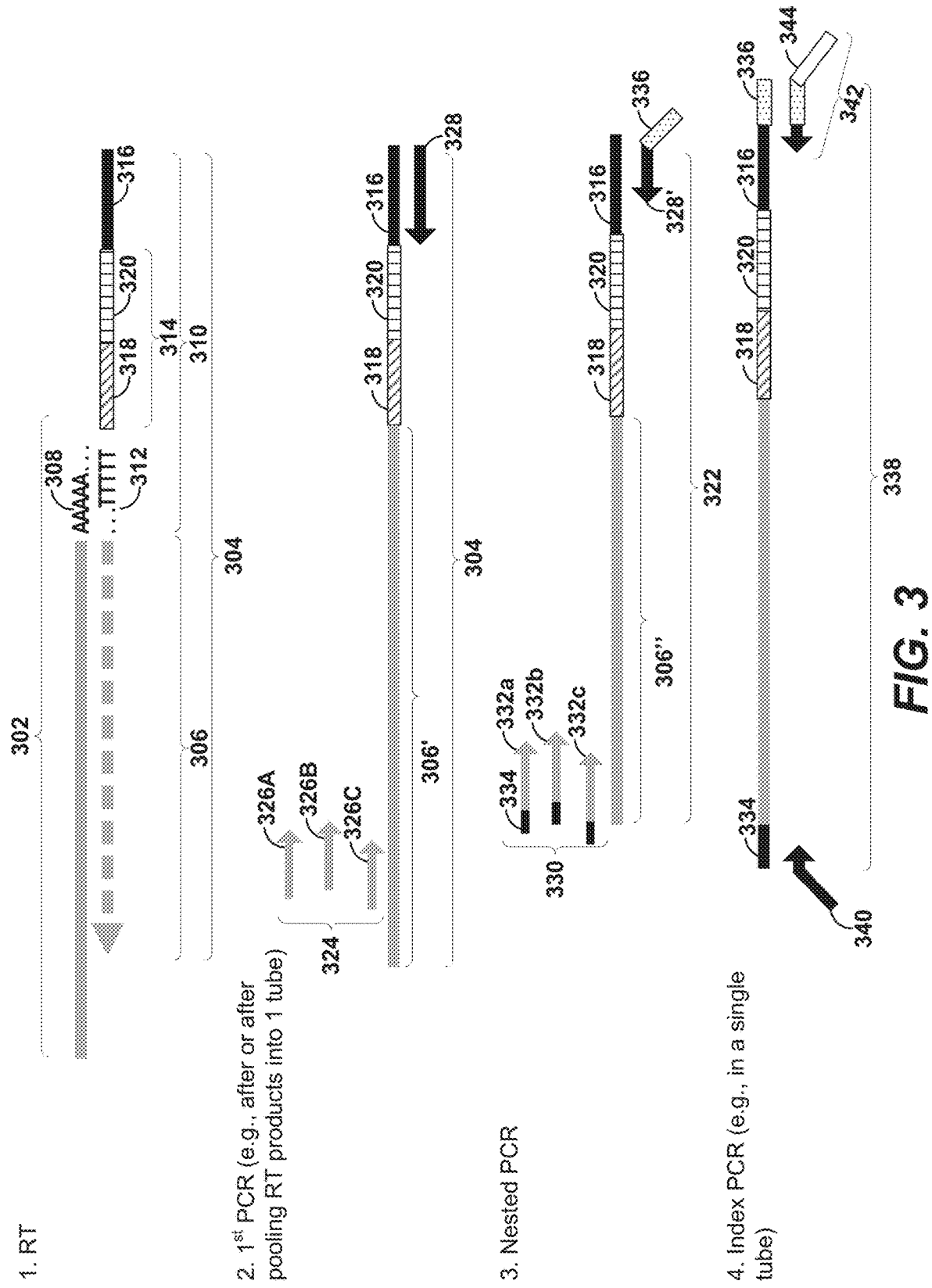
FIG. 3 is a schematic illustration showing a non-limiting exemplary process for generating an indexed library of targets barcoded at the 3'-ends from a plurality of targets.

FIG. 3 is a schematic illustration showing a non-limiting exemplary process of generating an indexed library of the barcoded targets (e.g., stochastically barcoded targets), such as barcoded mRNAs or fragments thereof. As shown in step 1, the reverse transcription process can encode each mRNA molecule with a unique molecular label sequence, a cell label sequence, and a universal PCR site. In particular, RNA molecules 302 can be reverse transcribed to produce labeled cDNA molecules 304, including a cDNA region 306, by hybridization (e.g., stochastic hybridization) of a set of barcodes (e.g., stochastic barcodes) 310 to the poly(A) tail region 308 of the RNA molecules 302. Each of the barcodes 310 can comprise a target-binding region, for example a poly(dT) region 312, a label region 314 (e.g., a barcode sequence or a molecule), and a universal PCR region 316.

In some embodiments, the cell label sequence can include 3 to 20 nucleotides. In some embodiments, the molecular label sequence can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise using a $1^{st}$ PCR primer pool 324 comprising custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Cellular Component Binding Reagents Associated with Oligonucleotides

Some embodiments disclosed herein provide a plurality of compositions each comprising a cellular component binding reagent (such as a protein binding reagent) that is conjugated with an oligonucleotide, wherein the oligonucleotide comprises a unique identifier for the cellular component binding reagent that it is conjugated with. Cellular component binding reagents (such as barcoded antibodies) and their uses (such as sample indexing of cells) have been described in U.S. Patent Application Publication No. US2018/0088112 and U.S. Patent Application Publication No. US2018/0346970; the content of each of these is incorporated herein by reference in its entirety.

In some embodiments, the cellular component binding reagent is capable of specifically binding to a cellular component target. For example, a binding target of the cellular component binding reagent can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component binding reagent (e.g., a protein binding reagent) is capable of specifically binding to an antigen target or a protein target. In some embodiments, each of the oligonucleotides can comprise a barcode, such as a stochastic barcode. A barcode can comprise a barcode sequence (e.g., a molecular label), a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., unanchored to a solid support or anchored to a solid support. The poly(A) tail can be from about 10 to 50 nucleotides in length. In some embodiments, the poly(A) tail can be 18 nucleotides in length. The oligonucleotides can comprise deoxyribonucleotides, ribonucleotides, or both.

The unique identifiers can be, for example, a nucleotide sequence having any suitable length, for example, from about 4 nucleotides to about 200 nucleotides. In some embodiments, the unique identifier is a nucleotide sequence of 25 nucleotides to about 45 nucleotides in length. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise, or comprise about, 20, 30, 40, 50, 60, 70, 80, 90, 100, 200, 300, 400, 500, 600, 700, 800, 900, 1000, 2000, 5000, or a number or a range between any two of these values, different unique identifiers. The diverse set of unique identifiers can comprise at least, or comprise at most, 20, 30, 40, 50, 60, 70, 80, 90, 100, 200, 300, 400, 500, 600, 700, 800, 900, 1000, 2000, or 5000, different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by, or by about, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or a number or a range between any two of these values. In some embodiments, the sequences of the set of unique identifiers are different from each other, or the complement thereof, by at least, or by at most, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides. In some embodiments, the sequences of the set of unique identifiers are different from each other, or the complement thereof, by at least 3%, at least 5%, at least 8%, at least 10%, at least 15%, at least 20%, or more.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable cellular component binding reagents are contemplated in this disclosure, such as protein binding reagents, antibodies or fragments thereof, aptamers, small molecules, ligands, peptides, oligonucleotides, etc., or any combination thereof. In some embodiments, the cellular component binding reagents can be polyclonal antibodies, monoclonal antibodies, recombinant antibodies, single chain antibody (sc-Ab), or fragments thereof, such as Fab, Fv, etc. In some embodiments, the plurality of cellular component binding reagents can comprise, or comprise about, 20, 30, 40, 50, 60, 70, 80, 90, 100, 200, 300, 400, 500, 600, 700, 800, 900, 1000, 2000, 5000, or a number or a range between any two of these values, different cellular component reagents. In some embodiments, the plurality of cellular component binding reagents can comprise at least, or comprise at most, 20, 30, 40, 50, 60, 70, 80, 90, 100, 200, 300, 400, 500, 600, 700, 800, 900, 1000, 2000, or 5000, different cellular component reagents.

The oligonucleotide can be conjugated with the cellular component binding reagent through various mechanism. In some embodiments, the oligonucleotide can be conjugated with the cellular component binding reagent covalently. In some embodiment, the oligonucleotide can be conjugated with the cellular component binding reagent non-covalently. In some embodiments, the oligonucleotide is conjugated with the cellular component binding reagent through a linker. The linker can be, for example, cleavable or detachable from the cellular component binding reagent and/or the oligonucleotide. In some embodiments, the linker can comprise a chemical group that reversibly attaches the oligonucleotide to the cellular component binding reagents. The chemical group can be conjugated to the linker, for example, through an amine group. In some embodiments, the linker can comprise a chemical group that forms a stable bond with another chemical group conjugated to the cellular component binding reagent. For example, the chemical group can be a UV photocleavable group, a disulfide bond, a streptavidin, a biotin, an amine, etc. In some embodiments, the chemical group can be conjugated to the cellular component binding reagent through a primary amine on an amino acid, such as lysine, or the N-terminus. Commercially available conjugation kits, such as the Protein-Oligo Conjugation Kit (Solulink, Inc., San Diego, California), the Thunder-Link® oligo conjugation system (Innova Biosciences, Cambridge, United Kingdom), etc., can be used to conjugate the oligonucleotide to the cellular component binding reagent.

The oligonucleotide can be conjugated to any suitable site of the cellular component binding reagent (e.g., a protein binding reagent), as long as it does not interfere with the specific binding between the cellular component binding reagent and its cellular component target. In some embodiments, the cellular component binding reagent is a protein, such as an antibody. In some embodiments, the cellular component binding reagent is not an antibody. In some embodiments, the oligonucleotide can be conjugated to the antibody anywhere other than the antigen-binding site, for example, the Fc region, the $C_H1$ domain, the $C_H2$ domain, the $C_H3$ domain, the $C_L$ domain, etc. Methods of conjugating oligonucleotides to cellular component binding reagents (e.g., antibodies) have been previously disclosed, for example, in U.S. Pat. No. 6,531,283, the content of which is hereby expressly incorporated by reference in its entirety. Stoichiometry of oligonucleotide to cellular component binding reagent can be varied. To increase the sensitivity of detecting the cellular component binding reagent specific oligonucleotide in sequencing, it may be advantageous to increase the ratio of oligonucleotide to cellular component binding reagent during conjugation. In some embodiments, each cellular component binding reagent can be conjugated with a single oligonucleotide molecule. In some embodiments, each cellular component binding reagent can be conjugated with more than one oligonucleotide molecule, for example, at least, or at most, 2, 3, 4, 5, 10, 20, 30, 40, 50, 100, 1000, or a number or a range between any two of these values, oligonucleotide molecules wherein each of the oligonucleotide molecule comprises the same, or different, unique identifiers. In some embodiments, each cellular component binding reagent can be conjugated with more than one oligonucleotide molecule, for example, at least, or at most, 2, 3, 4, 5, 10, 20, 30, 40, 50, 100, 1000, oligonucleotide molecules, wherein each of the oligonucleotide molecule comprises the same, or different, unique identifiers.

In some embodiments, the plurality of cellular component binding reagents are capable of specifically binding to a plurality of cellular component targets in a sample, such as a single cell, a plurality of cells, a tissue sample, a tumor sample, a blood sample, or the like. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular component targets can comprise intracellular cellular components. In some embodiments, the plurality of cellular components can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values, of all the cellular components (e.g., proteins) in a cell or an organism. In some embodiments, the plurality of cellular components can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all the cellular components (e.g., proteins) in a cell or an organism. In some embodiments, the plurality of cellular component targets can comprise, or comprise about, 2, 3, 4, 5, 10, 20, 30, 40, 50, 100, 1000, 10000, or a number or a range between any tow of these values, different cellular component targets. In some embodiments, the plurality of cellular component targets can comprise at least, or comprise at most, 2, 3, 4, 5, 10, 20, 30, 40, 50, 100, 1000, 10000, different cellular component targets.

Sample Indexing Using Oligonucleotide-Conjugated Cellular Component Binding Reagent Disclosed herein include methods for sample identification. In some embodiments, the method comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; barcoding (e.g., stochastically barcoding) the sample indexing oligonucleotides using a plurality of barcodes (e.g., stochastic barcodes) to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

An oligonucleotide-conjugated with an antibody, an oligonucleotide for conjugation with an antibody, or an oligonucleotide previously conjugated with an antibody is referred to herein as an antibody oligonucleotide ("AbOligo"). Antibody oligonucleotides in the context of sample indexing are referred to herein as sample indexing oligonucleotides. An antibody conjugated with an antibody oligonucleotide is referred to herein as a hot antibody or an oligonucleotide antibody. An antibody not conjugated with an antibody oligonucleotide is referred to herein as a cold antibody or an oligonucleotide free antibody. An oligonucleotide-conjugated with a binding reagent (e.g., a protein binding reagent), an oligonucleotide for conjugation with a binding reagent, or an oligonucleotide previously conjugated with a binding reagent is referred to herein as a reagent oligonucleotide. Reagent oligonucleotides in the context of sample indexing are referred to herein as sample indexing oligonucleotides. A binding reagent conjugated with an antibody oligonucleotide is referred to herein as a hot binding reagent or an oligonucleotide binding reagent. A binding reagent not conjugated with an antibody oligonucleotide is referred to herein as a cold binding reagent or an oligonucleotide free binding reagent.

Simultaneous Quantitative Analysis of Cellular Component and Nucleic Acid Targets In some embodiments, the methods disclosed herein can also be used for simultaneous quantitative analysis of a plurality of cellular component targets (e.g., protein targets) and a plurality of nucleic acid target molecules in a sample using the compositions disclosed herein and oligonucleotide probes that can associate a barcode sequence (e.g., a molecular label sequence) to both the oligonucleotides of the cellular component binding reagents and nucleic acid target molecules. Other methods of simultaneous quantitative analysis of a plurality of cellular component targets and a plurality of nucleic acid target molecules are described in U.S. Patent Application Publication No. US2018/0088112 and U.S. Patent Application Publication No. US2018/0346970; the content of each of these is incorporated herein by reference in its entirety. In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, or a mixture of cells from different subjects.

In some embodiments, the sample can comprise a plurality of single cells separated into individual compartments, such as microwells in a microwell array or droplets.

In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular components can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values, of all the cellular components, such as expressed proteins, in an organism, or one or more cells of the organism. In some embodiments, the plurality of cellular components can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all the cellular components, such as proteins could be expressed, in an organism, or one or more cells of the organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, or 10000, different cellular component targets.

In some embodiments, the plurality of cellular component binding reagents is contacted with the sample for specific binding with the plurality of cellular component targets. Unbound cellular component binding reagents can be removed, for example, by washing. In embodiments where the sample comprises cells, any cellular component binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1%, 5%, 10%, 15%, 20%, 25%, 30%, 35%, 40%, 45%, 50%, 55%, 60%, 65%, 70%, 75%, 80%, 85%, 90%, 95%, or 100% of wells of the substrate receive a single cell. The population of cells can be diluted such that at most 1%, 5%, 10%, 15%, 20%, 25%, 30%, 35%, 40%, 45%, 50%, 55%, 60%, 65%, 70%, 75%, 80%, 85%, 90%, 95%, or 100% of wells of the substrate receive a single cell. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100% of the number of wells on the substrate. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100% of the number of wells on the substrate. In some instances, the population of cells is diluted such that the number of cell is about 10% of the number of wells in the substrate.

Distribution of single cells into wells of the substrate can follow a Poisson distribution. For example, there can be at least a 0.1%, 0.5%, 1%, 2%, 3%, 4%, 5%, 6%, 7%, 8%, 9%, or 10%, or more probability that a well of the substrate has more than one cell. There can be at least a 0.1%, 0.5%, 1%, 2%, 3%, 4%, 5%, 6%, 7%, 8%, 9%, or 10%, or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the cellular component binding reagents can be additionally conjugated with fluorescent molecules to enable flow sorting of cells into individual compartments.

In some embodiments, the methods disclosed herein provide contacting a plurality of compositions with the sample for specific binding with the plurality of cellular component targets. It would be appreciated that the conditions used may allow specific binding of the cellular component binding reagents, e.g., antibodies, to the cellular component targets. Following the contacting step, unbound compositions can be removed. For example, in embodiments where the sample comprises cells, and the compositions specifically bind to cellular component targets are on the cell surface, such as cell-surface proteins, unbound compositions can be removed by washing the cells with buffer such that only compositions that specifically bind to the cellular component targets remain with the cells.

In some embodiments, the methods disclosed herein can provide releasing the plurality of nucleic acid target molecules from the sample, e.g., cells. For example, the cells can be lysed to release the plurality of nucleic acid target molecules. Cell lysis may be accomplished by any of a variety of means, for example, by chemical treatment, osmotic shock, thermal treatment, mechanical treatment, optical treatment, or any combination thereof. Cells may be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof.

It would be appreciated by one of ordinary skill in the art that the plurality of nucleic acid molecules can comprise a variety of nucleic acid molecules. In some embodiments, the plurality of nucleic acid molecules can comprise, DNA molecules, RNA molecules, genomic DNA molecules, mRNA molecules, rRNA molecules, siRNA molecules, or a combination thereof, and can be double-stranded or single-stranded. In some embodiments, the plurality of nucleic acid molecules comprise, or comprise about, 100, 1000, 10000, 20000, 30000, 40000, 50000, 100000, 1000000, or a number or a range between any two of these values, species. In some embodiments, the plurality of nucleic acid molecules comprise at least, or comprise at most, 100, 1000, 10000, 20000, 30000, 40000, 50000, 100000, or 1000000, species. In some embodiments, the plurality of nucleic acid molecules can be from a sample, such as a single cell, or a plurality of cells. In some embodiments, the plurality of nucleic acid molecules can be pooled from a plurality of samples, such as a plurality of single cells.

In some embodiments, the methods disclosed herein can comprise associating a barcode (e.g., a stochastic barcode), which can include a barcode sequence (such as a molecular label), a cell label, a sample label, etc., or any combination thereof, to the plurality of nucleic acid target molecules and the plurality of oligonucleotides of the cellular component binding reagents. For example, a plurality of oligonucleotide probes comprising a stochastic barcode can be used to hybridize to the plurality of nucleic acid target molecules and the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes are in close proximity to the plurality of nucleic acid target molecules and the plurality of oligonucleotides of the cellular component binding reagents, the plurality of nucleic acid target molecules and the plurality of oligonucleotides of the cellular component binding reagents can hybridize to the oligonucleotide probes. The oligonucleotide probes can be contacted at a non-depletable ratio such that each distinct nucleic acid target molecules and oligonucleotides of the cellular component binding reagents can associate with oligonucleotide probes having different barcode sequences (e.g., molecular labels) of the disclosure.

In some embodiments, the methods disclosed herein provide detaching the oligonucleotides from the cellular component binding reagents that are specifically bound to the cellular component targets. Detachment can be performed in a variety of ways to separate the chemical group from the cellular component binding reagent, such as UV photocleaving, chemical treatment (e.g., dithiothreitol treatment), heating, enzyme treatment, or any combination thereof. Detaching the oligonucleotide from the cellular component binding reagent can be performed either before, after, or during the step of hybridizing the plurality of oligonucleotide probes to the plurality of Microwells Microwell Shapes and Sizes Microwells can be fabricated in a variety of shapes. Non-limiting exemplary well geometries can include cylindrical, conical, hemispherical, rectangular, or polyhedral (e.g., three dimensional geometries comprised of several planar faces, for example, hexagonal columns, octagonal columns, inverted triangular pyramids, inverted square pyramids, inverted pentagonal pyramids, inverted hexagonal pyramids, or inverted truncated pyramids). The microwells can comprise a shape that combines two or more of these geometries. For example, a microwell can be partly cylindrical, with the remainder having the shape of an inverted cone. A microwell can include two side-by-side cylinders, one of larger diameter (e.g. that corresponds roughly to the diameter of the beads) than the other (e.g. that corresponds roughly to the diameter of the cells), that are connected by a vertical channel (that is, parallel to the cylinder axes) that extends the full length (depth) of the cylinders. The location of the opening of the microwell can vary. For example, the opening of the microwell can be at the upper surface of the substrate. For example, the opening of the microwell can be at the lower surface of the substrate. The shape of the close end, for example the bottom, of the microwell can vary. For example, the closed end of the microwell can be flat. For example, the closed end of the microwell can have a curved surface (e.g., convex or concave). The shape and/or size of the microwell can be determined based on the types of cells or solid supports to be trapped within the microwells. In some embodiments, a microwell can have a non-circular cross section (e.g., square or hexagonal) in a plane of the substrate.

Microwells can be fabricated in a variety of sizes. Microwell size can be characterized, for example, in terms of the diameter and/or the depth of the microwells. The diameter of the microwell can refer to the largest circle that can be inscribed within the planar cross-section of the microwell geometry. The diameter of the microwells can, in some embodiments, range from about 1-fold to about 10-fold the diameter of the cells or solid supports to be trapped within the microwells. In some embodiments, the microwell diameter can be, or be about, 1-fold, 1.5-fold, 2-fold, 3-fold, 4-fold, 5-fold, 6-fold, 7-fold, 8-fold, 9-folds, 10-fold, or a number or a range between any two of these values, the diameter of the cells or the solid supports to be trapped within the microwells. In some embodiments, the microwell diameter can be at least, or at most, 1-fold, 1.5-fold, 2-fold, 3-fold, 4-fold, 5-fold, 6-fold, 7-fold, 8-fold, 9-folds, 10-fold the diameter of the cells or the solid supports to be trapped within the microwells. In some embodiments, the microwell diameter can be about 2.5-fold the diameter of the cells or solid supports to be trapped within the microwells.

The diameter of a microwell can be specified in terms of absolute dimensions. The diameter of a microwell can range from about 1 nanometer to about 1000 micrometers. In some embodiments, the microwell diameter can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the microwell diameter can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell diameter can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the microwell diameter can be at least, or at most 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell diameter can be about 30 micrometers.

The depth of the microwell can vary, for example, to provide efficient trapping of droplets, for example cells and solid supports, or to provide efficient exchange of assay buffers and other reagents contained within the wells. The ratio of diameter to depth (i.e. aspect ratio) can be varied such that once a cell and/or a solid support settle inside a microwell, they will not be displaced by fluid motion above the microwell. In some embodiments, the depth of the microwell can be smaller than the diameter of the bead. For example, the depth of the microwell can be, or be about, 5%, 10%, 20%, 30%, 40%, 50%, 60%, 70%, 80%, 90%, 99%, 99.9%, 100%, or a number or a range between any two of these values, of the diameter of the bead. For example, the depth of the microwell can be at least, or at most, 5%, 10%, 20%, 30%, 40%, 50%, 60%, 70%, 80%, 90%, 99%, 99.9%, 100% of the diameter of the bead. In some embodiments, synthetic particles such as beads can protrude outside of the microwells.

In some embodiments, a dimension of a microwell allows the microwell to contain at most one bead. A ratio of the width of the microwell to a diameter of the bead can vary, ranging from 1-1.9. In some embodiments, the ratio of the width of the microwell to the diameter of the bead can be, or be about, 1, 1.1, 1.2, 1.3, 1.4, 1.5, 1.6, 1.7, 1.8, 1.9, or a number or a range between any two of these values. In some embodiments, the ratio of the width of the microwell to the diameter of the bead can be at least, or at most, 1, 1.1, 1.2, 1.3, 1.4, 1.5, 1.6, 1.7, 1.8, or 1.9.

The dimensions of a microwell can vary such that the microwell has sufficient space to accommodate a solid support and a cell of various sizes without being dislodged by fluid motion above the microwell. The depth of a microwell can range from about 1-fold to about 10-fold the diameter of the cells or solid supports to be trapped within the microwells. In some embodiments, the microwell depth can be, or be about, 1-fold, 1.5-fold, 2-fold, 3-fold, 4-fold, 5-fold, 6-fold, 7-fold, 8-fold, 9-folds, 10-fold, or a number or a range between any two of these values, the diameter of the cells or solid supports to be trapped within the microwells. In some embodiments, the microwell depth can be at least, or at most, 1-fold, 1.5-fold, 2-fold, 3-fold, 4-fold, 5-fold, 6-fold, 7-fold, 8-fold, 9-folds, or 10-fold the diameter of the cells or solid supports to be trapped within the microwells. In some embodiments, the microwell depth can be about 2.5-fold the diameter of the cells or solid supports to be trapped within the microwells.

An aspect ratio of the width of the microwell to the depth of the microwell can vary, for example ranging from 0.1-2. In some embodiments, the aspect ratio of the width of the microwell to the depth of the microwell can be, or be about, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, or a number or a range between any two of these values. In some embodiments, the aspect ratio of the width of the microwell to the depth of the microwell can be at least, or at most, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2.

The depth of a microwell can be specified in terms of its absolute dimension. For example, the depth of a microwell can range from about 1 nanometer to about 1000 micrometers. In some embodiments, the microwell depth can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the microwell depth can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell depth can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the microwell depth can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell depth can be about 30 micrometers.

The volume of a microwell can vary, for example ranging from about 1 picoliter to about 1000 microliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, picoliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 picoliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, nanoliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 nanoliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, microliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000. In some embodiments, the microwell volume can be about 1 microliter.

The volume of a microwell can be characterized in terms of the variation in volume from one microwell to another. The coefficient of variation (expressed as a percentage) for microwell volume can range from about 1% to about 100%. The coefficient of variation for microwell volume can be, or be about, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. The coefficient of variation for microwell volume can be, at least or at most, 1%, 2%, 3%, 4%, 5%, 6%, 7%, 8%, 9%, 10%, 20%, 30%, 40%, 50%, 60%, 70%, 80%, 90%, or 100%. In some embodiments, the coefficient of variation of microwell volume can be about 2.5%.

The ratio of the volume of a microwell to the surface area of a bead (or to the surface area of a solid support to which barcode oligonucleotides can be attached) can vary, for example range from about 2.5 to about 1520 micrometers. In some embodiments, the ratio can be, or be about, 2.5, 5, 10, 100, 500, 750, 1000, 1520 micrometers, or a number or a range between any two of these values. In some embodiments, the ratio can be at least, or at most, 2.5, 5, 10, 100, 500, 750, 1000, or 1520 micrometers. In some embodiments, the ratio can be about 67.5 micrometers.

Microwell Arrangements

Microwells can be arranged in a one dimensional, two dimensional, or three-dimensional array. A three dimensional array can be achieved, for example, by stacking a series of two or more two dimensional arrays, for example by stacking two or more substrates comprising microwell arrays.

The pattern and spacing between microwells can vary to optimize the efficiency of trapping a single cell and a single solid support (e.g., bead) in each well, as well as to maximize the number of wells per unit area of the array. The microwells can be distributed according to a variety of random or non-random patterns. For example, they can be distributed entirely randomly across the surface of the array substrate, or they can be arranged in a square grid, rectangular grid, hexagonal grid, or the like.

The center-to-center distance or the center-to-center spacing between wells can vary from about 1 micrometer to about 1000 micrometers. In some embodiments, the center-to-center distance between wells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the center-to-center distance between wells can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the center-to-center distance between wells can be about 4890 micrometers.

The distance or the spacing between the edges of the microwells can vary from about 1 micrometer to about 1000 micrometers. In some embodiments, the distance between the edges of the wells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the distance between the edges of the wells can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the distance between the edges of the wells can be about 80 micrometers.

Microwell Density

A microwell array can comprise microwells at varying densities, for example ranging from 100 microwells per inch$^2$ to 1000000 microwells per inch$^2$. In some embodiments, the density of the microwell array can be, or be about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, or a number or a range between any two of these values, microwells per inch$^2$. In some embodiments, the density of the microwell array can be at least, or at most, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, or 10000000 microwells per inch$^2$. In some embodiments, the density of the microwell array can be, or be about, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, or a number or a range between any two of these values, microwells per cm$^2$. In some embodiments, the density of the microwell array can be at least, or at most, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 microwells per cm$^2$.

The total number of microwells on a substrate can vary based on the pattern and the spacing of the wells and the overall dimensions of the array. The number of microwells in the array can vary, for example, ranging from about 96 to about 1000000. In some embodiments, the number of microwells in the microarray can be, or be about, 96, 384, 1536, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, 10$^8$, 10$^9$, or a number or a range between any two of these values. In some embodiments, the number of microwells in the microarray can be at least, or at most, 96, 384, 1536, 2000, 3000, 4000, 5000, 6000, 7000, 8000, 9000, 10000, 20000, 30000, 40000, 50000, 60000, 70000, 80000, 90000, 100000200000, 300000, 400000, 500000, 600000, 700000, 800000, 900000, 1000000, 2000000, 3000000, 4000000, 5000000, 6000000, 7000000, 8000000, 9000000, 10000000, 10$^8$, 10$^9$. In some embodiments, the number of microwells in the microwell array can be about 96. In some embodiments, the number of microwells can be about 150000.

Microwell Substrate Surface Features

A microwell array can comprise surface features between the microwells that are designed to help guide cells and solid supports into the wells and/or to prevent them from settling on the surfaces between wells. Non-limiting examples of suitable surface features include, but are not limited to, domed, ridged, or peaked surface features that encircle the wells or straddle the surface between wells.

Substrate Fabrication Techniques

A microwell can be fabricated using any of a number of fabrication techniques. Non-limiting examples of fabrication methods that can be used include bulk micromachining techniques such as photolithography and wet chemical etching, plasma etching, or deep reactive ion etching; micromolding and micro-embossing; laser micromachining; 3D printing or other direct write fabrication processes using curable materials; and similar techniques.

Microwell arrays can be fabricated from a variety of substrate materials. The choice of material can depend on the choice of fabrication technique, and vice versa. Non-limiting examples of suitable materials include fused-silica, glass, polymers (e.g. agarose, gelatin, hydrogels, polydimethylsiloxane (PDMS) elastomer, polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, thiol-ene based resins, metals or metal films (e.g. aluminum, stainless steel, copper, nickel, chromium, and titanium), and the like. A hydrophilic material can be desirable for fabrication of the microwell arrays (e.g. to enhance wettability and minimize non-specific binding of cells and other biological material). Hydrophobic materials that can be treated or coated (e.g. by oxygen plasma treatment, or grafting of a polyethylene oxide surface layer) can be used for fabrication of the microwell arrays. The use of porous, hydrophilic materials for the fabrication of the microwell array can be desirable in order to facilitate capillary wicking/venting of entrapped gas or air bubbles in the device. The microwell array can be fabricated from a single material. The microwell array can comprise two or more different materials that have been bonded together or mechanically joined.

Substrate Shapes and Sizes

A substrate can have variety of shapes and sizes. For example, the shape (or footprint) of the substrate within which microwells are fabricated can be square, rectangular, circular, or irregular in shape. The size of can be characterized by its width, length, and depth.

The width of a substrate can vary, ranging from 0.1 inch to 10 inches. In some embodiments, the width of the substrate can be, or be about, 0.1, 0.2, 0.3, 0.4, 05, 0.6, 0.7, 0.8, 0.9, 1, 2, 3, 4, 5, 6, 7, 8, 9, 10 inches, or a number or a range between any two of these values. In some embodiments, the width of the substrate can be at least, or at most, 0.1, 0.2, 0.3, 0.4, 05, 0.6, 0.7, 0.8, 0.9, 1, 2, 3, 4, 5, 6, 7, 8, 9, or 10 inches. The width of the substrate can vary, ranging from 0.2 centimeter to 20 centimeters. In some embodiments, the width of the substrate can be, or be about, 0.2, 0.2, 0.3, 0.4, 05, 0.6, 0.7, 0.8, 0.9, 1, 2, 3, 4, 5, 6, 7, 8, 9, 10, 20 centimeters, or a number or a range between any two of these values. In some embodiments, the width of the substrate can be at least, or at most, 0.2, 0.3, 0.4, 05, 0.6, 0.7, 0.8, 0.9, 1, 2, 3, 4, 5, 6, 7, 8, 9, 10, or 20 centimeters.

The length of a substrate can vary, ranging from 0.1 inch to 10 inches. In some embodiments, the length of the substrate can be, or be about, 0.1, 0.2, 0.3, 0.4, 05, 0.6, 0.7, 0.8, 0.9, 1, 2, 3, 4, 5, 6, 7, 8, 9, 10 inches, or a number or a range between any two of these values. In some embodiments, the length of the substrate can be at least, or at most, 0.1, 0.2, 0.3, 0.4, 05, 0.6, 0.7, 0.8, 0.9, 1, 2, 3, 4, 5, 6, 7, 8, 9, or 10 inches. The length of the substrate can vary, ranging from 0.2 centimeter to 20 centimeters. In some embodiments, the length of the substrate can be, or be about, 0.2, 0.2, 0.3, 0.4, 05, 0.6, 0.7, 0.8, 0.9, 1, 2, 3, 4, 5, 6, 7, 8, 9, 10, 20 centimeters, or a number or a range between any two of these values. In some embodiments, the length of the substrate can be at least, or at most, 0.2, 0.3, 0.4, 05, 0.6, 0.7, 0.8, 0.9, 1, 2, 3, 4, 5, 6, 7, 8, 9, 10, or 20 centimeters.

In some embodiments, the footprint of a substrate, for example defined by its width and length, can be similar to that of a microtiter plate. In some embodiments, the footprint of the microwell array substrate can be similar to that of standard microscope slides. Non-limiting examples of the footprint of standard microscope slides include about 75 mm long×25 mm wide (about 3" long× about 1" wide) and about 75 mm long×50 mm wide (about 3" long×2" wide).

The thickness of the substrate within which the microwells are fabricated can range from about 0.1 mm thick to about 10 mm thick, or more. The thickness of the microwell array substrate can be, or be about, 0.1, 0.5, 1, 2, 3, 4, 5, 6, 7, 8, 9, 10 mm, or a number or a range between any two of these values. The thickness of the microwell array substrate can be at least, or at most, 10, 9, 8, 7, 6, 5, 4, 3, 2, 1, 0.5, 0.1 mm. The thickness of the microwell array substrate can be about 1 mm thick. The thickness of the microwell array substrate can be any value within these ranges, for example, the thickness of the microwell array substrate can be between about 0.2 mm and about 9.5 mm.

Microwell Array Surface Treatments

A variety of surface treatments and surface modification techniques can be used to modify the properties of microwell array surfaces. Examples include, but are not limited to, oxygen plasma treatments to render hydrophobic material surfaces more hydrophilic, the use of wet or dry etching techniques to smooth or roughen glass and silicon surfaces, adsorption or grafting of polyethylene oxide or other polymer layers, for example pluronic, or bovine serum albumin to substrate surfaces to render them more hydrophilic and less prone to non-specific adsorption of biomolecules and cells, the use of silane reactions to graft chemically-reactive functional groups to otherwise inert silicon and glass surfaces, etc. Photodeprotection techniques can be used to selectively activate chemically-reactive functional groups at specific locations in the array structure, for example, the selective addition or activation of chemically-reactive functional groups such as primary amines or carboxyl groups on the inner walls of the microwells can be used to covalently couple oligonucleotide probes, peptides, proteins, or other biomolecules to the walls of the microwells. The choice of surface treatment or surface modification utilized can depend on the type of surface property that is desired and/or on the type of material from which the microwell array is made.

Microwell Sealing

The openings of microwells can be sealed, for example, during cell lysis steps to prevent cross hybridization of target nucleic acid between adjacent microwells. A microwell (or array of microwells) can be sealed or capped using, for example, a flexible membrane or sheet of solid material (i.e. a plate or platten) that clamps against the surface of the microwell array substrate, or a suitable bead, where the diameter of the bead is larger than the diameter of the microwell.

A seal formed using a flexible membrane or sheet of solid material can comprise, for example, inorganic nanopore membranes (e.g., aluminum oxides), dialysis membranes, glass slides, coverslips, elastomeric films (e.g. PDMS), or hydrophilic polymer films (e.g., a polymer film coated with a thin film of agarose that has been hydrated with lysis buffer).

Solid supports (e.g., beads) used for capping the microwells can comprise any of the solid supports (e.g., beads) of the disclosure. In some embodiments, the solid supports are cross-linked dextran beads (e.g., Sephadex). Cross-linked dextran can range from about 10 micrometers to about 80 micrometers. In some embodiments, the cross-linked dextran beads used for capping can be, or be about, 10, 20, 30, 40, 50, 60, 70, 80 micrometers, or a number or a range between any two of these values. In some embodiments, the cross-linked dextran beads used for capping can be at least, or at most, 10, 20, 30, 40, 50, 60, 70, or 80 micrometers. The beads can be larger than the diameters of the microwells. In some embodiments, the beads can be, or be about, 10%, 20%, 30%, 40%, 50%, 60%, 70%, 80%, 90%, 99%, or a number or a range between any two of these values, larger than the diameter of the microwells. In some embodiments, the beads can be at least, or at most, 10%, 20%, 30%, 40%, 50%, 60%, 70%, 80%, 90%, or 99%, larger than the diameter of the microwells.

The seal or cap can allow buffer to pass into and out of the microwells, while preventing macromolecules (e.g., nucleic acids) from migrating out of the well. In some embodiments, a macromolecule of or of about 1, 2, 3, 4, 5, 6, 7, 8, 9, 10, 12, 13, 14, 15, 16, 17, 18, 19, 20, or a number or a range between any two of these values, nucleotides can be blocked from migrating into or out of the microwell by the seal or cap. In some embodiments, a macromolecule of at least, or at most, 1, 2, 3, 4, 5, 6, 7, 8, 9, 10, 12, 13, 14, 15, 16, 17, 18, 19, or 20 nucleotides can be blocked from migrating into or out of the microwell by the seal or cap.

Solid Support Manipulation

Solid supports (e.g., synthetic particles or beads) can be distributed among a substrate. Solid supports can be distributed among wells of the substrate, removed from the wells of the substrate, or otherwise transported through a device comprising one or more microwell arrays by means of centrifugation or other non-magnetic means. A microwell of a substrate can be pre-loaded with a solid support. A microwell of a substrate can hold or can hold about 1, 2, 3, 4, 5, 6, 7, 8, 9, 10 solid supports. A microwell of a substrate can hold at least, or at most, 1, 2, 3, 4, 5, 6, 7, 8, 9, 10 solid supports. In some embodiments, a microwell of a substrate can hold one solid support.

Consumables

Microwell arrays can be a consumable component of the assay system. Microwell arrays can be reusable. Microwell arrays can be configured for use as a stand-alone device for performing assays manually, or they can be configured to comprise a fixed or removable component of an instrument system that provides for full or partial automation of the assay procedure. In some embodiments of the disclosed methods, the bead-based libraries of barcodes can be deposited in the wells of the microwell array as part of the assay procedure. In some embodiments, the beads can be preloaded into the wells of the microwell array and provided to the user as part of, for example, a kit for performing barcoding and digital counting of nucleic acid targets.

Two Mated Microwell Arrays

In some embodiments, two mated microwell arrays can be provided, one pre-loaded with beads which are held in place by a first magnet, and the other for use by the user in loading individual cells. Following distribution of cells into the second microwell array, the two arrays can be placed face-to-face and the first magnet removed while a second magnet is used to draw the beads from the first array down into the corresponding microwells of the second array, thereby ensuring that the beads rest above the cells in the second microwell array and thus minimizing diffusional loss of target molecules following cell lysis, while maximizing efficient attachment of target molecules to the barcodes on the bead.

Substrates without Microwells

In some embodiments, a substrate does not include microwells. For example, beads can be assembled. For example, beads can be self-assembled. The beads can self-assemble into a monolayer. The monolayer can be on a flat surface of the substrate. The monolayer can be on a curved surface of the substrate. The bead monolayer can be formed by any method, such as alcohol evaporation.

Individual cells and beads can be compartmentalized using alternatives to microwells, for example, a single solid support and a single cell could be confined within a single droplet in an emulsion (e.g. in a droplet digital microfluidic system).

Cells could be confined within porous beads that themselves comprise the plurality of tethered barcodes. Individual cells and solid supports can be compartmentalized in any type of container, microcontainer, reaction chamber, reaction vessel, or the like.

Single cell barcoding can be performed without the use of microwells. Single cell barcoding assays can be performed without the use of any physical container. For example, barcoding without a physical container can be performed by embedding cells and beads in close proximity to each other within a polymer layer or gel layer to create a diffusional barrier between different cell/bead pairs. For example, barcoding without a physical container can be performed in situ, in vivo, on an intact solid tissue, on an intact cell, and/or subcellularly.

Particle Loading in Microwells

In some embodiments, a fluidic channel comprises a substrate on its bottom. The substrate can comprise a microwell array with a plurality of microwells. In some embodiments, a microwell can contain one particle (e.g., a cell or a bead). The percentage of microwells of a microwell array with one single particle can vary, for example, ranging from 25% to 90%. In some embodiments, the percentage of the microwells of the microwell array with a single particle (e.g., a single cell or a single bead) can be, or be about, 25%, 30%, 35%, 40%, 45%, 50%, 55%, 60%, 65%, 70%, 75%, 80%, 85%, 90%, 99%, or more of the microwells of the microwell array can comprise a single cell and a synthetic particle. In some embodiments, the percentage of the microwells of the microwell array with a single particle (e.g., a single cell or a single bead) can be at least, or at most, 25%, 30%, 35%, 40%, 45%, 50%, 55%, 60%, 65%, 70%, 75%, 80%, 85%, 90%, or 99%.

A microwell can contain two different types of particles (e.g., a cell and a bead). The percentage of microwells of a microwell array with one particle of each of two different types of particles can vary, for example, ranging from 25% to 90%. In some embodiments, the percentage of the microwells of the microwell array with one particle of each of two different types of particles (e.g., a single cell and a single bead) can be, or be about, 25%, 30%, 35%, 40%, 45%, 50%, 55%, 60%, 65%, 70%, 75%, 80%, 85%, 90%, 99%, or more of the microwells of the microwell array can comprise a single cell and a synthetic particle. In some embodiments, the percentage of the microwells of the microwell array with one particle of each of two different types of particles (e.g., a single cell or a single bead) can be at least, or at most, 25%, 30%, 35%, 40%, 45%, 50%, 55%, 60%, 65%, 70%, 75%, 80%, 85%, 90%, or 99.

Devices

Disclosed herein are devices for barcoding. In some embodiments, a device comprises: a flowcell comprising a fluidic channel, an inlet port, and an outlet port, wherein the fluidic channel comprises a ceiling, a fluidic channel sidewall, and a bottom. This other fluidic channel sidewall forms an edge with the ceiling and another edge with the bottom. The contact angle of the ceiling can be at least 10 degrees smaller than the contact angle of the fluidic channel sidewall. The bottom of the fluidic channel comprises a substrate which comprises a plurality of microwells. The inlet port and the outlet port are in fluid communication with the flowcell via the fluidic channel. The fluidic channel can comprise another fluidic channel sidewall. This other fluidic channel sidewall forms an edge with the ceiling and another edge with the bottom.

Flow Cells

The microwell array substrate can be packaged within a flowcell that provides for convenient interfacing with the rest of the fluid handling system and facilitates the exchange of fluids, e.g. cell and solid support suspensions, lysis buffers, rinse buffers, etc., that are delivered to the microwell array and/or emulsion droplet. Design features can include: (i) one or more inlet ports for introducing cell samples, solid support suspensions, or other assay reagents, (ii) one or more microwell array chambers designed to provide for efficient (e.g., uniform) filling and fluid-exchange while minimizing back eddies or dead zones, and (iii) one or more outlet ports for delivery of fluids to a sample collection point or a waste reservoir.

The design of the flowcell can include a plurality of microarray chambers that interface with a plurality of microwell arrays such that one or more different cell samples can be processed in parallel. The design of the flowcell can further include features for creating consistent (e.g., uniform) flow velocity profiles, i.e. "plug flow", across the width of the array chamber to provide for more efficient (e.g., uniform) delivery of cells and beads to the microwells, for example, by using a porous barrier located near the chamber inlet and upstream of the microwell array as a "flow diffuser", or by dividing each array chamber into several subsections that collectively cover the same total array area, but through which the divided inlet fluid stream flows in parallel. In some embodiments, the flowcell can enclose or incorporate more than one microwell array substrate. In some embodiments, the integrated microwell array/flowcell assembly can constitute a fixed component of the system. In some embodiments, the microwell array/flowcell assembly can be removable from the instrument.

In general, the dimensions of fluidic channel(s) and the array chamber(s) in flowcell designs will be optimized to (i) provide efficient (e.g., uniform) delivery of cells and beads to the microwell array, and (ii) to minimize sample and reagent consumption. The width of a fluidic channel can be different in different implementations, for example, ranging from 0.1 mm to 100 mm. In some embodiments, the width can be, or be about, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100 mm, or a number or a range between any two of these values. In some embodiments, the width can be at least, or at most, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or 100 mm.

The height of a fluidic channel can be different in different implementations, for example, ranging from 0.1 mm to 100 mm. In some embodiments, the height can be, or be about, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10 mm, or a number or a range between any two of these values. In some embodiments, the height can be at least, or at most, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, or 10 mm.

Flowcells can be fabricated using a variety of techniques and materials known to those of skill in the art. In general, a flowcell can be fabricated as a separate part and subsequently either mechanically clamped or permanently bonded to the microwell array substrate. Examples of suitable fabrication techniques include conventional machining, CNC machining, injection molding, 3D printing, alignment and lamination of one or more layers of laser or die-cut polymer films, or any of a number of microfabrication techniques such as photolithography and wet chemical etching, dry etching, deep reactive ion etching, or laser micromachining.

Once the flowcell part has been fabricated it can be attached to the microwell array substrate mechanically, e.g. by clamping it against the microwell array substrate (with or without the use of a gasket), or it can be bonded directly to the microwell array substrate using any of a variety of techniques (depending on the choice of materials used) known to those of skill in the art, for example, through the use of anodic bonding, thermal bonding, or any of a variety of adhesives or adhesive films, including epoxy-based, acrylic-based, silicone-based, UV curable, polyurethane-based, or cyanoacrylate-based adhesives. In some embodiments, the substrate can form the fluidic channel bottom of the fluidic channel, or the substrate can be on the fluidic channel bottom of the fluidic channel. In some embodiments, the substrate comprises silicon, fused-silica, glass, a polymer, a metal, an elastomer, polydimethylsiloxane, agarose, a hydrogel, or a combination thereof.

Flowcells can be fabricated using a variety of materials known to those of skill in the art. In general, the choice of material used will depend on the choice of fabrication technique used, and vice versa. Examples of suitable materials include, but are not limited to, silicon, fused-silica, glass, any of a variety of polymers, e.g. polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, metals (e.g. aluminum, stainless steel, copper, nickel, chromium, and titanium), a non-stick material such as teflon (PTFE), or a combination of these materials. The cyclic olefin polymers (COP) can comprise Zeonor 1020R or Zeonor 1060R.

Fluidic Channel

The fluidic channel can comprises a fluidic channel ceiling, two fluidic channel sidewalls, and a fluidic channel bottom. The fluidic channel ceiling and each fluidic channel sidewall form an edge. The fluidic channel sidewalls can have positive draft angles, for example, ranging from 1-15 degrees.

The width of the fluidic channel can be different in different implementations, for example, ranging from 1 mm to 20 mm. In some embodiments, the width of the fluidic channel can be, or be about, 1, 2, 3, 4, 5, 6, 7, 8, 9, 10, 11, 12, 13, 14, 15, 16, 17, 18, 19, 20 mm, or a number or a range between any two of these values. In some embodiments, the width of the fluidic channel can be at least, or at most, 1, 2, 3, 4, 5, 6, 7, 8, 9, 10, 11, 12, 13, 14, 15, 16, 17, 18, 19, or 20 mm. A larger width, for example 7 mm, can increase the flowcell area of a given flowcell length.

The height of the fluidic channel can be different in different implementations, for example, ranging from 0.1 mm to 2 mm. In some embodiments, the height of the fluidic channel can be, or be about, 0.1, 0.2, 0.3, 0.4, 0.5, 0.6, 0.7, 0.8, 0.9, 0.10, 0.11, 0.12, 0.13, 0.14, 0.15, 0.16, 0.17, 0.18, 0.19, 0.20 mm, or a number or a range between any two of these values. In some embodiments, the height of the fluidic channel can be at least, or at most, 0.1, 0.2, 0.3, 0.4, 0.5, 0.6, 0.7, 0.8, 0.9, 0.10, 0.11, 0.12, 0.13, 0.14, 0.15, 0.16, 0.17, 0.18, 0.19, or 0.20 mm.

In some embodiments, the contact angle of the fluidic channel ceiling is sufficiently smaller (e.g., 10, 20, 30, 40, 50, 60, 70, 80, or more degrees) than the contact angle of the fluidic channel sidewall to enable non-laminar flow within the fluidic channel. In some embodiments, the non-laminar flow within the fluidic channel enables agitation of a particle on the surface of the substrate by a flow within the fluidic channel. A speed of the flow at a boundary between the flow and the fluidic channel bottom can be non-zero. The relative flow velocity of a flow across a cross section of the fluidic channel can be constant or approximately constant. The non-laminar flow can be plug flow.

In some embodiments, the non-laminar flow can be approximately plug flow. The plug flow can be approximately horizontal plug flow. The horizontal plug flow can be capillary aided horizontal plug flow. In some embodiments, the plug flow may not depend on buoyancy of the gas. The plug flow may not depend on tilting of the device. The plug flow can be at a buffer-gas interface.

In some embodiments, the fluidic channel ceiling comprises a hydrophilic coating. For example, the hydrophilic coating can be a superhydrophilic coating. The hydrophilic coating can comprise polyethylene glycol (PEG), poly-Hema, pluronic acid F68, pluronic acid F108, pluronic acid F127, polysorbate 20, silicon dioxide ($SiO_2$), silicon nitride, or any combination thereof. The contact angle of the hydrophilic coating can be different in different implementations. In some embodiments, the contact angle of the hydrophilic coating can be, or be about, 0, 1, 2, 3, 4, 5, 6, 7, 8, 9, 10, 20, 23, 30, 40, 50, 60, 70, 80, 90 degrees, or a number or a range between any two of these values. In some embodiments, the contact angle of the hydrophilic coating can be at least, or at most, 0, 1, 2, 3, 4, 5, 6, 7, 8, 9, 10, 20, 23, 30, 40, 50, 60, 70, 80, or 90 degrees. The ceiling can be coated with the hydrophilic coating by sputtering, thermal growth, adsorption, covalent binding (e.g., by incubating the fluidic channel ceiling or the surface of the fluidic channel ceiling in a liquid with the coating material dissolved therein), or any combination thereof.

In some embodiments, hydrophilic and hydrophobic coatings can be used on a fluidic channel ceiling or a fluidic channel ceiling. The selective coating (also referred to herein as functionalization) of the fluidic channel boundaries (also referred to herein as the flowcell boundaries) can influence the direction of capillary flow within specific portions of the flowcell to control the profile of the gas-buffer fluid front profile in some embodiments.

Plug Flow

In some embodiments, the design of the flow cell may further include features for creating consistent (e.g., uniform) flow velocity profiles, i.e. "plug flow", across the width of the microwell chamber to provide for more efficient (e.g. uniform) delivery of cells and beads to the microwells, for example, by using a porous barrier located near the chamber inlet and upstream of the microwells as a "flow diffuser", or by dividing each microwell chamber into several subsections that collectively cover the same total array area, but through which the divided inlet fluid stream flows in parallel. Plug flow can be used (1) to provide efficient (e.g. uniform) cell and bead loading in the flowcell; (2) to eliminate flow-through of beads and cell buffers that are loaded to the flowcell, which increases the cell and bead capture efficiency of the flowcell; and/or (3) to enable agitation of small particles at the microwell surface, which may eliminate bead doublets.

For laminar flow, the relative velocity profile can be parabolic. The maximum flow velocity occurs at, or close to, the center of the fluidic channel. The flow velocity can be low or approach zero at the fluidic channel boundaries (also referred to as the flowcell boundaries), the boundaries between the flow and surfaces of the fluidic channel such as the fluidic channel bottom and sidewalls. The low flow velocity at the fluidic channel boundaries may result in low or minimal agitation of beads or cells at the surface of the microwell array or the substrate comprising the microwells.

In some embodiments, with plug flow, the relative flow velocity can be constant across the cross-section of the fluidic channel. Plug flow can enable agitation of beads or cells at the surface of the microwell array or the substrate comprising the microwells. With such agitation of beads or cells, each microwell can include one bead and/or one cell. However, non-uniform displacement of a gas such as air, $CO_2$, or $N_2$ at the fluidic channel boundaries can result in non-uniform plug flow, with relative flow velocity approaching zero at the fluidic channel boundaries.

A hydrophilic coating or superhydrophilic coating or treatment of the top wall (also referred to as ceiling, fluidic channel ceiling, or fluidic channel ceiling) within the fluidic channel of a flowcell can be used to introduce gas plugs and buffer plugs to a flowcell with horizontal non-tilting workflow (i.e., without tilting the flowcell). The superhydrophilic coating provides capillary aided flow for a uniform fluid front of the gas and buffer plug without the use of buoyancy to achieve gas displacement by buffer or to achieve buffer displacement by the gas.

A hydrophilic or superhydrophilic surface can facilitate a uniform meniscus and movement of the fluid front at the buffer-gas interface, thus avoiding breakdown of the plug within the flowcell without the use of buoyancy. The use of hydrophilic or superhydrophilic coatings can enable plug flow within a flowcell with a horizontal workflow. With hydrophilic or superhydrophilic coatings, the speed of the flow at the boundaries between the flow and the fluidic channel bottom can be non-zero. The relative flow velocity across the cross section of the fluidic channel can be constant or approximately constant. In some embodiments, the plug flow can be approximately horizontal plug flow. The horizontal plug flow can be capillary aided horizontal plug flow. In some embodiments, the plug flow may not depend on buoyancy of the gas. The plug flow may not depend on tilting of the device. The plug flow can be at a buffer-gas interface or other forms of plug flow, such as oil-water plug flow.

Coating Offset

Figure 6B:
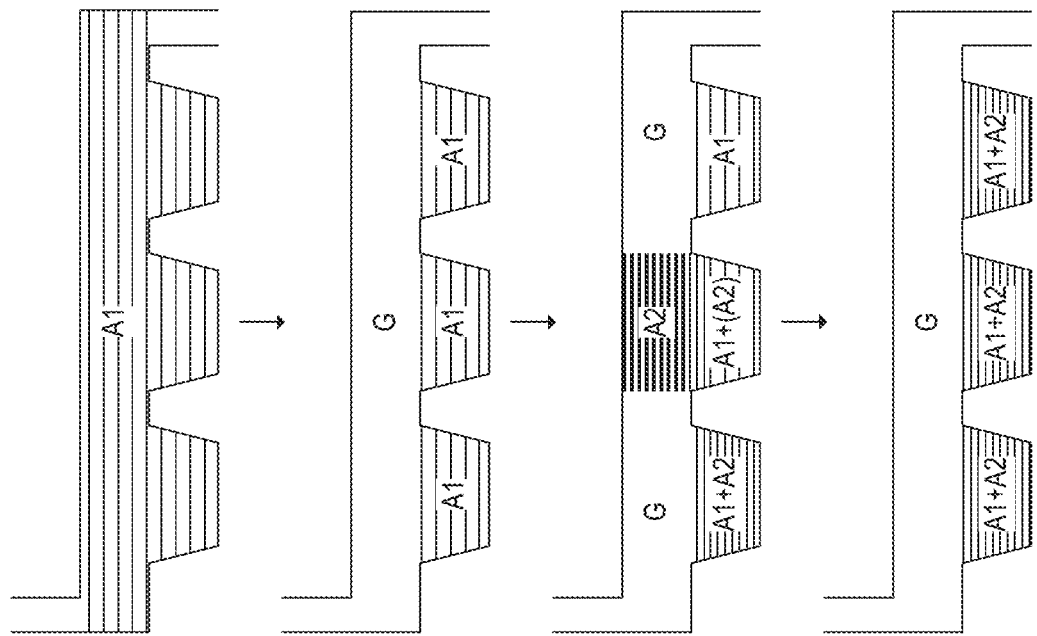
FIGS. 6A-6D depict non-limiting exemplary workflows for co-injection of a first fluid and a second fluid into a flowcell.

In some embodiments, hydrophilic and hydrophobic coatings can be used on a fluidic channel ceiling or a fluidic channel ceiling to tailor the profile of a gas-buffer fluid front in a flowcell. The selective coating (also referred to herein as functionalization) of the fluidic channel boundaries (also referred to herein as the flowcell boundaries) influences the direction of capillary flow within specific portions of the flowcell to control the profile of the gas-buffer fluid front profile. FIG. 6B is a schematic illustration showing directions of capillary flow and pressure-driven flow when the fluidic channel ceiling, except the edge of the fluidic channel ceiling, is coated with a hydrophilic coating. In some embodiments, the hydrophilic coating is offset from the fluidic channel boundaries (one or more edges formed by the fluidic channel ceiling and the sidewalls). The offset results in the fluidic channel ceiling at the fluidic channel boundaries not coated with a hydrophilic coating (also referred to as functionalized with a hydrophobic material). The remainder of the fluidic channel ceiling can be functionalized with a hydrophilic or a superhydrophilic material. As a result of the hydrophobic property of the fluidic channel ceiling at the edge of the fluidic channel ceiling, the capillary flow may be reduced or reversed in this region. As a result, the profile of the gas-buffer interface is modified, and the expansion of the gas plug near the fluidic channel boundaries may be no longer orthogonal to the edge.

The buffers used can be different in different implementations. In some embodiments, the buffer can be hydrophilic. For buffer-gas plug flow, the edge of the ceiling can be functionalized with a hydrophobic coating and the remainder can be functionalized with a hydrophilic coating. In some embodiments, the buffer can be hydrophobic rather than hydrophilic. For buffer-gas plug flow, the edge of the ceiling can be functionalized with a hydrophilic coating and the remainder can be functionalized with a hydrophobic coating. Other flowcell boundaries, for example the sidewalls or the bottom, can be similarly functionalized.

Cartridges

In some embodiments, the microwell array and the flowcell, can be packaged within a consumable cartridge that provides for convenient interfacing with the rest of the fluid handling system. The flowcell can facilitate the exchange of fluids, e.g. cell and bead suspensions, lysis buffers, rinse buffers, etc., that are delivered to the microwells. In some embodiments, the flow cell may be designed to facilitate efficient (e.g., uniform) distribution of cells and beads across the plurality of microwells. Design features may include: (i) one or more inlet ports for introducing cell samples, bead suspensions, or other assay reagents, (ii) one or more microwell chambers designed to provide for efficient (e.g., uniform) filling and efficient fluid-exchange while minimizing back eddies or dead zones, and (iii) one or more outlet ports for delivery of fluids to a sample collection point or a waste reservoir. In some embodiments, the design of the flow cell may include a plurality of microwell chambers that interface with a plurality of microwell arrays on a single substrate, or with a plurality of microwell array substrates, such that one or more different cell samples may be processed in parallel. In some embodiments, the design of the flow cell, e.g. the layout of the fluidic channels and chambers, may be adjusted so that different patterns of microwells (i.e. configurable microarray patterns) are accessed by fluids in a given design.

Figure 4:
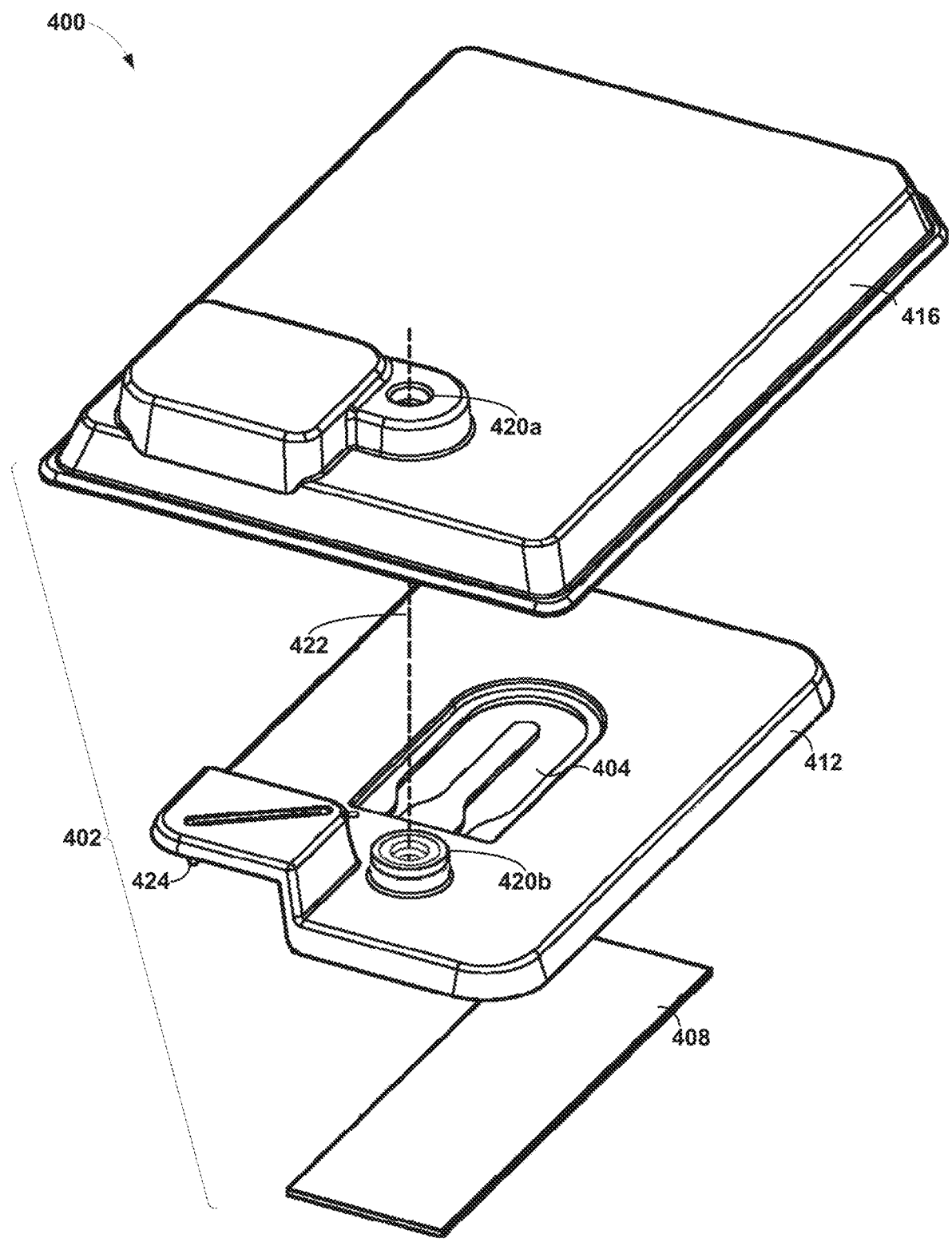
FIG. 4 shows an exploded view of an exemplary cartridge for barcoding.

In some embodiments, the flowcell can be part of the cartridge. FIG. 4 shows an exploded view of an exemplary cartridge 400 for barcoding. The cartridge 400 can include a flowcell 402 with a fluidic channel 704 formed by a microwell array substrate 408, a fluidic channel layer 412, and a cover plate 416. The number of layers forming the flowcell 400 can be different in different implementations, ranging from 1 to 20. In some embodiments, the number of layers forming the flowcell 400 can be, or be about, 1, 2, 3, 4, 5, 6, 7, 8, 9, 10, 11, 12, 13, 14, 15, 16, 17, 18, 19, 20, or a number or a range between any two of these values. In some embodiments, the number of layers forming the flowcell 400 can be at least, or at most, 1, 2, 3, 4, 5, 6, 7, 8, 9, 10, 11, 12, 13, 14, 15, 16, 17, 18, 19, 20. FIG. 4 shows that the cartridge 400 includes one inlet port, formed by inlet port components 420a and 420b on the cover plate 416 and the fluidic channel layer 412 respectively. The inlet port components 420a and 420b can be coaxial along the axis 422. The cartridge 400 includes one outlet port 424 on the fluidic channel layer 412. The locations of the outlet port can be different in different implementations. In some embodiments, the outlet port can be on the cover plate 416. In some embodiments the outlet port can be formed by outlet port components on the cover plate 416 and the fluidic channel layer 412.

The cartridge 400 or the flowcell 402 can include (i) one or more inlet ports for creating fluid connections with the instrument or manually introducing cell samples, bead suspensions, or other assay reagents into the cartridge. The flowcell can include one or more of (ii) one or more bypass channels, i.e. for self-metering of cell samples and bead suspensions, to avoid overfilling or back flow, (iii) one or more integrated microwell array/flowcell assemblies, or one or more chambers within which the microarray substrate(s) are positioned, (iv) integrated miniature pumps or other fluid actuation mechanisms for controlling fluid flow through the device, (v) integrated miniature valves (or other containment mechanisms) for compartmentalizing pre-loaded reagents (for example, bead suspensions) or controlling fluid flow through the device, (vi) one or more vents for providing an escape path for trapped gas, (vii) one or more sample and reagent waste reservoirs, (viii) one or more outlet ports for creating fluid connections with the instrument or providing a processed sample collection point. (ix) mechanical interface features for reproducibly positioning the removable, consumable cartridge with respect to the instrument system, and for providing access so that external magnets can be brought into close proximity with the microwell array, (x) integrated temperature control components or a thermal interface for providing good thermal contact with the instrument system, (xi) optical interface features, e.g. a transparent window, for use in optical interrogation of the microwell array, or any combination thereof.

The cartridge can be designed to process more than one sample in parallel. The cartridge can further comprise one or more removable sample collection chamber(s) that are suitable for interfacing with stand-alone PCR thermal cyclers or sequencing instruments. The cartridge itself can be suitable for interfacing with stand-alone PCR thermal cyclers or sequencing instruments. The term "cartridge" as used in this disclosure can be meant to include any assembly of parts which contains the sample and beads during performance of the assay.

The cartridge can further comprise components that are designed to create physical or chemical barriers that prevent diffusion of (or increase path lengths and diffusion times for) large molecules in order to minimize cross-contamination between microwells. Examples of such barriers can include, but are not limited to, a pattern of serpentine channels used for delivery of cells and solid supports (e.g., beads) to the microwell array, a retractable platen or deformable membrane that is pressed into contact with the surface of the microwell array substrate during lysis or incubation steps, the use of larger beads, e.g. Sephadex beads as described previously, to block the openings of the microwells, or the release of an immiscible, hydrophobic fluid from a reservoir within the cartridge during lysis or incubation steps, to effectively separate and compartmentalize each microwell in the array.

Cartridges can be fabricated using a variety of techniques and materials known to those of skill in the art. In general, the cartridges will be fabricated as a series of separate component parts and subsequently assembled using any of a number of mechanical assemblies or bonding techniques. Examples of suitable fabrication techniques include, but are not limited to, conventional machining, CNC machining, injection molding, thermoforming, and 3D printing. Once the cartridge components have been fabricated they can be mechanically assembled using screws, clips, and the like, or permanently bonded using any of a variety of techniques (depending on the choice of materials used), for example, through the use of thermal bonding/welding or any of a variety of adhesives or adhesive films, including epoxy-based, acrylic-based, silicone-based, UV curable, polyurethane-based, or cyanoacrylate-based adhesives.

Cartridge components can be fabricated using any of a number of suitable materials, including but not limited to silicon, fused-silica, glass, any of a variety of polymers, e.g. polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, non-stick materials such as teflon (PTFE), metals (e.g. aluminum, stainless steel, copper, nickel, chromium, and titanium), or any combination thereof.

The inlet and outlet features of the cartridge can be designed to provide convenient and leak-proof fluid connections with the instrument, or can serve as open reservoirs for manual pipetting of samples and reagents into or out of the cartridge. Examples of convenient mechanical designs for the inlet and outlet port connectors can include, but are not limited to, threaded connectors, Luer lock connectors, Luer slip or "slip tip" connectors, press fit connectors, and the like. The inlet and outlet ports of the cartridge can further comprise caps, spring-loaded covers or closures, or polymer membranes that can be opened or punctured when the cartridge is positioned in the instrument, and which serve to prevent contamination of internal cartridge surfaces during storage or which prevent fluids from spilling when the cartridge is removed from the instrument. The one or more outlet ports of the cartridge can further comprise a removable sample collection chamber that is suitable for interfacing with stand-alone PCR thermal cyclers or sequencing instruments.

In some embodiments, the inlet port and the outlet port can be capable of directing a flow of a fluid through the fluidic channel, thereby contacting the microwells with the fluid. In some embodiments, the device comprises a pipette tip interface for loading or removing a cell sample, an assay reagent, a bead suspension, waste from the device, or a combination thereof. The device can comprise the cell sample, the assay reagent, the bead suspension, or a combination thereof.

The cartridge can include integrated miniature pumps or other fluid actuation mechanisms for control of fluid flow through the device. Examples of suitable miniature pumps or fluid actuation mechanisms can include, but are not limited to, electromechanically- or pneumatically-actuated miniature syringe or plunger mechanisms, membrane diaphragm pumps actuated pneumatically or by an external piston, pneumatically-actuated reagent pouches or bladders, or electro-osmotic pumps.

The cartridge can include miniature valves for compartmentalizing pre-loaded reagents or controlling fluid flow through the device. Examples of suitable miniature valves can include, but are not limited to, one-shot "valves" fabricated using wax or polymer plugs that can be melted or dissolved, or polymer membranes that can be punctured; pinch valves constructed using a deformable membrane and pneumatic, magnetic, electromagnetic, or electromechanical (solenoid) actuation, one-way valves constructed using deformable membrane flaps, and miniature gate valves.

The cartridge can include vents for providing an escape path for trapped air or gas such as $CO_2$ or $N_2$. Vents can be constructed according to a variety of techniques, for example, using a porous plug of polydimethylsiloxane (PDMS) or other hydrophobic material that allows for capillary wicking of air or gas but blocks penetration by water.

The mechanical interface features of the cartridge can provide for easily removable but highly precise and repeatable positioning of the cartridge relative to the instrument system. Suitable mechanical interface features can include, but are not limited to, alignment pins, alignment guides, mechanical stops, and the like. The mechanical design features can include relief features for bringing external apparatus, e.g. magnets or optical components, into close proximity with the microwell array chamber.

The cartridge can include temperature control components or thermal interface features for mating to external temperature control modules. Examples of suitable temperature control elements can include, but are not limited to, resistive heating elements, miniature infrared-emitting light sources, Peltier heating or cooling devices, heat sinks, thermistors, thermocouples, and the like. Thermal interface features can be fabricated from materials that are good thermal conductors (e.g. copper, gold, silver, etc.) and can comprise one or more flat surfaces capable of making good thermal contact with external heating blocks or cooling blocks.

The cartridge can include optical interface features for use in optical imaging or spectroscopic interrogation of the microwell array. The cartridge can include an optically transparent window, e.g. the microwell substrate itself or the side of the flowcell or microarray chamber that is opposite the microwell array, fabricated from a material that meets the spectral requirements for the imaging or spectroscopic technique used to probe the microwell array. Examples of suitable optical window materials can include, but are not limited to, glass, fused-silica, polymethylmethacrylate (PMMA), polycarbonate (PC), cyclic olefin polymers (COP), or cyclic olefin copolymers (COC).

Instrument Modules & Systems

In some embodiments, instrument modules and systems for use in the automation of multiplexed, single cell stochastic labeling or molecular barcoding assays are provided. In some embodiments, these instruments may provide control and analysis functionality such as (i) fluidics control, (ii) cell or bead distribution and collection mechanisms, (iii) cell lysis mechanisms, (iv) magnetic field control, (v) temperature control, (vi) imaging capability, (vii) image processing, or any combination thereof. In some embodiments, the instrument system may comprise one or more modules, where each module provides one or more specific functional feature sets to the system. In other embodiments, the instrument system may be packaged such that all system functionality resides within one or more packages or within the same package. In some embodiments, the system may comprise additional functional units, either as integrated components or as modular components of the system, that expand the functional capabilities of the system to include PCR amplification (or other types of oligonucleotide amplification techniques) and oligonucleotide sequencing.

In some embodiments, the user pipettes a cell sample into the inlet port or sample well of a removable cartridge that is preloaded with all other assay reagents, inserts the cartridge into the instrument system for processing, and collects the output (e.g. a bead suspension comprising libraries of labeled oligonucleotides) from an outlet port or well of the cartridge. The instrument system can automate the assay steps, including distribution of cells into the microwells, distribution of beads from an onboard reagent well (if not already pre-loaded into the microwells), rinse steps, cell lysis steps, hybridization steps for RNA or DNA targets, and magnet-assisted bead retrieval. In some embodiments, the instrument system further comprises imaging and analysis capability, and real-time feedback and control of some assay steps, for example cell and bead distribution steps to ensure optimal coverage of the microwell pattern while minimizing the number of wells that contain more than one cell or more than one bead. In some embodiments, the instrument system includes an embedded computer or processor (although a peripheral computer or processor may be used in some embodiments) that runs software for controlling and coordinating the activities of imaging, motion control, magnetic control, fluidics control (e.g. application of pressure or vacuum to fluid lines), and other functional subsystems.

Fluidics

The instrument system can provide fluidics capability for delivering samples or reagents to the one or more microwell chamber(s) or flow cell(s) within one or more assay cartridge(s) connected to the system. Assay reagents and buffers may be stored in bottles, reagent and buffer cartridges, or other suitable containers that are connected to the cartridge inlets. In some embodiments, assay reagents and buffers may be pre-loaded and stored in reservoirs located within the cartridge itself. The system can include processed sample and waste reservoirs in the form of bottles, cartridges, or other suitable containers for collecting fluids downstream of the assay cartridge(s). In some embodiments, processed samples and waste fluids may be collected in reservoirs located within the cartridge itself. In some embodiments, the fluidics module may provide switching of flow between different sources, e.g. sample or reagent reservoirs located on the cartridge, or reagent bottles located in the instrument, and the microwell chamber inlet(s). In some embodiments, the fluidics module provides for contacting the cells in the array with an activating agent, chemical stimulus, or test compound at a specified, adjustable time prior to performing cell lysis and downstream assay steps. In some embodiments, the fluidics module may provide switching of flow between the microwell chamber outlet(s) and different collection points, e.g. processed sample reservoirs located within the cartridge, waste reservoirs located within the cartridge, or waste bottles located within the instrument.

Flow Control Using Pumps & Valves:

In some embodiments, control of fluid flow through the system will typically is performed through the use of pumps (or other fluid actuation mechanisms) and valves. Examples of suitable pumps include, but are not limited to, syringe pumps, programmable syringe pumps, peristaltic pumps, diaphragm pumps, and the like. In some embodiments, fluid flow through the system may be controlled by means of applying positive pneumatic pressure at the one or more inlets of the reagent and buffer containers, or at the inlets of the assay cartridge(s). In some embodiments, fluid flow through the system may be controlled by means of drawing a vacuum at the one or more outlets of the waste reservoirs, or at the outlets of the assay cartridge(s). Examples of suitable valves include, but are not limited to, check valves, electromechanical two-way or three-way valves, pneumatic two-way and three-way valves, and the like.

Fluid Flow Modes:

Different modes of fluid flow control may be utilized at different points in the assay procedure, e.g. forward flow (relative to the inlet and outlet for a given microwell chamber), reverse flow, oscillating or pulsatile flow, or combinations thereof, may all be used. In some embodiments, oscillating or pulsatile flow may be used, for example, during microwell loading steps to facilitate uniform distribution of cells and beads. In some embodiments, oscillating or pulsatile flow may be applied during assay wash/rinse steps to facilitate complete and efficient exchange of fluids within the one or more microwell flow cell(s) or chamber(s).

Different fluid flow rates may be utilized at different points in the assay process workflow, for example, in some embodiments of the disclosed instrument modules and system, the volumetric flow rate may vary from −100 ml/sec to +100 ml/sec. In some embodiment, the absolute value of the volumetric flow rate may be at least 0.001 ml/sec, at least 0.01 ml/sec, at least 0.1 ml/sec, at least 1 ml/sec, at least 10 ml/sec, or at least 100 ml/sec. In some embodiments, the absolute value of the volumetric flow rate may be at most 100 ml/sec, at most 10 ml/sec, at most 1 ml/sec, at most 0.1 ml/sec, at most 0.01 ml/sec, or at most 0.001 ml/sec. The volumetric flow rate at a given point in time may have any value within this range, e.g. a forward flow rate of 2.5 ml/sec, a reverse flow rate of −0.05 ml/sec, or a value of 0 ml/sec (i.e. stopped flow).

Air Injection:

In some embodiments of the fluidics system, it may be advantageous to insert injections of air between injections of solution when changing from one solution to another, e.g. between priming of the flow cell and injection of a cell suspension, or between a rinse buffer step and injection of a bead suspension. Potential advantages of this approach include reduced dispersion (by eliminating liquid/liquid interfaces), and reduced sample and reagent consumption (less fluid volume required to fill or empty the flow cell).

In some embodiments, air can be injected into the flow cell itself (e.g., comprising the fluidic layer). In some embodiments, air can be injected into the space in the flow cell above the microwell array (e.g., a microwell chamber). In some embodiments, injection of air may not substantially remove the contents of the microwells in the microwell array. In some embodiments, injection of air may remove at most 1, 2, 3, 4, 5, 6, 7, 8, 9, or 10% or more of the contents of the microwells of the microwell array.

Injection of air may be used to create a uniform environment for subsequent injections (e.g., loading) of liquids (e.g., comprising a cell or bead suspension). In some embodiments, loading of liquids after air injection can be at least 10, 20, 30, 40, 50, 60, 70, 80, 90 or 100% more uniformly dispersed than loading without prior air injection. In some embodiments, loading of liquids after air injection can be at most 10, 20, 30, 40, 50, 60, 70, 80, 90 or 100% more uniformly dispersed than loading without prior air injection.

Injection of air can reduce the dead volume (or dead space) in the flow cell and/or microwell array. In some embodiments, dead volume can be reduced with injection or air by at least 10, 20, 30, 40, 50, 60, 70, 80, 90 or 100%. In some embodiments, dead volume can be reduced with injection or air by at most 10, 20, 30, 40, 50, 60, 70, 80, 90 or 100%.

In some embodiments, injection of air may be performed using an automated pipette, a syringe pump, or the like. In some embodiments, injection of air may be performed at a rate ranging between 0.08 ml per second to 1.8 ml per second. In some embodiments, the rate of air injection is at least 0.08 ml per second, at least 0.1 ml per second, at least 0.2 ml per second, at least 0.3 ml per second, at least 0.4 ml per second, at least 0.5 ml per second, at least 0.6 ml per second, at least 0.7 ml per second, at least 0.8 ml per second, at least 0.9 ml per second, at least 1.0 ml per second, at least 1.2 ml per second, at least 1.4 ml per second, at least 1.6 ml per second, or at least 1.8 ml per second. In some embodiments, the rate of air injection is at most 1.8 ml per second, at most 1.6 ml per second, at most 1.4 ml per second, at most 1.2 ml per second, at most 1.0 ml per second, at most 0.8 ml per second, at most 0.6 ml per second, at most 0.4 ml per second, at most 0.2 ml per second, at most 0.1 ml per second, or at most 0.08 ml per second. Those of skill in the art will recognize that the rate of air injection may have any value within this range, e.g. about 1.25 ml per second. In some instances, the injection rate is about 0.36 ml per second.

In some embodiments, the pressure of injection of air may be between 0.01 and 0.25 atm. In some embodiments, the rate of air injection is at least 0.01 atm, at least 0.05 atm, at least 0.10 atm, at least 0.15 atm, at least 0.2 atm, or at least 0.25 atm. In some embodiments, the rate of air injection is at most 0.25 atm, at most 0.2 atm, at most 0.15 atm, at most 0.1 atm, at most 0.05 atm, or at most 0.01 atm. Those of skill in the art will recognize that the pressure of air injection may have any value within this range, e.g. about 0.11 atm.

Cell and Bead Distribution Mechanisms

In some embodiments the instrument system may include mechanisms for distributing and further facilitating the uniform distribution of cells and beads over the plurality of microwells. Examples of such mechanisms include, but are not limited to, magnetic transport, rocking, shaking, swirling, recirculating flow, oscillatory or pulsatile flow, low frequency agitation (for example, through pulsing of a flexible (e.g. silicone) membrane that forms a wall of the chamber or nearby fluidic channel), or high frequency agitation (for example, through the use of piezoelectric transducers). In some embodiments, one or more of these mechanisms is utilized in combination with physical structures or features on the interior walls of the flow cell or microwell chamber, e.g. mezzanine/top hat structures, chevrons, or ridge arrays, to facilitate mixing or to help prevent pooling of cells or beads within the array chamber. Flow-enhancing ribs on upper or lower surfaces of the flow cell or microwell chamber may be used to control flow velocity profiles and reduce shear across the microwell openings (i.e. to prevent cells or beads from being pulled out of the microwells during reagent exchange and rinse steps.

Magnetic Field-Assisted Bead Transport & Manipulation

In some embodiments, cells or beads may be distributed among the microwells, removed from the microwells, or otherwise transported through a flow cell or cartridge of an instrument system by using magnetic beads (e.g. conjugated to antibodies directed against cell surface markers, or as solid supports for libraries of stochastic labels) and externally-applied magnetic field gradients. In some embodiments, for example when using magnetic fields to trap magnetic beads in microwells or to elute magnetic beads from microwells, an externally-applied magnetic field gradient may be applied to the entire microwell pattern simultaneously. In some embodiments, an externally-applied magnetic field gradient may be applied to a selected area of the microwell pattern. In some embodiments, an externally-applied magnetic field gradient may be applied to a single microwell. In some embodiments, permanent magnets may be used to apply time-varying magnetic field gradients by moving the position of one or more permanent magnets relative to the microwell array or vice versa. In these embodiments, the velocity of the relative motion may be adjusted to so that the time-dependence of the magnetic field gradient is matched to the timescale on which magnetic beads undergo magnetophoresis into or out of microwells. In some embodiment, time-varying magnetic fields may be provided by varying the current applied to one or more electromagnets. In some embodiments, a combination of one or more permanent magnets and one or more electromagnets may be used to provide magnetic field gradients for transporting magnetic beads into microwells, out of microwells, or through the device. In some embodiments, cells or beads may be distributed among the microwells, removed from the microwells, or otherwise transported through a flow cell or cartridge of an instrument system by means of centrifugation or other non-magnetic means.

In some embodiments, beads (solid supports) may be removed from the microwells using one or more magnetic fields. In some embodiments, beads may be removed after lysis of cells in the microwells and/or attachment of nucleic acids to the pluralities of oligonucleotides immobilized on the individual beads. A magnet can be place on top of the cartridge and beads may be removed from the wells using the resultant magnetic field. In some embodiments, at least 70%, at least 75%, at least 80%, at least 85%, at least 90%, at least 95%, or at least 100% of the beads may be removed. In some embodiments, at most 70%, at most 75%, at most 80%, at most 85%, at most 90%, at most 95%, or at most 100% of the beads may be removed.

Real-Time Imaging & Feedback

In some embodiments, an imaging system and real-time image processing and analysis is used to monitor the cell and bead distribution processes (i.e. the distribution of cells and/or beads within the plurality of microwells) and feedback is used to adjust process steps accordingly, e.g. by prolonging or repeating some steps, by activating alternative cell or bead distribution mechanisms, and the like, in order to improve cell and/or bead distributions, or to achieve pre-specified target distributions.

Distribution of More than One Cell Type

In some embodiments, the system may include functionality for distributing more than one cell type over the microwell array. For example, the system may load the microwell array with a first cell type A, followed by rinsing and subsequent loading with a second cell type B, such that a plurality of microwells contain a single cell of type A and a single cell of type B. Such system functionality may be useful in studying cell-cell interactions and other applications. In general, the system may be configured to distribute at least one cell type, at least two cell types, at least three cell types, at least four cell types, or at least five cell types over the microwell array. In some embodiments, the system may be configured to distribute at most five cell types, at most four cell types, at most three cell types, at most two cell types, or at most one cell type over the microwell array. In some embodiments, the system may be configured to distribute complex mixtures of cells over the microwell array. In all of these configurations, the system may be set up to optimize the distribution of cells in microwells, and to identify wells having a greater or lesser number of cells than a specified number of cells, using cell distribution, real-time imaging, and feedback mechanisms as described above. In general, the percentage of microwells that contain more than one cell type, e.g. one cell each of types A and B, or one cell each from types A, B, and C, may range from about 1% to about 100%. In some embodiments, the percentage of microwells that contain more than one cell type may be at least 1%, at least 5%, at least 10%, at least 20%, at least 40%, at least 60%, at least 80%, or at least 90%. In other embodiments, the percentage of microwells that contain more than one cell type may be at most 100%, at most 90%, at most 80%, at most 60%, at most 40%, at most 20%, at most 10%, at most 5%, or at most 1%. In specific embodiment, the percentage of microwells that contain more than one cell type may have a value that falls anywhere within this range, e.g. about 8.5%.

Magnetic Field Control

Some embodiments of the disclosed methods utilize magnetic fields for removing beads from the microwells upon completion of the assay. In some embodiments, the instrument system may further comprise use of magnetic fields for transporting beads into or out of the microwell flow cell or chamber, or through other parts of the instrument system, or for retaining or trapping beads in particular locations after they have been loaded or distributed prior to the assay or during the assay. Examples of suitable means for providing control of magnetic fields include, but are not limited to, use of electromagnets in fixed position(s) relative to the cartridge, or the use of permanent magnets that are mechanically repositioned as necessary. In some embodiments of the instrument system, the strength of the applied magnetic field(s) will be varied by varying the amount of current applied to one or more electromagnets. In some embodiments of the instrument system, the strength of the applied magnetic fields will be varied by changing the position of one or more permanent magnets relative to the position of the microwell chamber(s) using, for example, stepper motor-driven linear actuators, servo motor-driven linear actuators, or cam shaft mechanisms. In other embodiments, the positions of magnets may be controlled in a linear (or non-linear) fashion, with speeds chosen to maximize bead collection efficiency, as opposed to performing transitions between just two fixed positions. In some embodiments of the instrument system, the use of pulsed magnetic fields may be advantageous, for example, to prevent clustering of magnetic beads.

In addition to consideration of the strength and location of magnetic fields for manipulating beads and other materials, it is important to design the system such that the magnetic field gradient is suitable for the task being performed. It is spatial gradients in magnetic field which exert translational force on magnetic materials and particles. Suitable gradients in fields can be achieved by the use of multiple magnets, the use of magnets or magnetized materials with particular edge and face geometries, and by designing magnets with appropriate spatial scale. Here, the term "magnets" refers to permanent magnets or electromagnets. Magnet assemblies comprising multiple magnetic domains, formed intrinsically or by design, may be used to generate magnetic fields with desirable field strengths and spatial variations. For example, patterns of small magnets with parallel or antiparallel field axes, or other relative angles, may be placed adjacent to the pattern of wells and fluidics, to achieve optimal trapping or manipulation of beads during the loading and operation of the device. In some embodiments of the disclosed systems, for example, when using magnetic fields to trap magnetic beads in microwells or to elute magnetic beads from microwells, an externally-applied magnetic field gradient may be applied to the entire microwell pattern simultaneously. In some embodiments, externally-applied magnetic field gradients may be applied to a selected area of the microwell pattern. In some embodiments, an externally-applied magnetic field gradient may be applied to a single microwell. In some embodiments, the magnetic field lines for an externally-applied magnetic field may lie at an angle relative to the plane of the microwell substrate of between about 30 degrees and 89 degrees. In some embodiments, the angle of the magnetic field lines relative to the plane of the microwell substrate may be between about 45 degrees and 80 degrees. In some embodiments, the angle of the magnetic field lines relative to the plane of the microwell substrate may be at least 45 degrees, at least 50 degrees, at least 55 degrees, at least 60 degrees, at least 65 degrees, at least 70 degrees, at least 75 degrees, or at least 80 degrees, or higher. In some embodiments, the angle of the magnetic field lines relative to the plane of the microwell substrate may be at most 80 degrees, at most 75 degrees, at most 70 degrees, at most 65 degrees, at most 60 degrees, at most 55 degrees, at most 50 degrees, or at most 45 degrees, or smaller. Those of skill in the art will recognize that the angle of the magnetic field lines relative to the plane of the microwell substrate may have any value within this range, for example, about 52 degrees.

Temperature Control

In some embodiments, the instrument system will include temperature control functionality for the purpose of facilitating the accuracy and reproducibility of assay results, for example, cooling of the microwell flow cell or chamber may be advantageous for minimizing molecular diffusion between microwells. Examples of temperature control components that may be incorporated into the instrument system (or cartridge) design include, but are not limited to, resistive heating elements, infrared light sources, Peltier heating or cooling devices, heat sinks, thermistors, thermocouples, and the like. In some embodiments of the system, the temperature controller may provide for a programmable temperature change at a specified, adjustable time prior to performing cell lysis and downstream assay steps. In some embodiments of the system, the temperature controller may provide for programmable changes in temperature over specified time intervals. In some embodiments, the temperature controller may further provide for cycling of temperatures between two or more set temperatures with specified frequency and ramp rates so that thermal cycling for amplification reactions may be performed.

Imaging Capability

In some embodiments instrument systems are provided including optical imaging or other spectroscopic capabilities. Such functionality may be useful, for example, for inspection of the microwell substrate to determine whether or not the microwell pattern has been uniformly and optimally populated with cells or beads. Any of a variety of imaging modes may be utilized, including but not limited to, bright-field, dark-field, fluorescence, luminescence, or phosphorescence imaging. The choice of imaging mode will impact the design of microwell arrays, flow cells, and cartridge chambers in that the microwell substrate or opposing wall of the flow cell or microwell chamber will necessarily need to be transparent over the spectral range of interest. In some embodiments, partially-coherent illumination light may be used to improve the contrast of unstained cells in bright-field images.

In some embodiments, quantitative phase imaging may be used to improve the performance of automated image processing and analysis software in determining the number of cells located in each microwell. Unstained cells typically absorb very little light, but cause measureable phase delays in transmitted light. Quantitative phase imaging can refer to any of several methods for calculating phase information from a series of two or more images (which capture intensity data) collected using coherent or partially-coherent light. A series of suitable intensity images may be captured, for example, by capturing images at different defocus distances. The images are then processed to recover phase information using, for example, using the "Transport of Intensity" algorithm or iterative techniques based on the Gerchberg-Saxton approach, to create a shape and density map of the cells in the field of view.

In some embodiments, each plurality of microwells may be imaged in its entirety within a single image. In some embodiments, a series of images may be "tiled" to create a high resolution image of the entire microwell pattern. In some embodiment, a single image that represents a subsection of the pattern may be used to evaluate properties, e.g. cell or bead distributions, for the pattern as a whole.

In some embodiments, dual wavelength excitation and emission (or multi-wavelength excitation or emission) imaging may be performed.

Light Sources

Any of a variety of light sources may be used to provide the imaging or excitation light, including but not limited to, tungsten lamps, tungsten-halogen lamps, arc lamps, lasers, light emitting diodes (LEDs), or laser diodes. In many embodiments, a combination of one or more light sources, and additional optical components, e.g. lenses, filters, apertures, diaphragms, mirrors, and the like, will comprise an illumination system (or sub-system).

Detectors

Any of a variety of image sensors may be used for imaging purposes, including but not limited to, photodiode arrays, charge-coupled device (CCD) cameras, or CMOS image sensors. Imaging sensors may be one-dimensional (linear) or two-dimensional array sensors. In many embodiments, a combination of one or more image sensors, and additional optical components, e.g. lenses, filters, apertures, diaphragms, mirrors, and the like, will comprise an imaging system (or sub-system).

Other Optical Components

The optical system will typically include a variety of optical components for steering, shaping, filtering, or focusing light beams through the system. Examples of suitable optical components include, but are not limited to, lenses, mirrors, prisms, diffraction gratings, colored glass filters, narrowband interference filters, broadband interference filters, dichroic reflectors, optical fibers, optical waveguides, and the like. In some embodiments, the imaging system will further comprise one or more translation stages or other motion control mechanisms for the purpose of moving the microwell substrate(s) relative to the illumination and/or imaging systems, or vice versa. In some embodiments, the instrument system may use an optically transparent microarray substrate as a waveguide for delivering excitation light to the microwells.

Complementary Assay Techniques

The choice of imaging mode may also enable the use of other types of assays to be run in parallel with stochastic labeling and molecular indexing assays, for example, the use of trypan blue live cell/dead cell assays with bright field imaging, the use of fluorescence-based live cell/dead cell assays with fluorescence imaging, etc. Correlation of viability data for individual cells with the cell tag associated with each bead in the associated microwell may provide an additional level of discrimination in analyzing the data from multiplexed, single cell assays.

Additional System Capabilities

In some embodiments, the system may comprise non-imaging or non-optical capabilities for probing the microwell array. Examples of non-imaging or non-optical techniques for detecting trapped air bubbles, determining the cell or bead distribution over the array, etc., include but are not limited to measurements of light scattering, ultraviolet/visible/infrared absorption measurements (e.g. using stained cells or beads that incorporate dyes), coherent Raman scattering, and conductance measurements (e.g. using microfabricated arrays of electrodes in register with microwell arrays). In some embodiments, information obtained about the condition or contents of particular wells may be used to determine that those wells must be sequestered, excised, or otherwise prevented from contributing to the assay results. For example, electrical heating elements may be used to form a bubble or denature the well contents, or optical energy may be applied to deform the walls of the well and thereby trap the contents, or a local magnetic field could be applied such that the bead to be eliminated is trapped in the substrate instead of eluted for analysis.

Interfaces with PCR Thermocyclers, Sequencers, & FACS Instruments

In some embodiments, the instrument systems of the present disclosure may further comprise interfaces with PCR thermocyclers, sequencers, cell sorters, fluorescence-activated cell sorter (FACS) instruments, or other types of lab automation equipment.

In some embodiments, an interface for PCR thermocyclers is provided such that instrument system outputs labeled oligonucleotide libraries directly into tubes, strips, or plates that are compatible with commercially-available PCR instruments, for example, the Roche LightCycler® series of real-time PCR instruments, and the like.

In some embodiments, an interface is provided for cell sorters or FACS instruments such that sorted cells are deposited directly into a microwell array or cartridge. The interface for FACS instruments may, for example, include both hardware and software components, where the software provides the capability for simultaneous control of the FACS instrument and the single cell, stochastic labeling or molecular barcoding system. In some embodiments, the software may provide analysis capability for identifying correlations between the FACS data (e.g. the presence or absence of specified cell surface markers) and the copy numbers for one or more genes in a specified sub-population of cells. FACS machines can be used to sort single cells directly into the microwell array of the disclosure.

In some embodiments, an interface with lab automation equipment in general is provided, for example, cartridges for use with the disclosed instrument systems may be configured to have inlet ports of the proper dimension and spacing such that samples and reagents may be dispensed directly into the cartridge using commercially-available pipetting stations and liquid-handling robotics. Similarly, in some embodiments, cartridges for use with the disclosed instrument systems may be configured to have dimensions that are compatible with commercially-available plate-handling robotics for automated storage, retrieval, or movement between other laboratory workstations.

System Processor and Software:

In some embodiments, instrument systems designed to support the automation of multiplexed, single cell stochastic labeling and molecular barcoding assays will include a processor or computer, along with software to provide (i) instrument control functionality, (ii) image processing and analysis capability, and (iii) data storage, analysis, and display functionality.

System Processor and Control Software:

In some embodiments, the instrument system will comprise a computer (or processor) and computer-readable media that includes code for providing a user interface as well as manual, semi-automated, or fully-automated control of all system functions, e.g. control of the fluidics system, the temperature control system, cell or bead distribution functions, magnetic bead manipulation functions, and the imaging system. In some embodiments, the system computer or processor may be an integrated component of the instrument system (e.g. a microprocessor or mother board embedded within the instrument). In some embodiments, the system computer or processor may be a stand-alone module, for example, a personal computer or laptop computer. Examples of fluid control functions provided by the instrument control software include, but are not limited to, volumetric fluid flow rates, fluid flow velocities, the timing and duration for sample and bead addition, reagent addition, and rinse steps. Examples of temperature control functions provided by the instrument control software include, but are not limited to, specifying temperature set point(s) and control of the timing, duration, and ramp rates for temperature changes. Examples of cell or bead distribution functions provided by the instrument control software include, but are not limited to, control of agitation parameters such as amplitude, frequency, and duration. Examples of magnetic field functions provided by the instrument control software include, but are not limited to, the timing and duration of the applied magnetic field(s), and in the case of electromagnets, the strength of the magnetic field as well. Examples of imaging system control functions provided by the instrument control software include, but are not limited to, autofocus capability, control of illumination or excitation light exposure times and intensities, control of image acquisition rate, exposure time, and data storage options.

Image Processing Software:

In some embodiments of the instrument system, the system will further comprise computer-readable media that includes code for providing image processing and analysis capability. Examples of image processing and analysis capability provided by the software include, but are not limited to, manual, semi-automated, or fully-automated image exposure adjustment (e.g. white balance, contrast adjustment, signal-averaging and other noise reduction capability, etc.), automated edge detection and object identification (i.e. for identifying cells and beads in the image), automated statistical analysis (i.e. for determining the number of cells or beads identified per microwell or per unit area of the microwell substrate, or for identifying wells that contain more than one cell or more than one bead), and manual measurement capabilities (e.g. for measuring distances between objects, etc.). In some embodiments, the instrument control and image processing/analysis software will be written as separate software modules. In some embodiments, the instrument control and image processing/analysis software will be incorporated into an integrated package.

In some embodiments, the system software may provide integrated real-time image analysis and instrument control, so that cells may be optically monitored and classified according to a pre-determined set of characteristics. Examples of cellular characteristics that may be optically monitored and used for classification purposes include, but are not limited to, cell size, cell shape, live cell/dead cell determination (e.g. using selectively absorbed chromophores such as Trypan blue, or fluorescent dyes such as calcein AM, ethidium homodimer-1, DiOC2(3), Di005(3), DiOC6(3), DiSC3(5), DiIC1(5), DiOC18(3), propidium iodide, SYBR® 14, SYTOX® Green, etc.), cells exhibiting a specified range of intracellular pH (e.g. using intracellular pH-sensitive fluorescent probes such as 2',7'-Bis-(2-carboxyethyl)-5-(and-6-)carboxyfluorescein (BCECF), 2',7'-bis-(2-carboxypropyl)-5-(and-6-)-carboxyfluorescein (BCPCF), etc.), cells exhibiting a specified range of membrane potential (e.g. using membrane potential-sensitive fluorophores such as FluoVolt™, di-3-ANEPPDHQ, Bis-(1, 3-Dibutylbarbituric Acid) Trimethine Oxonol (DiBAC4(3)), DiBAC4(5), DiSBAC2(3), Merocyanine 540, JC-1, JC-9, Oxonol V, Oxonol VI, Tetramethylrhodamine methyl and ethyl esters, Rhodamine 123, Di-4-ANEPPS, Di-8-ANEPPS, Di-2-ANEPEQ, Di-3-ANEPPDHQ, Di-4-ANEPPDHQ, etc.), cells exhibiting a specified level of intracellular calcium (e.g. using Ca2+-sensitive fluorescent dyes such as fura-2, indo-1, fluo-3, fluo-4, Calcium Green-1, Quin 2, etc.), cells exhibiting one or more specified cell surface markers (e.g. using fluorescently-labeled antibodies directed towards the cell surface markers), cells expressing fluorescent proteins (e.g. GFP, bilirubin-inducible fluorescent protein, UnaG, dsRed, eqFP611, Dronpa, TagRFPs, KFP, EosFP, Dendra, IrisFP, etc.), and the like. In many embodiments, two or more dyes, fluorophores, or other optical probes having non-overlapping spectral properties (e.g. non-overlapping excitation peaks, non-overlapping absorption or emission peaks, etc.) can be selected so that cells may be simultaneously characterized with respect to two or more properties. In some embodiments, real-time image processing and analysis is used to identify wells containing cells exhibiting one or more specified characteristics.

Applications

The methods, devices, and systems disclosed herein may be used for a variety of applications in basic research, biomedical research, environmental testing, and clinical diagnostics. Examples of potential applications for the disclosed technologies include, but are not limited to, genotyping, gene expression profiling, detection and identification of rare cells, diagnosis of a disease or condition, determining prognosis for a disease or condition, determining a course of treatment for a disease (e.g., determining if a patient may respond to a therapy) or condition, and monitoring the response to treatment for a disease or condition, and understanding biological development processes.

Cell Types

In some embodiments, the cells are normal cells, for example, human cells in different stages of development, or human cells from different organs or tissue types. In some embodiments, the cells are non-human cells, for example, other types of mammalian cells (e.g. mouse, rat, pig, dog, cow, or horse). In some embodiments, the cells are other types of animal or plant cells. In other embodiments, the cells can be any prokaryotic or eukaryotic cells. In some embodiments the cells are sorted prior to associating a cell with a bead. For example the cells can be sorted by fluorescence-activated cell sorting or magnetic-activated cell sorting, or more generally by flow cytometry. The cells can be filtered by size. In some embodiments a retentate contains the cells to be associated with the bead. In some embodiments the flow through contains the cells to be associated with the bead.

In some embodiments of the disclosed methods, devices, and systems, a first cell sample is obtained from a person not having a disease or condition, and a second cell sample is obtained from a person having the disease or condition. In some embodiments, the persons are different. In some embodiments, the persons are the same but cell samples are taken at different time points. In some embodiments, the persons are patients, and the cell samples are patient samples. In some embodiments, the disease or condition is a cancer, a bacterial infection, a viral infection, an inflammatory disease, a neurodegenerative disease, a fungal disease, a parasitic disease, a genetic disorder, or any combination thereof.

In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some instances, the cells are derived from a cancer but collected from a bodily fluid (e.g. circulating tumor cells). Non-limiting examples of cancers may include, adenoma, adenocarcinoma, squamous cell carcinoma, basal cell carcinoma, small cell carcinoma, large cell undifferentiated carcinoma, chondrosarcoma, and fibrosarcoma.

In some embodiments, the cells are cells that have been infected with virus and contain viral oligonucleotides. In some embodiments, the viral infection may be caused by a virus selected from the group consisting of double-stranded DNA viruses (e.g. adenoviruses, herpes viruses, pox viruses), single-stranded (+ strand or "sense") DNA viruses (e.g. parvoviruses), double-stranded RNA viruses (e.g. reoviruses), single-stranded (+ strand or sense) RNA viruses (e.g. picornaviruses, togaviruses), single-stranded (− strand or antisense) RNA viruses (e.g. orthomyxoviruses, rhabdoviruses), single-stranded ((+ strand or sense) RNA viruses with a DNA intermediate in their life-cycle) RNA-RT viruses (e.g. retroviruses), and double-stranded DNA-RT viruses (e.g. hepadnaviruses).

In some embodiments, the cells are bacteria. These may include either gram-positive or gram-negative bacteria. Examples of bacteria that may be analyzed using the disclosed methods, devices, and systems include, but are not limited to, Actinomedurae, *Actinomyces israelii*, *Bacillus anthracis*, *Bacillus cereus*, *Clostridium botulinum*, *Clostridium difficile*, *Clostridium perfringens*, *Clostridium tetani*, *Corynebacterium*, *Enterococcus faecalis*, *Listeria monocytogenes*, *Nocardia*, *Propionibacterium acnes*, *Staphylococcus aureus*, *Staphylococcus epiderm*, *Streptococcus mutans*, *Streptococcus pneumoniae* and the like. Gram negative bacteria include, but are not limited to, *Afipia felis*, *Bacteroides*, *Bartonella bacilliformis*, *Bortadella pertussis*, *Borrelia burgdorferi*, *Borrelia recurrentis*, *Brucella*, *Calymmatobacterium granulomatis*, *Campylobacter*, *Escherichia coli*, *Francisella tularensis*, *Gardnerella vaginalis*, *Haemophilius aegyptius*, *Haemophilius ducreyi*, *Haemophilius* influenziae, Heliobacter *pylori*, *Legionella pneumophila*, *Leptospira interrogans*, *Neisseria meningitidia*, *Porphyromonas gingivalis*, *Providencia sturti*, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis and the like. Other bacteria may include Myobacterium avium, Myobacterium leprae, Myobacterium tuberculosis, Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium, Meningococci and the like.

In some embodiments, the cells are fungi. Non-limiting examples of fungi that may be analyzed using the disclosed methods, devices, and systems include, but are not limited to, Aspergilli, Candidae, Candida albicans, Coccidioides immitis, Cryptococci, and combinations thereof.

In some embodiments, the cells are protozoans or other parasites. Examples of parasites to be analyzed using the methods, devices, and systems of the present disclosure include, but are not limited to, Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii, Trypanosomae, trapezoidal amoeba, worms (e.g., helminthes), particularly parasitic worms including, but not limited to, Nematoda (roundworms, e.g., whipworms, hookworms, pinworms, ascarids, filarids and the like), Cestoda (e.g., tapeworms).

Precise Delivery of Fluid Components

Disclosed herein include the use of a simultaneous injection of two fluids (e.g., two plugs) into a fluidic channel comprising microwells on the bottom of the fluidic channel allows precise control for the duration of exposure of the first fluid (e.g., an aqueous liquid, such as a lysis buffer) to the microwells, prior to sealing of the wells with the second fluid (e.g., a non-aqueous liquid, such as an oil, and a gas). In some embodiments, the first fluid has a high degree of phase separation with the second fluid that is injected to the flow channel after the first fluid. Additionally or alternatively, the microwells can include another fluid (e.g., a buffer) has a higher density than the first liquid.

Disclosed herein includes embodiments, of a system, a device, an apparatus, and a method for exposing partitions (e.g., microwells and droplets) to a liquid (e.g., an aqueous liquid, such as a buffer) for a precisely controlled duration. In some embodiments, the system, device, apparatus, and method can be used to control the lysis reaction of a cell in a microwell. In some embodiments, the precise control of the lysis reaction of a cell in a microwell can improve the performance of barcoding assays, such as the BD Rhapsody™ assay. In some embodiments, the system, device, apparatus, and method can be used to control the concentration of analytes inside a microwell, with variable concentrations along a path (e.g., the longitudinal path) of a flow or fluidic channel of a flow cell. The system, apparatus, device, and method can be utilized to investigate the effect of analyte concentrations on changing cell phenotype. Such an assay may be applicable for use in development of cell therapy treatment, for example, to determine the effect of viral vector concentration on cell phenotype. The system, apparatus, device, and method can enable tests on correlation between a large range of analyte concentrations and cell phenotype, on a single cell level and for large cell populations. Compatibility with the Rhapsody™ single cell analysis platform allows detection of phenotype changes in both RNA and protein expression.

Methods for determining mRNA expression profiles of single cells can be performed in a massively parallel manner. For example, the Precise™ assay can be used to determine the mRNA expression profiles of more than 10000 cells simultaneously. A substrate can comprise an array of microwells, wherein each microwell comprises a reaction chamber of defined volume that can entrap a single cell and a single solid support (e.g., a bead) comprising barcodes (e.g., stochastic barcodes). The lysis of the single cells and labeling of target nucleic acid molecules released from said cells can be performed in a massively parallel manner in said array of reaction chambers. However, cross-talk of proteins or RNA between microwells following cell lysis can the reduce signal-to-noise ratio and reduce the number of unique target molecules captured during the assay. There is a need for methods of delivering buffers (e.g., lysis buffers) to microwells for precise periods of time to allow for precise delivery of one or more components of said buffers (e.g., detergents, digestive enzymes). There is a need for methods of sealing and containing reactions initiated within microwells (e.g., cellular lysis) to reduce molecular cross-talk between microwells. Additionally, generating different concentration profiles of one or more analytes in the plurality of microwells can enable comprehensives correlation studies of said analytes (e.g., dose-dependent effect of an analyte on cell phenotype). The systems, devices, and methods disclosed herein can enable delivering variable amounts of an analyte to a plurality of microwells.

There are provided, in some embodiments, methods, systems, and devices for introducing one or more components into a fluid. The method can comprise co-injection of a first fluid and a second fluid. In some embodiments, the method comprises two fluids (e.g., a first buffer and a second buffer, a first plug and a second plug) aspirated sequentially and then dispensed together. In some embodiments, the first fluid and a second fluid are immiscible (e.g. an aqueous and non-aqueous buffer). In some embodiments, the second fluid is less dense than the first fluid. The duration in which the first fluid passes over (interfaces) with a surface of the content of the microwell in a microwell array can be controlled with high precision by precisely controlling of the flow rate and/or volume of the first fluid. In some embodiments, the methods disclosed herein enable delivery of precise amounts of one or more components of a first fluid to a microwell. The delivery of one or more components of the first fluid (e.g., lysis buffer components) can be controlled by adjusting the flow rate of the first fluid and/or the volume of the first fluid (thereby modulating the interface duration), the concentration of said one or more components in the first fluid, or any combination thereof. The flow rate of the first fluid can be uniform along the fluidic channel. In some such embodiments, uniform amounts of one or more components can be delivered to each of a plurality of microwells along the fluidic channel. The flow rate of the first fluid can be non-uniform along the fluidic channel. In some embodiments, the flow rate of the first fluid comprising one or more components (e.g., analytes) is dynamically varied along the longitudinal path of the flow channel. In some such embodiments, the resulting concentration of one or multiple analytes in the microwells along the longitudinal path of the flow channel is non-uniform. In some embodiments, methods of generating different concentration profiles of analytes within an array of microwells are provided. Methods of measuring a dose-dependent phenotypic effect of an agent on single on single cells are provided.

In some embodiments, methods of performing a reaction (e.g., a lysis reaction) are provided. The reaction can take place within a microwell chamber. The first fluid can comprise one or more components initiating the reaction. The second fluid can seal and contain the reaction. Phase separation between the contents of the microwell and the second fluid can contain the contents of the microwell. The reaction can comprise cell lysis in a microwell chamber containing a single cell and a single bead comprising a plurality of stochastic barcodes. The reaction can comprise labeling of nucleic acid target molecules with said stochastic barcodes. The methods disclosed herein can be compatible with single cell analysis platforms (e.g., BD Rhapsody™). The methods disclosed herein can improve the performance of single cell analysis platforms. In some embodiments, the application of the disclosed methods in said single cell analysis platforms yield improvements in RNA & protein expression profiling data (e.g., reduced signal-to-noise ratios, increased molecular label counts), by, for example, reducing cross-talk of molecules between microwells during cellular lysis. In some embodiments, the duration in which lysis buffer interfaces with microwells (e.g., the interface duration) is: i) long enough to enable diffusion of a sufficient amount of lysis buffer from the fluidic channel into the microwell such that final lysis buffer concentration in microwells is sufficient to lyse cells; and/or ii) short enough to prevent cell contents from diffusing out of the microwell before, during, and/or after cell lysis.

Disclosed herein include systems, apparatuses, devices, and methods for introducing one or more components to contents of microwells. In some embodiments, the method comprises: (a) introducing a first fluid into a fluidic channel comprising a ceiling, a first sidewall, and a bottom, wherein the bottom of the fluidic channel comprises a plurality of microwells, and wherein the ceiling, the first sidewall, and the bottom of the fluidic channel surround a fluidic channel volume of the fluidic channel excluding the volume of each of the plurality of microwells (e.g., above the microwells), whereby the fluidic channel volume and each microwell of the plurality of microwells comprise the first fluid; (b) introducing a first displacement fluid into the fluidic channel to displace the first fluid from the fluidic channel volume at a first flow rate; (c) introducing a second fluid, immediately followed by and/or simultaneously with, a second displacement fluid, into the fluidic channel at a second flow rate, wherein one or more components of the second fluid enters the content in the microwell when the second fluid comes into contact with the content in the microwell for a first duration, and wherein the second displacement fluid displaces the second fluid from the fluidic channel volume and/or seals the content of the microwell.

Disclosed herein include methods for introducing one or more components. In some embodiments, the method comprises: (a) providing a fluidic channel comprising a ceiling, a first sidewall, and a bottom, wherein the bottom of the fluidic channel comprises a plurality of microwells comprising a first fluid, wherein the ceiling, the first sidewall, and the bottom of the fluidic channel surround a fluidic channel volume of the fluidic channel excluding the volume of each of the plurality of microwells (above the microwells), and wherein the fluidic channel volume lacks the first fluid; (b) introducing a plurality of second fluids, each immediately followed by and/or simultaneously with a second displacement fluid, into the fluidic channel at a second flow rate, wherein one or more components of each of the plurality of second fluids enters the content in the microwell when the second fluid comes into contact with the content in the microwell for a first duration, and wherein the second displacement fluid displaces the second fluid from the fluidic channel volume and/or seals the content of the microwell.

There are provided, in some embodiments, methods for introducing one or more components into a fluid. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; (b) priming the flowcell with a priming fluid; (c) displacing the priming fluid from the volume of the fluidic channel above the plurality microwells, whereby the content of each microwell of plurality of microwells comprises the priming fluid; and (d) co-injecting a first fluid and a second fluid into the fluidic channel, wherein the first fluid is introduced into the fluidic channel immediately before the second fluid, wherein one or more components of the first fluid enters the content of the microwell, and wherein the second fluid seals the content of the microwell. In some embodiments, the first fluid interfaces with a surface of the content of the microwell for a duration. The one or more components of the first fluid can enter the microwell by diffusion. During the duration when the first fluid interfaces with the surface of the microwell, the one or more components can initiate a reaction in the content of the microwell. In some embodiments, after the first fluid interfaces with the surface of the microwell, the one or more components initiates a reaction in the content of the microwell.

There are provided, in some embodiments, methods of performing a reaction. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; and (b) co-injecting a first fluid and a second fluid into the fluidic channel, wherein the first fluid is introduced into the fluidic channel immediately before the second fluid, wherein the first fluid interfaces with a surface of a microwell for a duration, wherein one or more components of the first fluid enters the content of the microwell, wherein the one or more components initiates a reaction in the content of the microwell, and wherein the second fluid seals the content of the microwell.

There are provided, in some embodiments, methods of delivering varying concentrations of an analyte to a plurality of microwells. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; and (b) co-injecting a first fluid and a second fluid into the fluidic channel, wherein the first fluid is introduced into the fluidic channel immediately before the second fluid, wherein the first fluid interfaces with a surface of the content of the microwell for a duration, wherein the first fluid comprises one or more components, wherein the one or more components of the first fluid comprise an analyte, wherein the flow rate of the first fluid is not uniform along the longitudinal path of the fluidic channel, wherein the analyte enters the content of the microwell, wherein the final concentration of the analyte in the microwell is unequal for at least two microwells of the plurality of microwells, and wherein the second fluid seals the content of the microwell.

In some embodiments, during the duration when the first fluid interfaces with the surface of the microwell, the one or more components initiates a reaction in the content of the microwell. In some embodiments, the method comprises, prior to the co-injecting, priming the flowcell with a priming fluid. In some embodiments, the method comprises, prior to the co-injecting, displacing the priming fluid from the volume of the fluidic channel (above the plurality microwells). The volume of the first fluid can be at most 10% (e.g., 1%, 2%, 3%, 5%, 7%, 9%, 10%, and overlapping rangers therein) of the volume of the second fluid.

Following the co-injecting, the fluidic channel above the plurality microwells can comprise the second fluid. In some embodiments, following the co-injecting, the volume of the fluidic channel above the plurality microwells does not comprise the first fluid. Displacing the priming fluid from the volume of the fluidic channel above the plurality microwells can comprise injection of a displacing fluid into the fluidic channel. The displacing fluid can be a gas or a non-aqueous liquid. In some embodiments, the priming fluid can be a first aqueous liquid or a first non-aqueous liquid. The microwell can comprise an initial microwell fluid prior to the co-injecting. The initial microwell fluid can comprise the priming fluid. In some embodiments, the initial microwell fluid is an aqueous liquid. In some embodiments, the initial microwell fluid is an aqueous buffer. In some embodiments, the initial microwell fluid is a non-aqueous liquid. The one or more components of the first fluid can comprise an analyte. The first fluid can comprise a known or unknown concentration of an analyte. The one or more components of the first fluid can comprise an analyte, a buffer component, a small molecule, a biomolecule, a reagent, an agent, or any combination thereof. Injection of a fluid (e.g., a first fluid, a second fluid, a displacing fluid) can displace at least about 90% (e.g., 90%, 91%, 92%, 93%, 94%, 95%, 96%, 97%, 98%, 99%, or 100%, or overlapping ranges therein) of the pre-existing fluid of the volume of the fluidic channel above the plurality microwells.

Figure 5A:
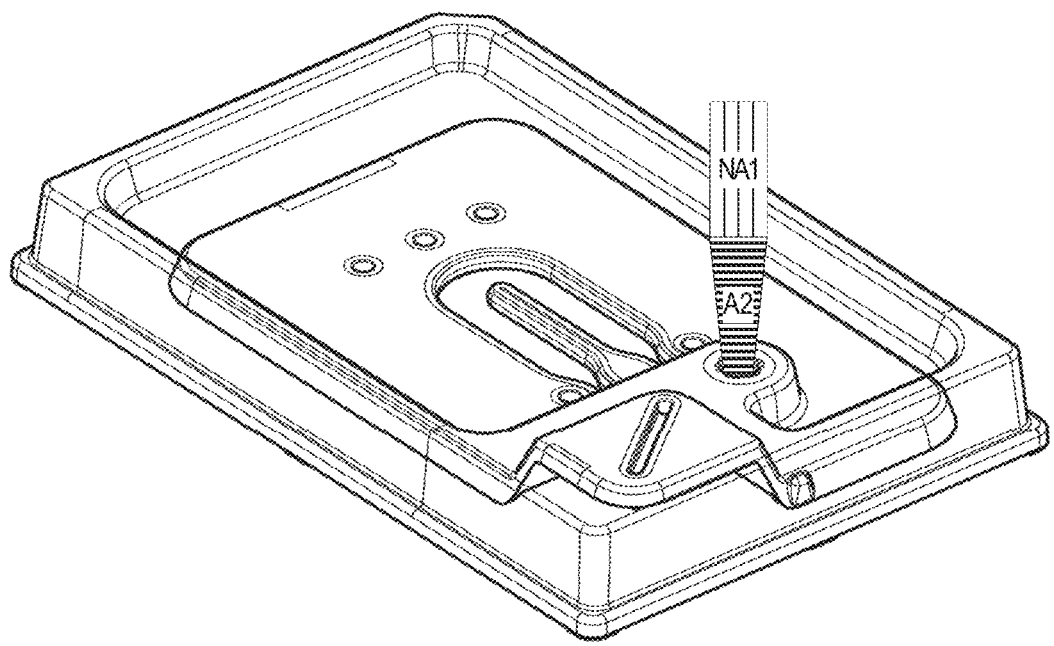
FIG. 5A shows an exemplary pipette comprising an aqueous liquid ("A2") and a non-aqueous liquid ("NA") positioned at the pipette tip interface of the inlet port of an exemplary cartridge prior to co-injection.
Figure 5B:
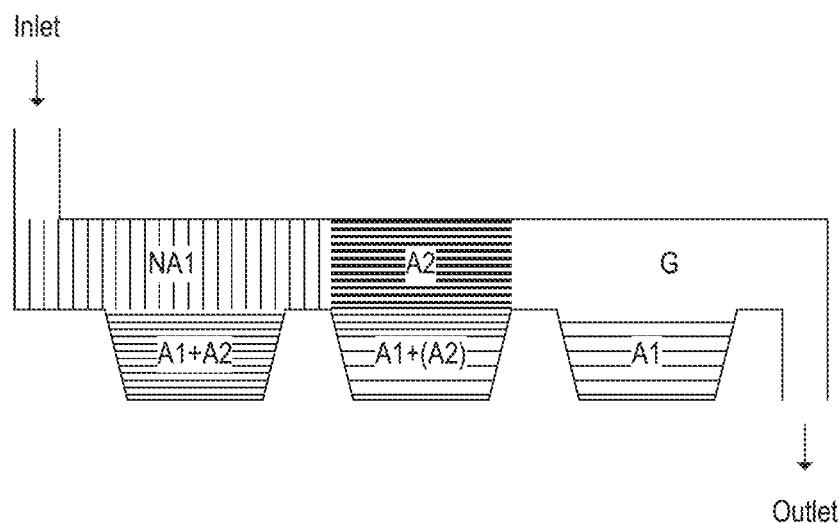
FIG. 5B provides a schematic illustration of an exemplary flowcell undergoing a co-injection of a first fluid and a second fluid according some embodiments of the methods provided herein.

FIG. 5A shows an exemplary dispensing pipette comprising an aqueous liquid ("A2") and a non-aqueous liquid ("NA") positioned at the pipette tip interface of the inlet port of an exemplary cartridge prior to co-injection. FIG. 5B provides a schematic illustration of an exemplary flowcell undergoing a co-injection of a first fluid and a second fluid according some embodiments of the methods provided herein. FIGS. 5A and 5B show that two buffers are aspirated sequentially, buffer 1 ("A2") then buffer 2 ("NA1"). The two buffers do not mix (e.g. an aqueous and non-aqueous buffer) and buffer1 can be less dense than buffer2. The two buffers (or liquids more general) are then dispensed together. Since the flow rate and the volume of buffer 2 are precisely controlled, and the flowcell dimensions is known, the duration for buffer 2 to pass over each microwell in the microwell array can be controlled with high precision. In some embodiments, serial co-injection of an aqueous buffer followed a non-aqueous buffer to a flowcell containing a microwell array, where the microwells are pre-filled with an aqueous buffer, can enable the content of one aqueous buffer to enter the other buffer (e.g., from the aqueous buffer being co-injected into the aqueous buffer in the microwells). Precise control over duration in which aqueous buffer 2 interfaces to the microwell surface can be achieved by precise control over the volume of buffer 2 and flow rate of buffer 2 in some embodiments. In some embodiments, variation of the interface duration (through change in the volume of buffer 2 and/or flow rate) enables control over final admix ratio of [aqueous buffer 1]: [aqueous buffer 2]. The interface duration can be dynamically controlled using the systems and apparatuses disclosed herein, to enable controlled admix ratios at different points along the flow channel. The co-injection of non-aqueous liquid (or gas) can physically seal the microwells and contain the contents.

Referring to FIGS. 5A and 5B, the flowcell depicted comprises a fluidic channel, an inlet, and outlet. The bottom of the fluidic channel is shown as comprising a substrate which comprises a plurality of microwells. Prior to the co-injection, the microwells comprise a first aqueous liquid ("A1") and the volume or space of the fluidic channel excluding the volumes and spaces of the microwells comprises a gas ("G"). The fluid of the fluidic channel (excluding the microwells) is displaced by a first fluid of the co-injection comprising a second aqueous liquid ("A2"). The microwell immediately adjacent to the inlet has been passed by the first fluid of the co-injection and now contains an admixture of the first aqueous liquid and the second aqueous liquid ("A1+A2"). The first fluid of the co-injection is immediately followed by a second fluid of the co-injection comprising a first non-aqueous liquid ("NA1"). The second fluid of the co-injection is depicted sealing the content the microwell immediately adjacent to the inlet. The first fluid of the co-injection is shown interfacing with a surface of the content of the microwell located in the middle of the fluidic channel, where one or more components of the first fluid of the co-injection are in the process of entering (e.g., by diffusion) the content of the microwell ("A1+(A2)"). The microwell adjacent to the outlet has not yet been reached by the first fluid of the co-injection.

Figure 6A:
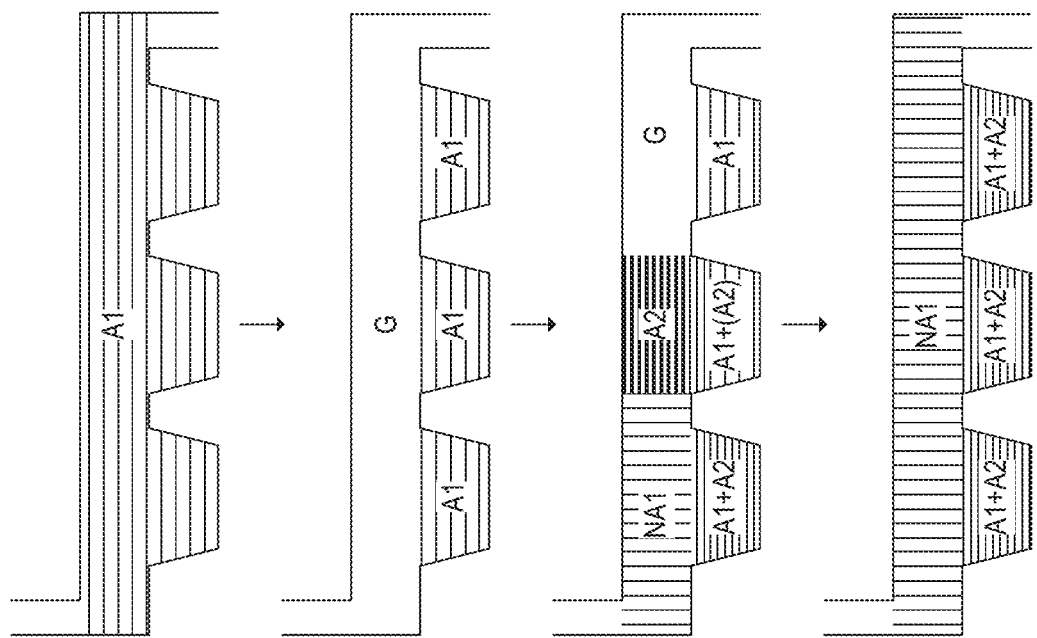

FIGS. 6A-6D depict non-limiting exemplary workflows for co-injection of two fluids (e.g., a first fluid and a second fluid) into a flowcell. The first fluid and the second fluid can be a buffer or a gas, for example. FIG. 6A depicts the priming of a flowcell by injection of a priming fluid comprising a first aqueous liquid ("A1") into the fluidic channel. A displacing fluid comprising a gas ("G") is injected into the fluidic channel and displaces the priming fluid from the fluidic channel (excluding the microwells). Prior to the co-injection, the microwells comprise a first aqueous liquid ("A1") and the fluidic channel (excluding the microwells) comprises a gas ("G"). Next, a first fluid comprising a second aqueous liquid ("A2") and second fluid comprising a first non-aqueous liquid ("NA1") are co-injected into the fluidic channel, with the first fluid of the co-injection introduced into the fluidic channel immediately before the second fluid of the co-injection. The fluid in the fluidic channel (excluding the microwells), if any, is displaced by the first fluid of the co-injection. The microwell immediately adjacent to the inlet has been passed by the first fluid of the co-injection and now contains an admixture of the first aqueous liquid and the second aqueous liquid ("A1+A2"). The second fluid of the co-injection is depicted sealing the content the microwell immediately adjacent to the inlet. The first fluid of the co-injection is shown interfacing with a surface of the content of the microwell located in the middle of the fluidic channel, where one or more components of the first fluid of the co-injection are in the process of entering (e.g., by diffusion) the content of the microwell ("A1+(A2)"). The microwell adjacent to the outlet has not yet been reached by the first fluid of the co-injection. The second fluid of the co-injection is depicted sealing the contents the plurality of microwells following the co-injection.

FIG. 6B depicts the priming of a flowcell by injection of a priming fluid comprising a first aqueous liquid ("A1") into the fluidic channel. A displacing fluid comprising a gas ("G") is injected into the fluidic channel and displaces the priming fluid from the fluidic channel (excluding the microwells). Prior to the co-injection, the microwells comprise a first aqueous liquid ("A1") and the fluidic channel (excluding the microwells) comprises a gas ("G"). Next, a first fluid comprising a second aqueous liquid ("A2") and second fluid comprising a gas ("G") are co-injected into the fluidic channel, with the first fluid of the co-injection introduced into the fluidic channel immediately before the second fluid of the co-injection. The fluid in the fluidic channel (excluding the microwells) is displaced by the first fluid of the co-injection. The microwell immediately adjacent to the inlet has been passed by the first fluid of the co-injection and now contains an admixture of the first aqueous liquid and the second aqueous liquid ("A1+A2"). The second fluid of the co-injection is depicted sealing the content the microwell immediately adjacent to the inlet. The first fluid of the co-injection is shown interfacing with a surface of the content of the microwell located in the middle of the fluidic channel, where one or more components of the first fluid of the co-injection are in the process of entering (e.g., by diffusion) the content of the microwell ("A1+(A2)"). The microwell adjacent to the outlet has not yet been reached by the first fluid of the co-injection. The second fluid of the co-injection is depicted sealing the contents the plurality of microwells following the co-injection.

Figure 6D:
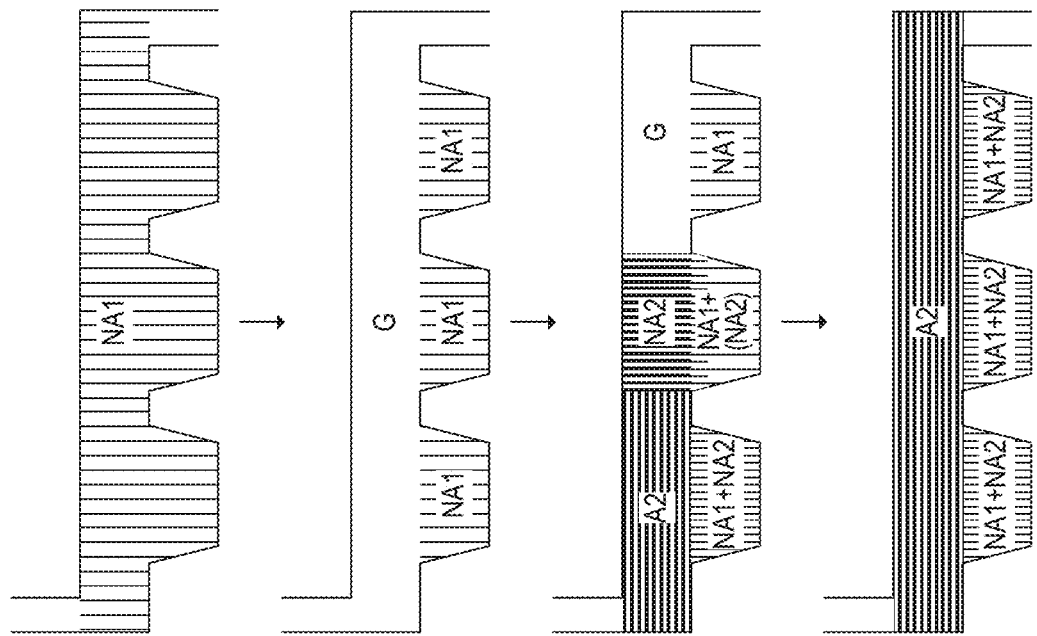
Figure 6C:
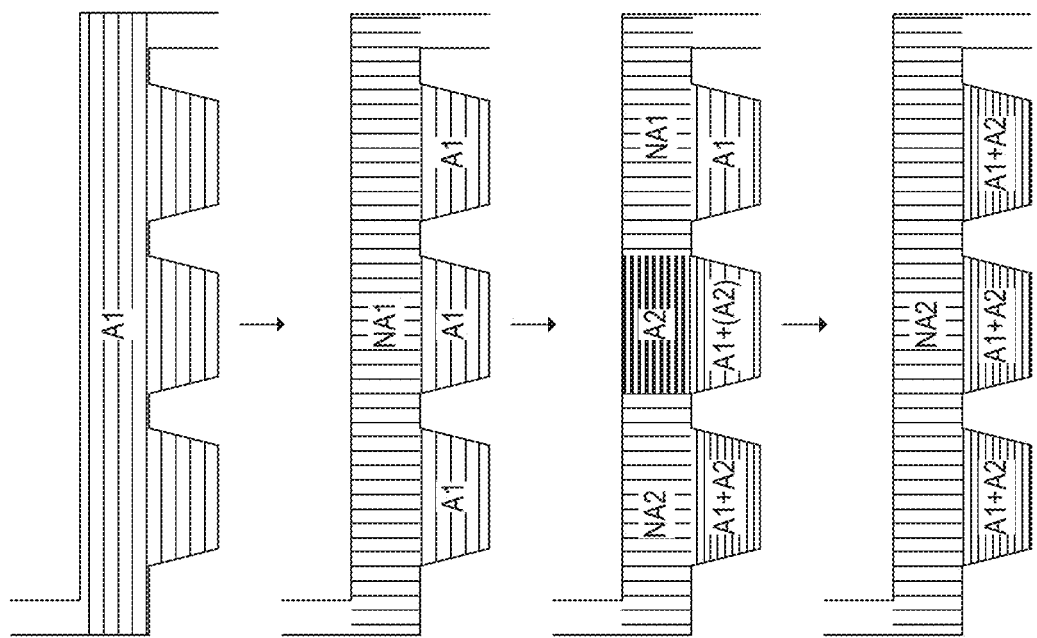

FIG. 6C depicts the priming of a flowcell by injection of a priming fluid comprising a first aqueous liquid ("A1") into the fluidic channel. A displacing fluid comprising a first non-aqueous liquid ("NA1") is injected into the fluidic channel and displaces the priming fluid from the fluidic channel (excluding the microwells). Prior to the co-injection, the microwells comprise a first aqueous liquid ("A1") and the volume or space of the fluidic channel (above and excludes the microwells) comprises a first non-aqueous liquid ("NA1"). Next, a first fluid comprising a second aqueous liquid ("A2") and second fluid comprising a second non-aqueous liquid ("NA2"), which can be the same non-aqueous liquid as the first non-aqueous liquid, are co-injected into the fluidic channel, with the first fluid of the co-injection introduced into the fluidic channel immediately before the second fluid of the co-injection. The fluid in the fluidic channel (excluding the microwells) is displaced by the first fluid of the co-injection. The microwell immediately adjacent to the inlet has been passed by the first fluid of the co-injection and now contains an admixture of the first aqueous liquid and the second aqueous liquid ("A1+A2"). The second fluid of the co-injection is depicted sealing the content the microwell immediately adjacent to the inlet. The first fluid of the co-injection is shown interfacing with a surface of the content of the microwell located in the middle of the fluidic channel, where one or more components of the first fluid of the co-injection are in the process of entering (e.g., by diffusion) the content of the microwell ("A1+(A2)"). The microwell adjacent to the outlet has not yet been reached by the first fluid of the co-injection. The second fluid of the co-injection is depicted sealing the contents the plurality of microwells following the co-injection.

FIG. 6D depicts the priming of a flowcell by injection of a priming fluid comprising a first non-aqueous liquid ("NA1") into the fluidic channel. A displacing fluid comprising a gas ("G") is injected into the fluidic channel and displaces the priming fluid from the fluidic channel (excluding the microwells). Prior to the co-injection, the microwells comprise a first non-aqueous liquid ("NA1") and the fluidic channel (excluding the microwells) comprises a gas ("G"). Next, a first fluid comprising a second non-aqueous liquid ("NA2") and second fluid comprising a first aqueous liquid ("A1") are co-injected into the fluidic channel, with the first fluid of the co-injection introduced into the fluidic channel immediately before the second fluid of the co-injection. The fluid in the fluidic channel (excluding the microwells) is displaced by the first fluid of the co-injection. The microwell immediately adjacent to the inlet has been passed by the first fluid of the co-injection and now contains an admixture of the first non-aqueous liquid and the second non-aqueous liquid ("NA1+NA2"). The second fluid of the co-injection is depicted sealing the content the microwell immediately adjacent to the inlet. The first fluid of the co-injection is shown interfacing with a surface of the content of the microwell located in the middle of the fluidic channel, where one or more components of the first fluid of the co-injection are in the process of entering (e.g., by diffusion) the content of the microwell ("NA1+(NA2)"). The microwell adjacent to the outlet has not yet been reached by the first fluid of the co-injection. The second fluid of the co-injection is depicted sealing the contents the plurality of microwells following the co-injection.

In some embodiments, the flow rate of the first fluid is equal to the flow rate of the second fluid. In some embodiments, the first fluid and the second fluid are immiscible. In some embodiments, the density of the first fluid is greater than the density of the second fluid. In some embodiments, the density of the first fluid is greater than the density of the second fluid, and wherein the first fluid and the second fluid are immiscible. The first fluid can comprise a second aqueous liquid and the second fluid can comprise a first non-aqueous fluid. The first fluid can comprise a second aqueous liquid and the second fluid can comprise a gas. The first fluid can comprise a second non-aqueous liquid and the second fluid can comprise a second aqueous liquid. The second fluid can have the same composition as the displacing fluid or a different composition than the displacing fluid. The first fluid can have a different composition than the displacing fluid. As used herein, the term "immiscible" shall be given its ordinary meaning and shall also refer to the resistance to mixing of at least two phases or fluids under a given condition or set of conditions (e.g., temperature and/or pressure) such that the at least two phases or fluids persist or remain at least partially separated even after the phases have undergone some type of mechanical or physical agitation (e.g., a gas in contact with a liquid, a non-aqueous liquid in contact with an aqueous liquid). In some embodiments, the at least two phases or fluids persist or remain fully separated even after the phases have undergone some type of mechanical or physical agitation. The gas can be any gas, such as for example, air, nitrogen, or argon. In some embodiments, the non-aqueous liquid is an oil (e.g., decane, tetradecane, or hexadecane, silicone oil, mineral oil), a hydrocarbon, a fluorocarbon, or any combination thereof.

The diffusion of one or more components of the first fluid into the microwell can produce a first admixture of the first fluid and the initial microwell liquid. In some embodiments, one or more components of the first fluid are present at a lower concentration in the initial microwell liquid or are absent in the initial microwell liquid. The concentration of the one or more components of the first fluid within the first admixture can comprise is, is about, is at most, or is at least 2-fold higher (e.g., 2.0, 2.1, 2.2, 2.3, 2.4, 2.5, 2.6, 2.7, 2.8, 2.9, 3, 4, 5, 6, 7, 8, 9, 10, 20, 30, 40, 50, 60, 70, 80, 90, 100-fold or higher and overlapping ranges therein) than the concentration of the one or more components of the first fluid in the initial microwell liquid.

In some embodiments, the duration is less than the reaction duration. In some embodiments, the reaction initiates after the duration has occurred. In some embodiments, the reaction initiates after the second fluid seals the content of the microwell. In some embodiments, the duration is short enough that one or more components of the microwell do not diffuse out of the microwell. The one or more components of the microwell can comprise a cell, a bead, a biomolecule, a buffer component, a small molecule, a biomolecule, a reagent, an agent, or any combination thereof. The reaction duration can be between about 1 second and about 6 hours (e.g., 1 s, 30 s, 1 min, 5 min, 30 min, 45 min, 1 hour, 2 hours, 4 hours, 6 hours, and overlapping ranges therein). The duration can be dynamically controlled. In some embodiments, the duration is a function of the volume of the first fluid, the flow rate of the first fluid, the flowcell dimensions, or any combination thereof. The duration can be dynamically controlled by adjusting the volume of the first fluid, the flow rate of the first fluid, or any combination thereof. In some embodiments, the final concentration of the one or more components of the first fluid in the microwell following the duration is a function of the duration and/or flowcell dimensions. In some embodiments, the flow rate of the first fluid is gradually decreased as it traverses the fluidic channel, wherein the final concentration of the one or more components of the first fluid in each microwell is uniform across the plurality of microwells. In some embodiments, one or more components of the first fluid entering the content of the microwell terminates a reaction.

The speed of the flow at a boundary between the flow and the bottom can be non-zero. The relative flow velocity of a flow across a cross-section of the fluidic channel can be approximately constant. In some embodiments, the flow is plug flow. In some embodiments, the ceiling comprises a hydrophilic coating (e.g., polyethylene glycol (PEG), polyHema, pluronic acid F68, pluronic acid F108, pluronic acid F127, polysorbate 20, silicon dioxide ($SiO_2$), and/or silicon nitride). In some embodiments, the angle of the ceiling is sufficiently smaller than the contact angle of the first sidewall. In some embodiments, the first fluid is a first plug and the second fluid is a second plug. In some embodiments, a priming fluid, a displacement fluid, a first fluid of a first co-injection, a second fluid of a first co-injection, a first fluid of a second co-injection, a second fluid of a second co-injection, a first fluid of a third co-injection, a second fluid of a third co-injection, a first fluid of a fourth co-injection, a second fluid of a fourth co-injection, a first fluid of a fifth co-injection, and/or a second fluid of a fifth co-injection are plugs.

In some embodiments, the second fluid sealing the content of the microwell reduces cross-talk. In some embodiments, the second fluid sealing the content of the microwell reduces cross-talk by, by about, by at most about, or by at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to as compared to comparable flowcell methods performed using a single fluid injection. Cross-talk can comprise the diffusion of nucleic acids, proteins, antibodies, biomolecules, or any combination thereof, from one microwell to another microwell. Cross-talk can comprise the diffusion of nucleic acids, proteins, antibodies, biomolecules, or any combination thereof, from a microwell to the volume or space of the fluidic channel (above the microwells). In some embodiments, the substrate can comprise a microwell array, wherein the microwell array comprises at least 100 microwells, wherein each microwell has a volume ranging from about 1,000 $\mu m^3$ to about 786,000 $\mu m^3$. In some embodiments, the reduced cross-talk enables use of a higher density microwell array without a concomitant increase in cross-talk. The higher density microwell array can comprise at least 100 more microwells per inch as compared to a standard microwell array. In some embodiments, the use of the higher density microwell array increases cell loading efficiency and/or bead loading efficiency as compared to a standard microwell array. The use of the higher density microwell array can decrease the number doublet events as compared to a standard microwell array.

The method can comprise, prior to the co-injecting, capturing single cells in the plurality of microwells. The method can comprise, prior to the co-injecting, capturing single cells and single beads in the plurality of microwells, wherein a single bead comprises a plurality of tethered barcodes, and wherein the plurality of tethered barcode further comprises: i) a bead-specific cellular label; ii) a diverse set of molecular labels; and/or iii) a plurality of target binding regions capable of hybridizing with nucleic acid molecules. The reaction can comprise cell lysis. The first fluid can comprise a lysis buffer. In some embodiments, the duration is a length of time sufficient to deliver an amount of lysis buffer to the microwell sufficient to lyse the cell. In some embodiments, the second fluid sealing the content of the microwell yields an increase in the number of mRNAs and/or cellular component-binding reagent oligonucleotides captured by barcodes as compared to comparable flowcell methods performed using a single fluid injection. The second fluid sealing the content of the microwell can increase in the number of mRNAs and/or cellular component-binding reagent oligonucleotides captured by the barcodes by, by about, by at most about, or at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to comparable flowcell methods performed using a single fluid injection.

In some embodiments, the second fluid sealing the content of the microwell yields an increase in the number of occurrences of unique molecular labels associated with each of the mRNAs and/or cellular component-binding reagent oligonucleotides determined as compared to comparable flowcell methods performed using a single fluid injection. The second fluid sealing the content of the microwell can increase the number of occurrences of unique molecular labels associated with each of the mRNAs and/or cellular component-binding reagent oligonucleotides determined by, by about, by at most about, or at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to comparable flowcell methods performed using a single fluid injection.

In some embodiments, the second fluid sealing the content of the microwell yields an increase in the signal-to-noise ratio as compared to comparable flowcell methods performed using a single fluid injection. The second fluid sealing the content of the microwell can increase in the signal-to-noise ratio by, by about, by at most about, or at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 2×, 3×, 4×, 5×, 6×, 7×, 8×, 9×, 10×, 20×, 30×, 40×, 50×, 60×, 70×, 80×, 90×, 100×, or higher and overlapping ranges therein) as compared to comparable flowcell methods performed using a single fluid injection.

In some embodiments, the method does not comprise the use of buffer additives to reduce cross-talk, such as for example, buffer additives adjusting the viscosity of fluids and/or reagents. Buffer additives can comprise sucrose, polyethylene glycol (PEG), Ficoll, glycerin, glycerol, dextran sulfate, histopaque, bovine serum albumin, or any combination thereof.

In some embodiments, a device is provided comprising the flowcell comprises at least one inlet port and at least one outlet port, wherein the at least one inlet port and at least one outlet port are capable of directing a flow of a fluid through the flow cell, thereby contacting the microwells with the fluid. In some embodiments, the device comprising the flowcell is a removable, consumable component of an instrument system configured to perform automated, barcoding assays on a plurality of single cells.

Non-Uniform Flow Rates

The flow rate of the first fluid can be uniform or not uniform along the longitudinal path of the fluidic channel. In some embodiments, the flow rate of the first fluid changes (e.g., increases and/or decreases) along the longitudinal path of the fluidic channel. In some embodiments, the change in the flow rate of the first fluid can be linear, non-linear, exponential, logarithmic, or any combination thereof. In some embodiments, the flow rate of the first fluid is higher at an anterior position along the longitudinal path of the fluidic channel relative a posterior position along the longitudinal path of the fluidic channel while in other embodiments the flow rate of the first fluid is lower at an anterior position along the longitudinal path of the fluidic channel relative a posterior position along the longitudinal path of the fluidic channel. In some embodiments, the difference between the flow rate of the first fluid at the anterior position relative the posterior position is, is about, is at most about, or is at least about 1.1-fold. In some embodiments, the ratio of the flow rate of the first fluid at the anterior position relative the posterior position ranges from 1:100 to 100:1. In some embodiments, the ratio of the flow rate of the first fluid at the anterior position relative the posterior position is at most 10:1. In some embodiments, the ratio of the flow rate of the first fluid at the anterior position relative the posterior position is at most 100:1. In some embodiments, the ratio of the flow rate of the first fluid at the anterior position relative the posterior position is at most 1:1000. In some embodiments, the ratio of the flow rate of the first fluid at the anterior position relative the posterior position is at least 1:10. In some embodiments, the ratio of the flow rate of the first fluid at the anterior position relative the posterior position is at least 1:100. In some embodiments, the ratio of the flow rate of the first fluid at the anterior position relative the posterior position is at least 1:1000.

In some embodiments, the ratio of the flow rate of the first fluid at the anterior position relative the posterior position can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

In some embodiments, the ratio can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

Figure 10A:
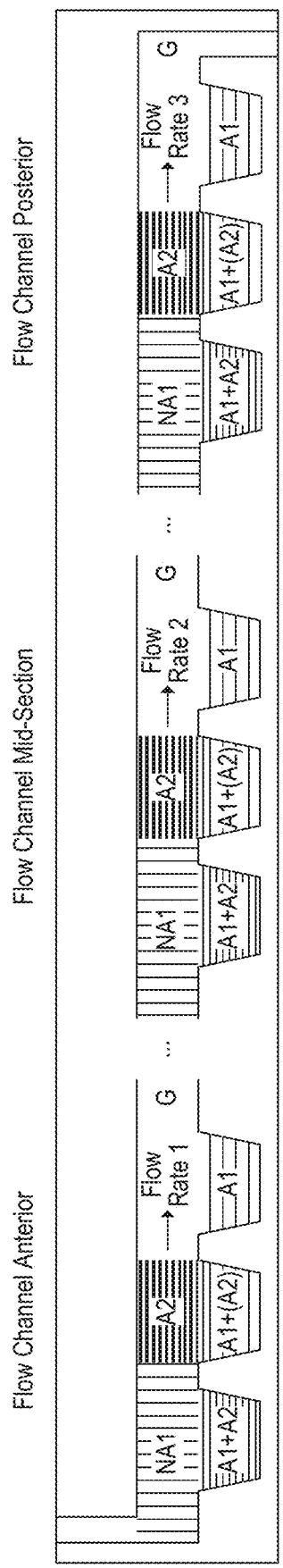
FIG. 10A provides a schematic illustrations of an exemplary flowcell undergoing a co-injection of a first fluid and a second fluid wherein the flow rate of the first fluid is non-uniform along the longitudinal path of the flow cell.

FIG. 10A provides a schematic illustrations of an exemplary flowcell undergoing a co-injection of a first fluid and a second fluid wherein the flow rate of the first fluid is non-uniform along the longitudinal path of the flow cell. Prior to the first co-injection, the microwells comprise a first aqueous liquid ("A1") and the fluidic channel (excluding the microwells) comprises a gas ("G"). Next, a first fluid comprising a second aqueous liquid ("A2") and second fluid comprising a first non-aqueous liquid ("NA1") are co-injected into the fluidic channel, with the first fluid of the co-injection introduced into the fluidic channel immediately before the second fluid of the co-injection. The fluid in the fluidic channel (excluding the microwells) is displaced by the first fluid of the co-injection. The flow rate of the first fluid is non-uniform along the longitudinal path of the flow cell, such that the flow rate of the first fluid at the flow channel anterior ("Flow Rate 1"), flow channel mid-section ("Flow Rate 2"), and flow channel posterior ("Flow Rate 3") are not equal.

Figure 10B:
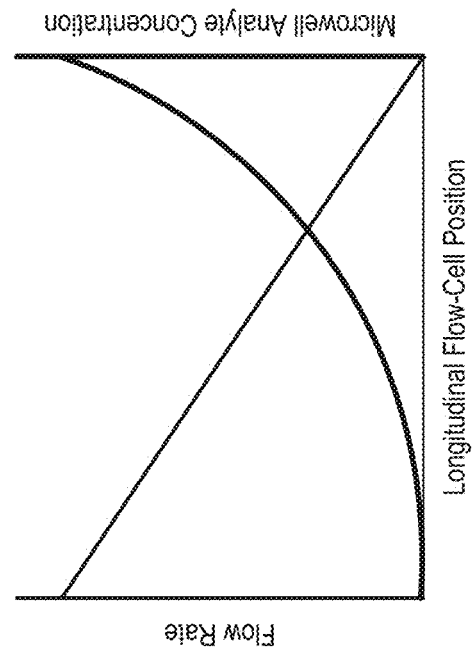
FIG. 10B provides a non-limiting exemplary chart showing the non-uniform flow rate of a first fluid of a co-injection comprising an analyte along the longitudinal path of a flow cell (thin line) and the non-uniform concentration of the analyte within the contents of microwells along the longitudinal path of the flow cell.

FIG. 10B provides a non-limiting exemplary chart showing the non-uniform flow rate of a first fluid of a co-injection comprising an analyte along the longitudinal path of a flow cell (thin line) and the non-uniform concentration of the analyte within the contents of microwells along the longitudinal path of the flow cell.

FIGS. 10A and 10B show that the flow rate of the second aqueous fluid (e.g. an aqueous buffer) can be increased as the second aqueous fluid passes through the flow-cell. The first flow rate can be smaller than the second flow rate, which in turn can be smaller than the third flow rate. The duration of diffusion of the second aqueous fluid from the bulk fluid to the microwells, is reduced for increased flow rates, resulting in a lower concentration of the components of the second aqueous fluid for microwells located at this cross-section of the flow or fluidic channel corresponding to this flow rate. By dynamically varying the rate of the second aqueous fluid with a high precision, the resulting concentration profile of the second aqueous fluid, or components or contents thereof, can be precisely controlled along a microwell array. For example, if a buffer (e.g., with a plug flow) containing a given analyte is passed through a flowcell at a continuously increasing flow rate, the resulting analyte concentration in the microwells can continuously decrease along the path length of the flow channel. When the dispense flow rate is varied at various portions of the flow channel, the method can be utilized to control the concentration of one or multiple analytes in the micro-wells along the longitudinal path of the flow channel.

In some embodiments, the final concentration of the one or more components of the first fluid in the contents of the plurality of microwells following the co-injecting is uniform. In some embodiments, the coefficient of variation for the final concentration of the one or more components of the first fluid in the contents of the plurality of microwells following the co-injecting is less than 5% (e.g., 5%, 4%, 3%, 2%, 1%, 0.5%, 0.1%, 0.01%, and overlapping rangers therein). In some embodiments, the final concentration of the one or more components of the first fluid in the contents of the plurality of microwells following the serial the co-injecting is non-uniform. The final concentration of the one or more components of the first fluid in the content of each microwell can change along the longitudinal path of the fluidic channel. The change in the final concentration of the one or more components of the first fluid in the content of each microwell can be linear, non-linear, exponential, and/or logarithmic. In some embodiments, the difference between the final concentration of the one or more components of the first fluid in the content of a microwell at an anterior position along the longitudinal path of the fluidic channel relative a posterior position along the longitudinal path of the fluidic channel is, is about, is at most about, or is at least about 1.1-fold. In some embodiments, the ratio of the final concentration of the one or more components of the first fluid in the content of a microwell at an anterior position along the longitudinal path of the fluidic channel relative a posterior position along the longitudinal path of the fluidic channel ranges from 1:100 to 100:1. In some embodiments, the ratio of the final concentration of the one or more components of the first fluid in the content of a microwell at an anterior position along the longitudinal path of the fluidic channel relative a posterior position along the longitudinal path of the fluidic channel is at most 10:1. In some embodiments, the ratio of the final concentration of the one or more components of the first fluid in the content of a microwell at an anterior position along the longitudinal path of the fluidic channel relative a posterior position along the longitudinal path of the fluidic channel is at most 100:1. In some embodiments, the ratio of the final concentration of the one or more components of the first fluid in the content of a microwell at an anterior position along the longitudinal path of the fluidic channel relative a posterior position along the longitudinal path of the fluidic channel is at most 1:1000. In some embodiments, the ratio of the final concentration of the one or more components of the first fluid in the content of a microwell at an anterior position along the longitudinal path of the fluidic channel relative a posterior position along the longitudinal path of the fluidic channel is at least 1:10. In some embodiments, the ratio of the final concentration of the one or more components of the first fluid in the content of a microwell at an anterior position along the longitudinal path of the fluidic channel relative a posterior position along the longitudinal path of the fluidic channel is at least 1:100. In some embodiments, the ratio of the final concentration of the one or more components of the first fluid in the content of a microwell at an anterior position along the longitudinal path of the fluidic channel relative a posterior position along the longitudinal path of the fluidic channel is at least 1:1000.

In some embodiments, the ratio of the final concentration of the one or more components of the first fluid in the content of a microwell at an anterior position along the longitudinal path of the fluidic channel relative a posterior position along the longitudinal path of the fluidic channel can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio of the final concentration of the one or more components of the first fluid in the content of a microwell at an anterior position along the longitudinal path of the fluidic channel relative a posterior position along the longitudinal path of the fluidic channel can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

In some embodiments, the ratio can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1. In some embodiments, the final concentration of the one or more components of the first fluid in the content of each microwell increases along the longitudinal path of the fluidic channel. In some embodiments, final concentration of the one or more components of the first fluid in the content of each microwell decreases along the longitudinal path of the fluidic channel.

Figure 11:
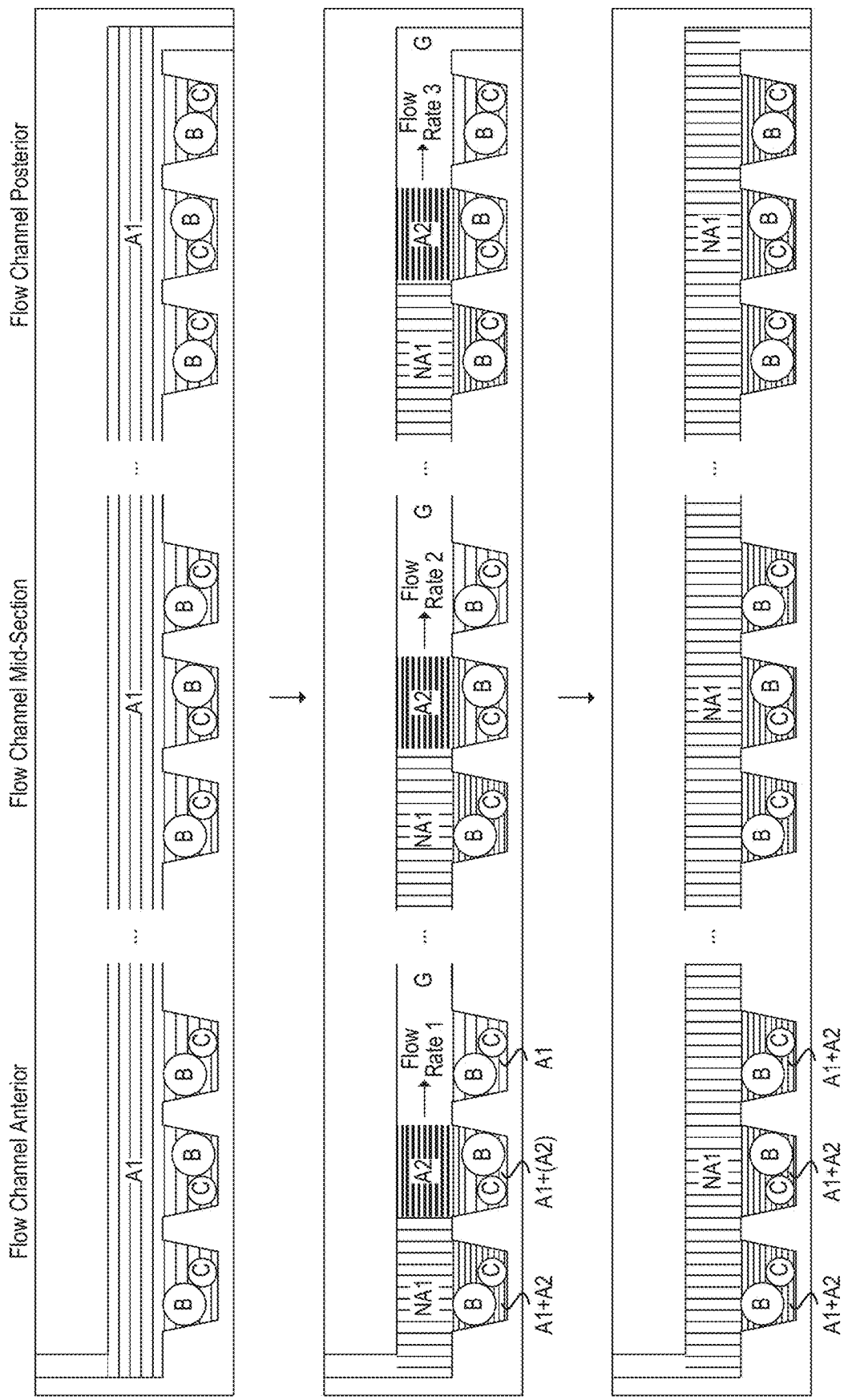
FIG. 11 provides exemplary schematic illustrations of the anterior, mid-section, and posterior of a flowcell undergoing a co-injection of a first fluid and a second fluid wherein the flow rate of the first fluid is non-uniform along the longitudinal path of the flow cell.

FIG. 11 provides exemplary schematic illustrations of the anterior, mid-section, and posterior of a flowcell undergoing a co-injection of a first fluid and a second fluid wherein the flow rate of the first fluid is non-uniform along the longitudinal path of the flow cell.

As illustrated, cells and beads can be loaded into partitions, such as microwells (top row in the figure). Next, a desired analyte concentration profile along the longitudinal flow cell path length can be created (middle row of the figure). Multiple analytes with multiple different concentration profiles can be created. Microwells can be sealed with oil contain and incubate cells, beads, and analytes in physically separate micro-reaction chambers (bottom row of the figure). Subsequently, an analysis assay can be performed. For example, Rhapsody™ RNA expression analysis or Rhapsody™ protein expression analysis on the cells can be used determine the effect of analyte concentrations at a single cell level.

Prior to the co-injection, the fluidic channel comprises air and the microwells comprise a single bead ("B"), a single cell ("C"), and a first aqueous liquid. Next, a first fluid comprising a second aqueous liquid ("A2") and second fluid comprising a first non-aqueous liquid ("NA1") are co-injected into the fluidic channel, with the first fluid of the first co-injection introduced into the fluidic channel immediately before the second fluid of the first co-injection. The second aqueous liquid ("A2") comprises an analyte. The fluid in the fluidic channel (excluding the microwells) is displaced by the first fluid of the first co-injection. The flow rate of the first fluid is non-uniform along the longitudinal path of the flow cell, such that the flow rate of the first fluid at the flow channel anterior ("Flow Rate 1"), flow channel mid-section ("Flow Rate 2"), and flow channel posterior ("Flow Rate 3") are not equal. The microwells that have been passed by the first fluid of the co-injection now contain an admixture of the first aqueous liquid and the analyte of the second aqueous liquid ("A1+A2"). For microwells where the first fluid is shown interfacing with a surface of the content of the microwell, the analyte of the first fluid is in the process of entering the content of the microwell ("A1+(A2)"). The second fluid of the co-injection is depicted sealing the contents the plurality of microwells following the co-injection. Due to the non-uniform flow rate of the first fluid along the longitudinal path of the flow cell, the duration during which the first fluid interfaces with the surface of the content of the microwells is variable, and consequently the final concentration of the analyte within the contents of the microwells is not uniform along the longitudinal path of the flow cell.

The flowcell dimensions (e.g., volume of the microwell and/or the surface area of the microwell interfacing the fluidic channel (excluding the microwells)) can be uniform or not uniform across the plurality of microwells. In some embodiments, the difference between the volume of a microwell at an anterior position along the longitudinal path of the fluidic channel relative a posterior position along the longitudinal path of the fluidic channel is, is about, is at most about, or is at least about 1.1-fold (e.g., 1.1, 1.3, 1.5, 1.7, 1.9, 2.0, 2.5, 3, 5, 10, 20, 30, 40, 50, 60, 70, 80, 90, 100-fold or higher and overlapping ranges therein). In some embodiments, the difference between the surface area of a microwell interfacing the fluidic channel (excluding the microwells) at an anterior position along the longitudinal path of the fluidic channel relative a posterior position along the longitudinal path of the fluidic channel is, is about, is at most about, or is at least about 1.1-fold (e.g., 1.1, 1.3, 1.5, 1.7, 1.9, 2.0, 2.5, 3, 5, 10, 20, 30, 40, 50, 60, 70, 80, 90, 100-fold or higher and overlapping ranges therein).

Co-Injections of Fluids

In some embodiments, the method can comprise a second co-injecting of fluids into the fluidic channel. In some embodiments, the second co-injecting of fluids comprises co-injecting a first fluid of a second co-injection and a second fluid of a second co-injection into the fluidic channel, wherein the first fluid of the second co-injection is introduced into the fluidic channel immediately before the second fluid of a second co-injection, and wherein the second fluid of the second co-injection seals the content of the microwell. In some embodiments, the first fluid of the second co-injection and the second fluid of the second co-injection are immiscible. In some embodiments, the density of the first fluid of the second co-injection is greater than the density of the second fluid of the second co-injection. In some embodiments, the density of the first fluid of the second co-injection is greater than the density of the second fluid of the second co-injection, and wherein the first fluid of the second co-injection and the second fluid of the second co-injection are immiscible. In some embodiments, the density of the first fluid of the a co-injection is greater than the density of the second fluid of the a co-injection, and wherein the first fluid of the a co-injection and the second fluid of the a co-injection are immiscible.

The second co-injecting can be performed in the reverse direction relative to the first co-injecting. The first fluid of the second co-injection can comprise an aqueous liquid and the second fluid of the second co-injection can comprise a non-aqueous liquid. The first fluid of the second co-injection can comprise an aqueous liquid and the second fluid of the second co-injection can comprise a gas.

The first fluid of the second co-injection can comprise a non-aqueous liquid and the second fluid of the second co-injection can comprise an aqueous liquid. In some embodiments, the first fluid of the first co-injection and the first fluid of the second co-injection can be the same or different. In some embodiments, the second fluid of the first co-injection and the second fluid of the second co-injection can be the same or different.

Two Co-Injections of Fluids

Figure 7:
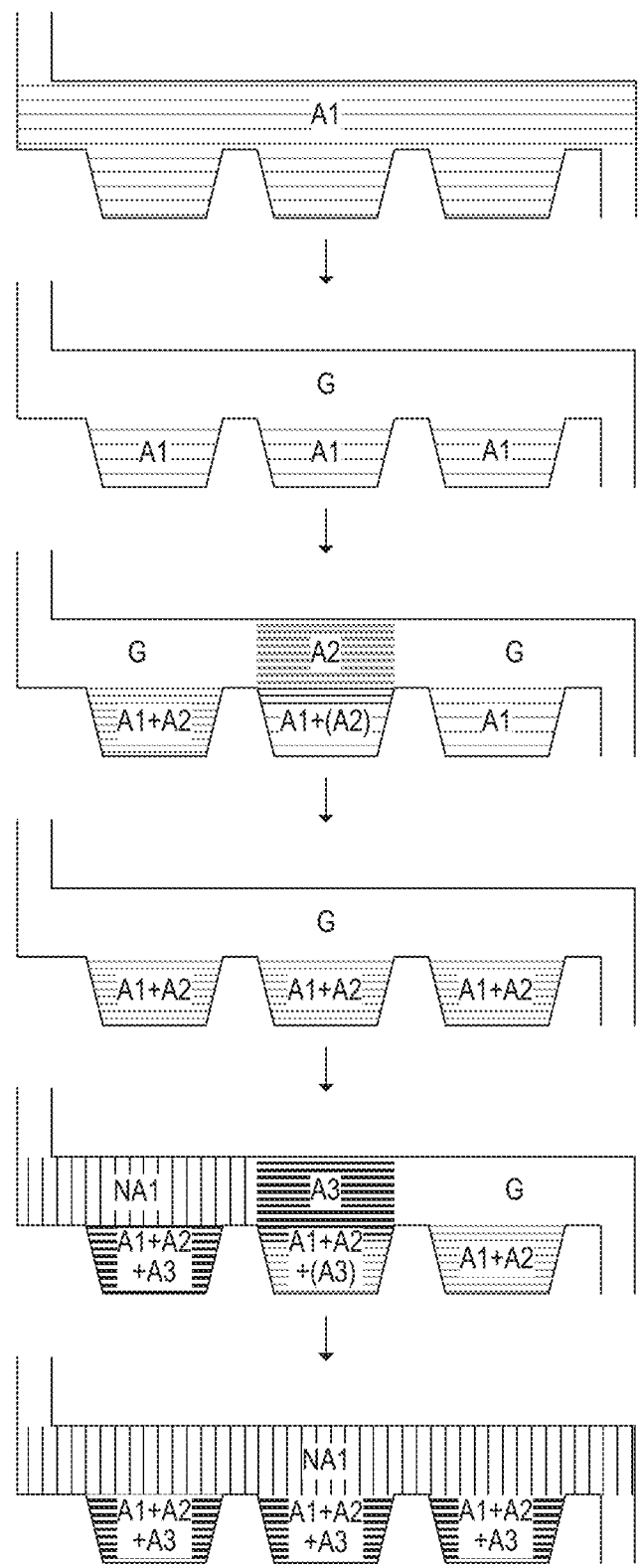
FIG. 7 depicts a non-limiting exemplary workflows for a first co-injection of a first fluid and a second fluid into a flowcell followed by a second co-injection of a first fluid and a second fluid into the flowcell.

FIG. 7 depicts a non-limiting exemplary workflows for a first co-injection of a first fluid and a second fluid into a flowcell followed by a second co-injection of a first fluid and a second fluid into the flowcell. FIG. 7 depicts the priming of a flowcell by injection of a priming fluid comprising a first aqueous liquid ("A1") into the fluidic channel. A displacing fluid comprising a gas ("G") is injected into the fluidic channel and displaces the priming fluid from the fluidic channel (excluding the microwells). Prior to the first co-injection, the microwells comprise a first aqueous liquid ("A1") and the fluidic channel (excluding the microwells) comprises a gas ("G"). Next, a first fluid comprising a second aqueous liquid ("A2") and second fluid comprising a gas ("G") are co-injected into the fluidic channel, with the first fluid of the first co-injection introduced into the fluidic channel immediately before the second fluid of the first co-injection. The fluid in the fluidic channel (excluding the microwells) is displaced by the first fluid of the first co-injection. The microwell immediately adjacent to the inlet has been passed by the first fluid of the first co-injection and now contains an admixture of the first aqueous liquid and the second aqueous liquid ("A1+A2"). The second fluid of the first co-injection is depicted sealing the content the microwell immediately adjacent to the inlet. The first fluid of the first co-injection is shown interfacing with a surface of the content of the microwell located in the middle of the fluidic channel, where one or more components of the first fluid of the first co-injection are in the process of entering the content of the microwell ("A1+(A2)"). The microwell adjacent to the outlet has not yet been reached by the first fluid of the first co-injection. The second fluid of the first co-injection is depicted sealing the contents the plurality of microwells following the first co-injection. Prior to the second co-injection, the microwells comprise an admixture of the first aqueous liquid and the second aqueous liquid ("A1+A2") and the volume or space of the fluidic channel (excluding the microwells) comprises a gas ("G"). Next, a first fluid comprising a third aqueous liquid ("A3") and second fluid comprising a first non-aqueous liquid ("NA1") are co-injected into the fluidic channel, with the first fluid of the second co-injection introduced into the fluidic channel immediately before the second fluid of the second co-injection. The fluid is displaced by the first fluid of the second co-injection. The microwell immediately adjacent to the inlet has been passed by the first fluid of the second co-injection and now contains an admixture of the first aqueous liquid, the second aqueous liquid, and the third aqueous liquid ("A1+A2+A3"). The second fluid of the second co-injection is depicted sealing the content the microwell immediately adjacent to the inlet. The first fluid of the second co-injection is shown interfacing with a surface of the content of the microwell located in the middle of the fluidic channel, where one or more components of the first fluid of the second co-injection are in the process of entering the content of the microwell ("A1+A2+(A3)"). The microwell adjacent to the outlet has not yet been reached by the first fluid of the second co-injection. The second fluid of the second co-injection is depicted sealing the contents the plurality of microwells following the second co-injection.

Multiple Co-Injections of Fluids

Disclosed herein include methods for introducing one or more components. In some embodiments, the method comprises: (a) introducing a first fluid into a fluidic channel comprising a ceiling, a first sidewall, and a bottom, wherein the bottom of the fluidic channel comprises a plurality of microwells, and wherein the ceiling, the first sidewall, and the bottom of the fluidic channel surround a fluidic channel volume of the fluidic channel excluding the volume of each of the plurality of microwells (e.g., above the microwells), whereby the fluidic channel volume and each microwell of the plurality of microwells comprise the first fluid; (b) introducing a first displacement fluid into the fluidic channel to displace the first fluid from the fluidic channel volume; (d) introducing a plurality of second fluids, each immediately followed by and/or simultaneously with a second displacement fluid, into the fluidic channel at a second flow rate, wherein one or more components of each of the plurality of second fluids enters the content in the microwell when the second fluid comes into contact with the content in the microwell for a first duration, and wherein the second displacement fluid displaces the second fluid from the fluidic channel volume and/or seals the content of the microwell.

Figure 8A:
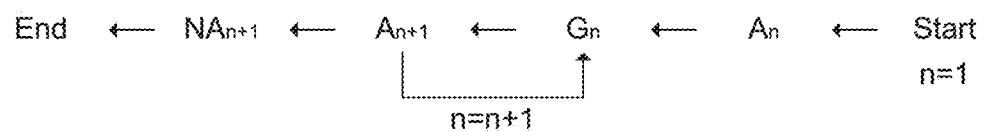
FIGS. 8A-8C depict non-limiting exemplary workflows for injections of fluids into a flowcell.
Figure 8B:
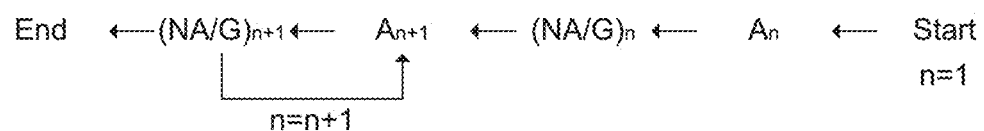
Figure 8C:
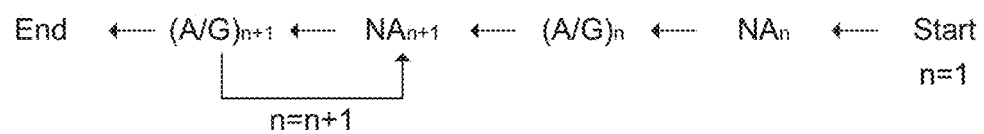

FIGS. 8A-8C depict non-limiting exemplary workflows for injections of fluids into a flowcell. The letter n indicates the number of times that each type of fluid (gas ("G"), aqueous liquids ("A"), and non-aqueous liquid ("NA") has been injected into the flowcell. A return arrow indicates a co-injection step of a first fluid and a second fluid, wherein the second fluid of the co-injection comprises a fluid that is (n+1). In some embodiments, either a non-aqueous liquid or a gas ("NA/G") are injected into the fluidic channel. In some embodiments, either an aqueous liquid or a gas ("A/G") are injected into the fluidic channel.

The workflow illustrated in FIG. 8A begins with an injection of an aqueous fluid (e.g., a priming fluid) into the fluidic channel (at n=1). A displacing gas is injected into the fluidic channel (at n=1) and displaces the aqueous fluid from the fluidic channel. Following one or more co-injections of a first fluid (e.g., an aqueous fluid $A_{n+1}$, where n=1) and a second fluid (e.g., a gas $G_n$, where n=2 after incrementing n by 1), the contents of the microwells are sealed (e.g., by $NA_{n+1}$, where n=2).

The workflow illustrated in FIG. 8C begins with an injection of an aqueous fluid (e.g., $A_n$, where n=1) into the fluidic channel. A displacing non-aqueous fluid or gas (e.g., NA or $G_n$, where n=1) is injected into the fluidic channel and displaces the aqueous fluid from the fluidic channel. These two fluids or gas may not be co-injected. Following a first co-injection of an aqueous fluid (e.g., $A_{n+1}$, where n=1) and a non-aqueous fluid or gas (e.g., NA or $G_{n+1}$, where n=1) and a second co-injection of an aqueous fluid (e.g., $A_{n+1}$, where n=2) and a non-aqueous fluid or gas (e.g., NA or $G_{n+1}$, where n=2) (or additional co-injections with n=3, 4, 5, 6, 7, 8, 9, 10, or more). The last non-aqueous fluid or gas can seal the contents of the microwells.

The workflow illustrated in FIG. 8C begins with an injection of a non-aqueous fluid (e.g., $NA_n$, where n=1) into the fluidic channel. A displacing aqueous fluid or gas (e.g., A or $G_n$, where n=1) is injected into the fluidic channel and displaces the non-aqueous fluid from the fluidic channel. These two fluids or gas my not be co-injected. Following a first co-injection of a non-aqueous fluid (e.g., $NA_{n+1}$, where n=1) and an aqueous fluid or gas (e.g., A or $G_{n+1}$, where n=1) and a second co-injection of a non-aqueous fluid (e.g., $A_{n+1}$, where n=2) and an aqueous fluid or gas (e.g., A or $G_{n+1}$, where n=2) (or additional co-injections with n=3, 4, 5, 6, 7, 8, 9, 10, or more). The last aqueous fluid or gas can seal the contents of the microwells.

In some embodiments, the methods can comprise 2, 3, 4, 5, 6, 7, 9, 9, or more co-injections of a first fluid and a second fluid. Tables 1-4 below compare non-limiting exemplary workflows for performing a single co-injection of a first fluid and a second fluid (Table 1), two co-injections of a first fluid and a second fluid (Table 2), three co-injections of a first fluid and a second fluid (Table 3), and four co-injections of a first fluid and a second fluid (Table 4).

TABLE 1

Fluids Employed in Exemplary Co-injection Workflows

| Priming fluid | Displacement Fluid | First Fluid of a Co-injection | Second Fluid of a Co-injection |
|---|---|---|---|
| AL | Gas | AL | Gas |
| AL | Gas | AL | NAL |
| AL | NAL | AL | Gas |
| AL | NAL | AL | NAL |
| NAL | Gas | NAL | Gas |
| NAL | Gas | NAL | AL |
| NAL | AL | NAL | Gas |
| NAL | AL | NAL | AL |

AL: Aqueous Liquid;
NAL: Non-aqueous Liquid

TABLE 2

Fluids Employed in Exemplary Co-injection Workflows

| Priming fluid | Displacement Fluid | First Fluid of a First Co-Injection | Second Fluid of a First Co-Injection | First Fluid of a Second Co-Injection | Second Fluid of a second Co-Injection |
|---|---|---|---|---|---|
| AL | Gas | AL | Gas | AL | Gas |
| AL | Gas | AL | Gas | AL | NAL |
| AL | Gas | AL | NAL | AL | Gas |
| AL | Gas | AL | NAL | AL | NAL |
| AL | NAL | AL | Gas | AL | Gas |
| AL | NAL | AL | Gas | AL | NAL |
| AL | NAL | AL | NAL | AL | Gas |
| AL | NAL | AL | NAL | AL | NAL |
| NAL | Gas | NAL | Gas | NAL | Gas |
| NAL | Gas | NAL | Gas | NAL | AL |
| NAL | Gas | NAL | AL | NAL | Gas |
| NAL | Gas | NAL | AL | NAL | AL |
| NAL | AL | NAL | Gas | NAL | Gas |
| NAL | AL | NAL | Gas | NAL | AL |
| NAL | AL | NAL | AL | NAL | Gas |
| NAL | AL | NAL | AL | NAL | AL |

AL: Aqueous Liquid;
NAL: Non-aqueous Liquid

TABLE 3

Fluids Employed in Exemplary Co-injection Workflows

| Priming fluid | Displacement Fluid | First Fluid of a First Co-Injection | Second Fluid of a First Co-Injection | First Fluid of a Second Co-Injection | Second Fluid of a Second Co-Injection | First Fluid of a Third Co-Injection | Second Fluid of a Third Co-Injection |
|---|---|---|---|---|---|---|---|
| AL | Gas | AL | Gas | AL | Gas | AL | Gas |
| AL | Gas | AL | Gas | AL | Gas | AL | NAL |
| AL | Gas | AL | Gas | AL | NAL | AL | Gas |
| AL | Gas | AL | Gas | AL | NAL | AL | NAL |
| AL | Gas | AL | NAL | AL | Gas | AL | Gas |
| AL | Gas | AL | NAL | AL | Gas | AL | NAL |
| AL | Gas | AL | NAL | AL | NAL | AL | Gas |
| AL | Gas | AL | NAL | AL | NAL | AL | NAL |
| AL | NAL | AL | Gas | AL | Gas | AL | Gas |
| AL | NAL | AL | Gas | AL | Gas | AL | NAL |
| AL | NAL | AL | Gas | AL | NAL | AL | Gas |
| AL | NAL | AL | Gas | AL | NAL | AL | NAL |
| AL | NAL | AL | NAL | AL | Gas | AL | Gas |
| AL | NAL | AL | NAL | AL | Gas | AL | NAL |
| AL | NAL | AL | NAL | AL | NAL | AL | Gas |
| AL | NAL | AL | NAL | AL | NAL | AL | NAL |
| NAL | Gas | NAL | Gas | NAL | Gas | NAL | Gas |
| NAL | Gas | NAL | Gas | NAL | Gas | NAL | AL |
| NAL | Gas | NAL | Gas | NAL | AL | NAL | Gas |
| NAL | Gas | NAL | Gas | NAL | AL | NAL | AL |
| NAL | Gas | NAL | AL | NAL | Gas | NAL | Gas |
| NAL | Gas | NAL | AL | NAL | Gas | NAL | AL |
| NAL | Gas | NAL | AL | NAL | AL | NAL | Gas |
| NAL | Gas | NAL | AL | NAL | AL | NAL | AL |
| NAL | AL | NAL | Gas | NAL | Gas | NAL | Gas |

TABLE 3-continued

Fluids Employed in Exemplary Co-injection Workflows

| Priming fluid | Displacement Fluid | First Fluid of a First Co-Injection | Second Fluid of a First Co-Injection | First Fluid of a Second Co-Injection | Second Fluid of a Second Co-Injection | First Fluid of a Third Co-Injection | Second Fluid of a Third Co-Injection |
|---|---|---|---|---|---|---|---|
| NAL | AL | NAL | Gas | NAL | Gas | NAL | AL |
| NAL | AL | NAL | Gas | NAL | AL | NAL | Gas |
| NAL | AL | NAL | Gas | NAL | AL | NAL | AL |
| NAL | AL | NAL | AL | NAL | Gas | NAL | Gas |
| NAL | AL | NAL | AL | NAL | Gas | NAL | AL |
| NAL | AL | NAL | AL | NAL | AL | NAL | Gas |
| NAL | AL | NAL | AL | NAL | AL | NAL | AL |

AL: Aqueous Liquid;
NAL: Non-aqueous Liquid

TABLE 4

Fluids Employed in Exemplary Co-injection Workflows

| Priming fluid | Displacement Fluid | First Fluid of a First Co-Injection | Second Fluid of a First Co-Injection | First Fluid of a Second Co-Injection | Second Fluid of a second Co-Injection | First Fluid of a Third Co-Injection | Second Fluid of a Third Co-Injection | First Fluid of a Fourth Co-Injection | Second Fluid of a Fourth Co-Injection |
|---|---|---|---|---|---|---|---|---|---|
| AL | Gas | AL | Gas | AL | Gas | AL | Gas | AL | Gas |
| AL | Gas | AL | Gas | AL | Gas | AL | Gas | AL | NAL |
| AL | Gas | AL | Gas | AL | Gas | AL | NAL | AL | Gas |
| AL | Gas | AL | Gas | AL | Gas | AL | NAL | AL | NAL |
| AL | Gas | AL | Gas | AL | NAL | AL | Gas | AL | Gas |
| AL | Gas | AL | Gas | AL | NAL | AL | Gas | AL | NAL |
| AL | Gas | AL | Gas | AL | NAL | AL | NAL | AL | Gas |
| AL | Gas | AL | Gas | AL | NAL | AL | NAL | AL | NAL |
| AL | Gas | AL | NAL | AL | Gas | AL | Gas | AL | Gas |
| AL | Gas | AL | NAL | AL | Gas | AL | Gas | AL | NAL |
| AL | Gas | AL | NAL | AL | Gas | AL | NAL | AL | Gas |
| AL | Gas | AL | NAL | AL | Gas | AL | NAL | AL | NAL |
| AL | Gas | AL | NAL | AL | NAL | AL | Gas | AL | Gas |
| AL | Gas | AL | NAL | AL | NAL | AL | Gas | AL | NAL |
| AL | Gas | AL | NAL | AL | NAL | AL | NAL | AL | Gas |
| AL | Gas | AL | NAL | AL | NAL | AL | NAL | AL | NAL |
| AL | NAL | AL | Gas | AL | Gas | AL | Gas | AL | Gas |
| AL | NAL | AL | Gas | AL | Gas | AL | Gas | AL | NAL |
| AL | NAL | AL | Gas | AL | Gas | AL | NAL | AL | Gas |
| AL | NAL | AL | Gas | AL | Gas | AL | NAL | AL | NAL |
| AL | NAL | AL | Gas | AL | NAL | AL | Gas | AL | Gas |
| AL | NAL | AL | Gas | AL | NAL | AL | Gas | AL | NAL |
| AL | NAL | AL | Gas | AL | NAL | AL | NAL | AL | Gas |
| AL | NAL | AL | Gas | AL | NAL | AL | NAL | AL | NAL |
| AL | NAL | AL | NAL | AL | Gas | AL | Gas | AL | Gas |
| AL | NAL | AL | NAL | AL | Gas | AL | Gas | AL | NAL |
| AL | NAL | AL | NAL | AL | Gas | AL | NAL | AL | Gas |
| AL | NAL | AL | NAL | AL | Gas | AL | NAL | AL | NAL |
| AL | NAL | AL | NAL | AL | NAL | AL | Gas | AL | Gas |
| AL | NAL | AL | NAL | AL | NAL | AL | Gas | AL | NAL |
| AL | NAL | AL | NAL | AL | NAL | AL | NAL | AL | Gas |
| AL | NAL | AL | NAL | AL | NAL | AL | NAL | AL | NAL |
| NAL | Gas | NAL | Gas | NAL | Gas | NAL | Gas | NAL | Gas |
| NAL | Gas | NAL | Gas | NAL | Gas | NAL | Gas | NAL | AL |
| NAL | Gas | NAL | Gas | NAL | Gas | NAL | AL | NAL | Gas |
| NAL | Gas | NAL | Gas | NAL | Gas | NAL | AL | NAL | AL |
| NAL | Gas | NAL | Gas | NAL | AL | NAL | Gas | NAL | Gas |
| NAL | Gas | NAL | Gas | NAL | AL | NAL | Gas | NAL | AL |
| NAL | Gas | NAL | Gas | NAL | AL | NAL | AL | NAL | Gas |
| NAL | Gas | NAL | Gas | NAL | AL | NAL | AL | NAL | AL |
| NAL | Gas | NAL | AL | NAL | Gas | NAL | Gas | NAL | Gas |
| NAL | Gas | NAL | AL | NAL | Gas | NAL | Gas | NAL | AL |
| NAL | Gas | NAL | AL | NAL | Gas | NAL | AL | NAL | Gas |
| NAL | Gas | NAL | AL | NAL | Gas | NAL | AL | NAL | AL |
| NAL | Gas | NAL | AL | NAL | AL | NAL | Gas | NAL | Gas |
| NAL | Gas | NAL | AL | NAL | AL | NAL | Gas | NAL | AL |
| NAL | Gas | NAL | AL | NAL | AL | NAL | AL | NAL | Gas |
| NAL | Gas | NAL | AL | NAL | AL | NAL | AL | NAL | AL |
| NAL | AL | NAL | Gas | NAL | Gas | NAL | Gas | NAL | Gas |

TABLE 4-continued

Fluids Employed in Exemplary Co-injection Workflows

| Priming fluid | Displacement Fluid | First Fluid of a First Co-Injection | Second Fluid of a First Co-Injection | First Fluid of a Second Co-Injection | Second Fluid of a second Co-Injection | First Fluid of a Third Co-Injection | Second Fluid of a Third Co-Injection | First Fluid of a Fourth Co-Injection | Second Fluid of a Fourth Co-Injection |
|---|---|---|---|---|---|---|---|---|---|
| NAL | AL | NAL | Gas | NAL | Gas | NAL | Gas | NAL | AL |
| NAL | AL | NAL | Gas | NAL | Gas | NAL | AL | NAL | Gas |
| NAL | AL | NAL | Gas | NAL | Gas | NAL | AL | NAL | AL |
| NAL | AL | NAL | Gas | NAL | AL | NAL | Gas | NAL | Gas |
| NAL | AL | NAL | Gas | NAL | AL | NAL | Gas | NAL | AL |
| NAL | AL | NAL | Gas | NAL | AL | NAL | AL | NAL | Gas |
| NAL | AL | NAL | Gas | NAL | AL | NAL | AL | NAL | AL |
| NAL | AL | NAL | AL | NAL | Gas | NAL | Gas | NAL | Gas |
| NAL | AL | NAL | AL | NAL | Gas | NAL | Gas | NAL | AL |
| NAL | AL | NAL | AL | NAL | Gas | NAL | AL | NAL | Gas |
| NAL | AL | NAL | AL | NAL | Gas | NAL | AL | NAL | AL |
| NAL | AL | NAL | AL | NAL | AL | NAL | Gas | NAL | Gas |
| NAL | AL | NAL | AL | NAL | AL | NAL | Gas | NAL | AL |
| NAL | AL | NAL | AL | NAL | AL | NAL | AL | NAL | Gas |
| NAL | AL | NAL | AL | NAL | AL | NAL | AL | NAL | AL |

AL: Aqueous Liquid;
NAL: Non-aqueous Liquid

Introducing One or More Components.

There are provided, in some embodiments, methods for introducing one or more components. In some embodiments, the method comprises: (a) introducing a first fluid into a fluidic channel comprising a ceiling, a first sidewall, and a bottom, wherein the bottom of the fluidic channel comprises a plurality of microwells, and wherein the ceiling, the first sidewall, and the bottom of the fluidic channel surround a fluidic channel volume of the fluidic channel, whereby the fluidic channel volume and each microwell of the plurality of microwells comprise the first fluid; (b) introducing a first displacement fluid into the fluidic channel to displace the first fluid from the fluidic channel volume at a first flow rate; (c) introducing a second fluid, immediately followed by and/or simultaneously with, a second displacement fluid, into the fluidic channel at a second flow rate, wherein one or more components of the second fluid enters the content in the microwell when the second fluid comes into contact with the content in the microwell for a first duration, and wherein the second displacement fluid displaces the second fluid from the fluidic channel volume and/or seals the content of the microwell.

The method can comprise (c) introducing a third fluid, immediately followed by and/or simultaneously with a third displacement fluid, into the fluidic channel at a third flow rate, wherein one or more components of the third fluid enters the content in the microwell when the third fluid comes into contact with the content in the microwell for a second duration, and wherein the third displacement fluid displaces the third fluid from the fluidic channel volume and/or seals the content of the microwell.

There are provided, in some embodiments, methods for introducing one or more components. Disclosed herein include methods for introducing one or more components. In some embodiments, the method comprises: (a) introducing a first fluid into a fluidic channel comprising a ceiling, a first sidewall, and a bottom, wherein the bottom of the fluidic channel comprises a plurality of microwells, and wherein the ceiling, the first sidewall, and the bottom of the fluidic channel surround a fluidic channel volume of the fluidic channel, whereby the fluidic channel volume and each microwell of the plurality of microwells comprise the first fluid; (b) introducing a first displacement fluid into the fluidic channel to displace the first fluid from the fluidic channel volume; (c) introducing a plurality of second fluids, each immediately followed by and/or simultaneously with a second displacement fluid, into the fluidic channel at a second flow rate, wherein one or more components of each of the plurality of second fluids enters the content in the microwell when the second fluid comes into contact with the content in the microwell for a first duration, and wherein the second displacement fluid displaces the second fluid from the fluidic channel volume and/or seals the content of the microwell.

There are provided, in some embodiments, methods for introducing one or more components. Disclosed herein include methods for introducing one or more components. In some embodiments, the method comprises: (a) providing a fluidic channel comprising a ceiling, a first sidewall, and a bottom, wherein the bottom of the fluidic channel comprises a plurality of microwells comprising a first fluid, wherein the ceiling, the first sidewall, and the bottom of the fluidic channel surround a fluidic channel volume of the fluidic channel, and wherein the fluidic channel volume lacks the first fluid; (b) introducing a plurality of second fluids, each immediately followed by and/or simultaneously with a second displacement fluid, into the fluidic channel at a second flow rate, wherein one or more components of each of the plurality of second fluids enters the content in the microwell when the second fluid comes into contact with the content in the microwell for a first duration, and wherein the second displacement fluid displaces the second fluid from the fluidic channel volume and/or seals the content of the microwell.

Providing the fluidic channel can comprise: introducing the first fluid into the fluidic channel, whereby the fluidic channel volume and each microwell of the plurality of microwells comprise the first fluid; and (b) introducing a first displacement fluid into the fluidic channel to displace the first fluid from the fluidic channel volume. In some embodiments, the method comprises introducing a third displacement fluid immediately prior to introducing a second fluid of the plurality of second fluids. The method can comprise introducing a third displacement fluid immediately after introducing the second displacement fluid. In some embodiments, the method comprises introducing a third displacement fluid immediately prior to introducing the second displacement fluid. The method can comprise introducing a third fluid immediately prior to introducing a second fluid of the plurality of second fluids. In some embodiments, the method comprises introducing a third fluid immediately after introducing the second displacement fluid while in other embodiments a third fluid is introduced immediately prior to introducing the second displacement fluid.

In some embodiments, the first fluid is a first plug and the second fluid is a second plug. The first fluid, second fluid, third fluid, fourth fluid, fifth fluid, sixth fluid, seventh fluid, priming fluid, first displacement fluid, second displacement fluid, third displacement fluid, and/or fourth displacement fluid can be a plug.

The second fluid and/or the third fluid can enter the content of the microwell by diffusion. In some embodiments, the concentrations of the one or more components of the second fluid in the content of the microwell is related to the first duration of the contact, and/or the concentrations of the one or more components of the third fluid in the content of the microwell is related to the second duration of the contact. In some embodiments, the first duration of the contact is related to the first speed of the second fluid in the flow channel and the volume of the second fluid, and/or the second duration of the contact is related to the second speed of the third fluid in the flow channel and the volume of the third fluid. The first duration of the contact can depend on the first speed of the second fluid in the flow channel and the longitudinal length of the second fluid in the flow channel, and/or the second duration of the contact depends on the second speed of the third fluid in the flow channel and the longitudinal length of the third fluid in the flow channel.

The longitudinal length of the second fluid in the flow channel can depend on the volume of the second fluid introduced, the volume of the fluidic channel volume, the volume of the flowcell, or a combination thereof, and/or the longitudinal length of the third fluid in the flow channel depends on the volume of the third fluid introduced, the volume of the fluidic channel volume, the volume of the flowcell, or a combination thereof. In some embodiments, the first flow rate is a fixed flow rate, the second flow rate is a fixed flow rate, and/or the third flow rate is a fixed flow rate. In some embodiments, the first flow rate is a variable flow rate, the second flow rate is a variable flow rate, and/or the third flow rate is a variable flow rate. In some embodiments, the first flow rate is an increasing flow rate, the second flow rate is an increasing flow rate, and/or the third flow rate is an increasing flow rate. In some embodiments, the first flow rate is a decreasing flow rate, the second flow rate is a decreasing flow rate, and/or the third flow rate is a decreasing flow rate.

Introducing the first fluid and/or the first displacement fluid can comprise co-injecting the first fluid immediately followed by and/or simultaneously with the first displacement fluid at the first flow rate. Introducing the first fluid and/or the first displacement fluid can comprise introducing the first fluid and/or the first displacement fluid using a pump. In some embodiments, introducing the second fluid, immediately followed by and/or simultaneously with the second displacement fluid, into the fluidic channel comprises co-injecting the second fluid followed by the second displacement fluid. Introducing the second fluid, immediately followed by and/or simultaneously with the third displacement fluid, can comprise introducing the third fluid, immediately followed by and/or simultaneously with the third fluid using a pump. In some embodiments, introducing the third fluid, immediately followed by and/or simultaneously with the third displacement fluid, into the fluidic channel comprises co-injecting the third fluid followed by the third displacement fluid. In some embodiments, introducing the third fluid, immediately followed by and/or simultaneously with the third displacement fluid, comprises introducing the third fluid, immediately followed by and/or simultaneously with the third fluid using a pump.

The first fluid and/or the first displacement fluid can be introduced into the fluidic channel via non-laminar flow, the second fluid and/or the second displacement fluid can be introduced into the fluidic channel via non-laminar flow, and/or the third fluid and/or the third displacement fluid can be introduced into the fluidic channel via non-laminar flow. In some embodiments, the fluidic channel is configured for introducing the first fluid, the first displacement fluid, the second fluid, the second displacement fluid, the third fluid, and/or the third displacement fluid via non-laminar flow. In some embodiments, the non-laminar flow can be plug flow or is approximately plug flow.

The first fluid can be introduced into the fluidic channel via a first opening of a flowcell comprising the fluidic channel, and the first fluid is displaced from the fluidic channel volume via a second opening of the flowcell. The second fluid can be introduced into the fluidic channel via a first opening of a flowcell comprising the fluidic channel, and the second fluid is displaced from the fluidic channel volume via a second opening of the flowcell. In some embodiments, the third fluid is introduced into the fluidic channel via a first opening of a flowcell comprising the fluidic channel, and the third fluid is displaced from the fluidic channel volume via a second opening of the flowcell. The third fluid can be introduced into the fluidic channel via a second opening of a flowcell comprising the fluidic channel, and the third fluid is displaced from the fluidic channel volume via a first opening of the flowcell. In some embodiments, the third fluid is introduced into the fluidic channel via a third opening of a flowcell comprising the fluidic channel, and the third fluid is displaced from the fluidic channel volume via a fourth opening of the flowcell.

The method can comprise re-orienting the direction of the fluidic channel relative to the bottom of the fluidic channel prior to introducing the third fluid. The method can comprise re-orienting the direction of the fluidic channel relative to the bottom of the fluidic channel by 80, 180, or 270 degrees. The microwell, after introducing the first displacement fluid, can comprise a single cell, a particle, or a combination thereof. The first fluid can comprise an aqueous liquid, a plurality of single cells, a plurality of particles, or a combination thereof. The aqueous liquid can comprise a priming liquid. In some embodiments, the first displacement fluid, the second displacement fluid comprise, and/or the third displacement fluid comprises a gas, a non-aqueous liquid, or a combination thereof. The second fluid and/or the third fluid can comprise an aqueous liquid. The first content liquid, the second content liquid, and/or the third content liquid can comprise a non-aqueous liquid. The first displacement liquid, the second displacement liquid, and/or the third displacement liquid can comprise a gas, an aqueous liquid, or a combination thereof.

In some embodiments, the density of the first content liquid is higher than the density of the second content liquid, wherein the density of the second content liquid is higher than the density of the third content liquid, and/or wherein the density of the first content liquid is higher than the density of the third content liquid. In some embodiments, the density of the first content liquid is higher than the density of the first displacement liquid, the density of the second displacement liquid, and/or the density of the third displacement liquid. In some embodiments, the density of the second content liquid is higher than the density of the first displacement liquid, the density of the second displacement liquid, and/or the density of the third displacement liquid. In some embodiments, the density of the third content liquid is higher than the density of the first displacement liquid, the density of the second displacement liquid, and/or the density of the third displacement liquid. In some embodiments, the density of the first content liquid is lower than the density of the first displacement liquid, the density of the second displacement liquid, and/or the density of the third displacement liquid. In some embodiments, the density of the second content liquid is lower than the density of the first displacement liquid, the density of the second displacement liquid, and/or the density of the third displacement liquid. In some embodiments, the density of the third content liquid is lower than the density of the first displacement liquid, the density of the second displacement liquid, and/or the density of the third displacement liquid. The difference in density between two co-injected fluids provided herein (e.g., a second fluid and a second displacement fluid) can be, be about, be greater than, or be at most 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, 2×, 3×, 4×, 5×, 6×, 7×, 8×, 9×, 10×, or higher and overlapping ranges therein).

In some embodiments, the first displacement fluid, the second displacement fluid, and/or the third displacement fluid are different. In some embodiments, the first displacement fluid, the second displacement fluid, and/or the third displacement fluid are different types. In some embodiments, the first displacement fluid, the second displacement fluid, and/or the third displacement fluid are identical. In some embodiments, the first displacement fluid, the second displacement fluid, and/or the third displacement fluid are of the same type. In some embodiments, the first fluid, the second fluid, and/or the third fluid are different. In some embodiments, the first fluid, the second fluid, and/or the third fluid are different types. In some embodiments, the first fluid, the second fluid, and/or the third fluid are identical. In some embodiments, the first fluid, the second fluid, and/or the third fluid are of the same type. In some embodiments, the first fluid, the second fluid, and/or the third fluid comprise an analyte, a buffer component, a small molecule, a biomolecule, a reagent, an agent, or a combination thereof.

The first fluid, the second fluid, and/or the third fluid can comprise a lysis buffer. Upon exposure to the lysis buffer, the content of the cell can be released into the microwell. Target molecules associated with the cell can hybridize to target binding regions of barcodes associated with the particle. In some embodiments, the method comprises performing a reaction. (e.g., a reverse transcription reaction, a nucleic acid extension reaction, polymerase chain reaction, and/or a combination thereof).

Determining the Number of Occurrences of a Target Nucleic Acid Molecule in Single Cells Disclosed herein include methods for determining the number of occurrences of a target nucleic acid molecule in single cells. The compositions and methods provided herein can be used with any single cell workflow. Single cell workflows can utilize microwell arrays or microwell cartridges (e.g., BD Resolve™) or microfluidics devices (e.g., 10× Genomics (San Francisco, CA), Drop-seq (McCarroll Lab, Harvard Medical School (Cambridge, Massachusett); Macosko et al., Cell, 2015 May 21 16; 5:1202), or Abseq (Mission Bio (San Francisco, CA); Shahi et al., Sci Rep. 2017 Mar. 14; 7:44447) in combination with solid or semi-solid particles associated with stochastic barcodes (e.g., BD Resolve, or Drop-seq) or disruptable hydrogel particles enclosing releasable stochastic barcodes (e.g., 10× Genomics, or Abseq).

In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; (b) capturing single cells and single beads in the plurality of microwells, wherein a single bead comprises a plurality of tethered barcodes, and wherein the plurality of tethered barcodes further comprises: i) a bead-specific cellular label; ii) a diverse set of molecular labels; and/or iii) a plurality of target binding regions capable of hybridizing with target nucleic acid molecules; (c) co-injecting a first fluid and a second fluid into the fluidic channel, wherein the first fluid is introduced into the fluidic channel immediately before the second fluid, wherein the first fluid interfaces with a surface of the content of the microwell for a duration, wherein the first fluid comprises a lysis buffer, wherein one or more components of the first fluid enter the microwell by diffusion and initiate cellular lysis, and wherein the second fluid seals the content of the microwell. The method can comprise (d) hybridizing target nucleic acid molecules released from single cells following cellular lysis with the plurality of target binding regions tethered to single beads in a stochastic manner. The method can comprise (e) performing an extension reaction to create a plurality of molecular conjugates each comprising a barcode and a portion of a complementary sequence of one of the target nucleic acid molecule. The method can comprise (f) amplifying and sequencing the molecular conjugates. The method can comprise (g) determining the number of occurrences of the target nucleic acid molecule in the single cells.

Figure 9:
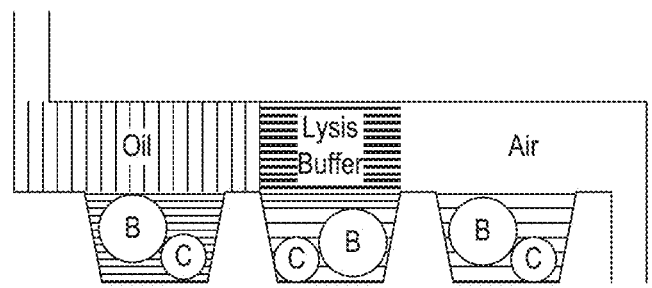
FIG. 9 provides a schematic illustration of an exemplary flowcell undergoing a co-injection of a first fluid comprising a lysis buffer and a second fluid comprising an oil.

FIG. 9 provides a schematic illustration of an exemplary flowcell undergoing a co-injection of a first fluid comprising a lysis buffer (e.g., CHAPS lysis buffer) and a second fluid comprising an oil (e.g., GC oil). The methods disclosed herein can be used improve the performance of BD Rhapsody™ (or other single cell assays) through a reduction in cross-talk of molecules between microwells. Cells and beads can be loaded into the microwell array as described herein. The co-injection method can enable precise control the lysis conditions to reduce inter-well molecular cross-talk. For example, cells and beads can be loaded to microwells as described herein such that each cell is paired with a single bead. Following cell and bead loading, cells can be lysed and contents of the cells diffuse freely into the buffer in the microwell. The BD Rhapsody™ assay (or other single cell assays) can be used to capture RNA or proteins from each cell on the beads. Co-injecting a lysis buffer and an oil can help avoid contamination of proteins or RNA between microwells. Control over the duration in which lysis buffer interfaces with microwells can allow optimization to control diffusion time of lysis buffer from the bulk lysis buffer into the microwell such that lysis buffer concentration is sufficient to lyse cells. Additionally or alternatively, the interface duration can be short enough such that cell contents do not diffuse out of the microwell following cell lysis. The exact duration over which lysis buffer interacts with each microwell can be precisely controlled and/or pre-determined. After oil flows over the microwell, phase separation between aqueous buffer and oil seals and contains the cellular contents inside the microwell. In some embodiments, the interface duration is determined by the lysis buffer volume and the flow rate of the lysis buffer. The timing for exposure of lysis buffer to the microwell contents can matche diffusion time of lysis buffer from the bulk lysis solution to microwells.

The bottom of the fluidic channel is shown comprising a substrate which comprises a plurality of microwells. Prior to the co-injection, the volume or space of the fluidic channel (excluding the microwells) comprises air and the microwells comprise a single bead ("B"), a single cell ("C"). A first fluid comprising a lysis buffer and a second fluid comprising an oil are co-injected into the fluidic channel, with the first fluid of the co-injection introduced into the fluidic channel immediately before the second fluid of the co-injection. The microwell immediately adjacent to the inlet has been passed by the first fluid of the co-injection and now contains comprises a sufficient amount of lysis buffer components to lyse the single cell. The second fluid of the co-injection is depicted sealing the content the microwell immediately adjacent to the inlet. The first fluid of the co-injection is shown interfacing with a surface of the content of the microwell located in the middle of the fluidic channel, where one or more components of the lysis are in the process of entering the content of the microwell. The microwell adjacent to the outlet has not yet been reached by the first fluid of the co-injection.

In some embodiments, the density of the first fluid is greater than the density of the second fluid, and the first fluid and the second fluid are immiscible. In some embodiments, the first fluid is a first plug and the second fluid is a second plug. Step (b) can comprise priming the flow cell, loading the cells, and then loading the beads. In some embodiments, step (b) can comprise priming the flow cell, displacing the priming buffer with an air injection, loading a cell suspension, displacing the cell suspension with an air injection, and loading the beads. The plurality of tethered barcodes further can comprise a universal primer sequence. The plurality of target binding regions of the plurality of barcodes can be tethered to a bead comprise a mixture of sequences selected from the group consisting of gene-specific sequences, oligo-dT sequences, random multimer sequences, or any combination thereof. The target nucleic acid molecules can comprise RNA molecules (e.g., mRNA molecules). The target nucleic acid molecules can comprise cellular component-binding reagent oligonucleotides (e.g., sample indexing oligonucleotides, cellular component-binding reagent oligonucleotides). In some embodiments, the target nucleic acid molecules comprise cellular component-binding reagent oligonucleotides, and determining the number of occurrences of the target nucleic acid molecule in the single cells indicates the number of copies of a cellular component target in the single cell. In some embodiments, the target nucleic acid molecules comprise sample indexing oligonucleotides, and determining the number of occurrences of the target nucleic acid molecule in the single cells indicates identifies the sample origin of the cell.

In some embodiments, the second fluid sealing the content of the microwell yields an increase in the number of mRNAs and/or cellular component-binding reagent oligonucleotides captured by the barcodes as compared to comparable flowcell methods performed using a single fluid injection. The second fluid sealing the content of the microwell can increase in the number of mRNAs and/or cellular component-binding reagent oligonucleotides captured by the barcodes by, by about, by at most about, or at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to comparable flowcell methods performed using a single fluid injection.

In some embodiments, the second fluid sealing the content of the microwell yields an increase in the number of occurrences of unique molecular labels associated with each of the mRNAs and/or cellular component-binding reagent oligonucleotides determined as compared to comparable flowcell methods performed using a single fluid injection. The second fluid sealing the content of the microwell can increase the number of occurrences of unique molecular labels associated with each of the mRNAs and/or cellular component-binding reagent oligonucleotides determined by, by about, by at most about, or at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to comparable flowcell methods performed using a single fluid injection.

In some embodiments, the second fluid sealing the content of the microwell yields an increase in the signal-to-noise ratio as compared to comparable flowcell methods performed using a single fluid injection. The second fluid sealing the content of the microwell can increase in the signal-to-noise ratio by, by about, by at most about, or at least about 2% (e.g., 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 75%, 100%, or higher and overlapping ranges therein) as compared to comparable flowcell methods performed using a single fluid injection.

Methods of Measuring the Dose-dependent Phenotypic Effects of an Agent on Single Cells There are provided, in some embodiments, methods of measuring the dose-dependent phenotypic effects of an agent on single cells. In some embodiments, the method comprises: (a) providing a flowcell comprising a fluidic channel, wherein the fluidic channel comprises a ceiling, a first sidewall, and a bottom, and wherein the bottom comprises a substrate which comprises a plurality of microwells; (b) capturing single cells in the plurality of microwells; (c) co-injecting a first fluid and a second fluid into the fluidic channel, wherein the first fluid is introduced into the fluidic channel immediately before the second fluid, wherein the first fluid interfaces with a surface of the content of the microwell for a duration, wherein the first fluid comprises one or more components, wherein the one or more components of the first fluid comprise an agent, wherein the flow rate of the first fluid is not uniform along the longitudinal path of the fluidic channel, wherein the agent enters the microwell by diffusion during the duration, wherein the final concentration of the agent in the content of the microwell is unequal for at least two microwells of the plurality of microwells, and wherein the second fluid seals the content of the microwell; and (d) measuring one or more phenotypic effects dependent on the final concentration of the agent in the microwell.

In some embodiments, the density of the first fluid is greater than the density of the second fluid and/or the first fluid and the second fluid are immiscible. The method can comprise a second co-injecting of fluids. The second co-injecting can comprises co-injecting a second first liquid of a second co-injection and a second liquid of a second co-injection into the fluidic channel, wherein the first liquid of the second co-injection is introduced into the fluidic channel immediately before the second liquid of the second co-injection. The second liquid of the second co-injection can seal the content of the microwell. In some embodiments, the density of the first liquid of the second co-injection is greater than the density of second liquid of the second co-injection, and wherein the first liquid of the second co-injection and the second liquid of the second co-injection are immiscible. The second co-injecting can be performed in the reverse direction or same direction relative to the first co-injecting. In some embodiments, the first fluid of the second co-injection can comprises a second agent. The method can comprise 3, 4, 5, 6, 7, 8, 9, or more co-injections of fluids as disclosed herein, and one or more of the first fluids of said co-injections can comprise 3, 4, 5, 6, 7, 8, 9, or more additional agents. In some embodiments, the first fluid is a first plug and the second fluid is a second plug. The flow rate of the first fluid can be higher at an anterior position along the longitudinal path of the fluidic channel relative a posterior position along the longitudinal path of the fluidic channel and/or the flow rate of the first fluid can be lower at an anterior position along the longitudinal path of the fluidic channel relative a posterior position along the longitudinal path of the fluidic channel. In some embodiments, the difference between the flow rate of the first fluid at an anterior position along the longitudinal path of the fluidic channel relative a posterior position along the longitudinal path of the fluidic channel is, is about, is at most about, or is at least about 1.1-fold. In some embodiments, the ratio of the flow rate of the first fluid at an anterior position along the longitudinal path of the fluidic channel relative the flow rate at a posterior position along the longitudinal path of the fluidic channel ranges from 1:100 to 100:1. In some embodiments, the ratio of the two flow rates is at most 10:1. In some embodiments, the ratio of the two flow rates is at most 100:1. In some embodiments, the ratio of the two flow rates is at most 1:1000. In some embodiments, the ratio of the two flow rates is at least 1:10. In some embodiments, the ratio of the two flow rates is at least 1:100. In some embodiments, the ratio of the two flow rates is at least 1:1000.

In some embodiments, the final concentration of the agent in the contents of the plurality of microwells following the serial the co-injecting is non-uniform. The final concentration of the agent in the content of each microwell can change along the longitudinal path of the fluidic channel. In some embodiments, the change in the final concentration of the agent in the content of each microwell can be linear, non-linear, exponential, and/or logarithmic. In some embodiments, the difference between the final concentration of the agent in the content of a microwell at an anterior position along the longitudinal path of the fluidic channel relative a posterior position along the longitudinal path of the fluidic channel is, is about, is at most about, or is at least about 1.1-fold. In some embodiments, the ratio of the final concentration of the agent in the content of a microwell at an anterior position along the longitudinal path of the fluidic channel relative a posterior position along the longitudinal path of the fluidic channel ranges from 1:100 to 100:1. In some embodiments, the ratio of the two final concentrations is at most 10:1. In some embodiments, the ratio of the two final concentrations is at most 100:1. In some embodiments, the ratio of the t two final concentrations is at most 1:1000. In some embodiments, the ratio of the two final concentrations is at least 1:10. In some embodiments, the ratio of the two final concentrations is at least 1:100. In some embodiments, the ratio of the two final concentrations is at least 1:1000.

The agent and/or a second agent can comprise one or more components. In some embodiments, the agent comprises one or more of a chemical agent, a pharmaceutical, small molecule, a biologic, a CRISPR single-guide RNA (sgRNA), a small interfering RNA (siRNA), CRISPR RNA (crRNA), a small hairpin RNA (shRNA), a microRNA (miRNA), a piwi-interacting RNA (piRNA), an antisense oligonucleotide, a peptide or peptidomimetic inhibitor, an aptamer, an antibody, an intrabody, or any combination thereof. In some embodiments, the agent can comprise one or more of an epigenetic modifying agent, epigenetic enzyme, a bicyclic peptide, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis inhibitor, a nuclease, a protein fragment or domain, a tag or marker, an antigen, an antibody or antibody fragment, a ligand or a receptor, a synthetic or analog peptide from a naturally-bioactive peptide, an anti-microbial peptide, a pore-forming peptide, a targeting or cytotoxic peptide, a degradation or self-destruction peptide, a CRISPR component system or component thereof, DNA, RNA, artificial nucleic acids, a nanoparticle, an oligonucleotide aptamer, a peptide aptamer, or any combination thereof. The agent can possesses at least one effector activity selected from the group consisting of: modulating a biological activity, binding a regulatory protein, modulating enzymatic activity, modulating substrate binding, modulating receptor activation, modulating protein stability/degradation, modulating transcript stability/degradation, and any combination thereof.

In some embodiments, the agent can comprise an infectious agent, an anti-infectious agent, or a mixture of an infectious agent and an anti-infectious agent. An infectious agent can comprise a virus, a bacterium, a fungus, a protozoal parasite, or any combination thereof. An anti-infectious agent can comprise an anti-bacterial agent, an anti-fungal agent, an anti-parasitic agent, an anti-viral agent, or any combination thereof. In some embodiments, the agent can comprise a cytotoxic agent, such as, for example, a chemotherapeutic agent, a biologic agent, a toxin, a radioactive isotope, or any combination thereof. The agent can comprise a non-active component of a therapeutic, such as, for example, an excipient, carrier, diluent, vehicle, adjuvant, empty vector, or any combination thereof.

In some embodiments, the agent can comprise an expression vector, wherein the expression vector encodes one or more of the following: an mRNA, an antisense nucleic acid molecule, a RNAi molecule, a shRNA, a mature miRNA, a pre-miRNA, a pri-miRNA, an anti-miRNA, a ribozyme, any combination thereof. The single cells can comprise a recombinant expression vector. The recombinant expression vector can comprise an inducible promoter, wherein the expression of one or more of the following are under the control of said inducible promoter: an mRNA, an antisense nucleic acid molecule, a RNAi molecule, a shRNA, a mature miRNA, a pre-miRNA, a pri-miRNA, an anti-miRNA, a ribozyme, any combination thereof. The agent can comprise a dose-dependent inducer of the inducible promoter (e.g., tetracycline, pristinamycin, macrolide, ecdysone, mifepristone, or any combination thereof). In some embodiments, the agent modulates the expression and/or activity of one or more target biomarkers In some embodiments, the method can comprise capturing single beads in the plurality of microwells, wherein a single bead comprises a plurality of tethered barcodes, and wherein the plurality of tethered barcodes further comprises: i) a bead-specific cellular label; ii) a diverse set of molecular labels; and/or iii) a plurality of target binding regions capable of hybridizing with target nucleic acid molecules. Measuring one or more phenotypic effects dependent on the final concentration of the agent in the microwell can comprise mRNA expression profiling, wherein mRNA expression profiling comprises quantitative analysis of a plurality of mRNA targets in a cell. Measuring one or more phenotypic effects dependent on the final concentration of the agent in the microwell can comprise protein expression profiling, wherein protein expression profiling comprises quantitative analysis of a plurality of protein targets in a cell. Measuring one or more phenotypic effects dependent on the final concentration of the agent in the microwell can comprise simultaneous quantitative analysis of a plurality of protein targets and a plurality of nucleic acid target molecules in a cell.

Determination of the Longitudinal Flowcell Position of Cells and the Agent Exposure of Cells There are provided, in some embodiments, methods of determining of the longitudinal flowcell position of some or all cells within the microwell array. The determination of the longitudinal flowcell position of some or all cells within the microwell array can comprise determining the microwell of origin of some or all of the cells. Some or all of the microwells of the microwell array can comprise an array address code. The array address code can comprise a nucleic acid barcode unique for each microwell in the microwell array. In some embodiments, the array address code is covalently attached to one or more inner surfaces of the microwells. The covalent attachment can comprise the use of one or more cleavable linkers to enable release of the array address code. In some embodiments, the one or more cleavable linkers comprise acid-labile linkers, base-labile linkers, photocleavable linkers, enzyme-cleavable linkers, or any combination thereof. The array address code can comprise a restriction enzyme site. In some embodiments, a subset of the barcodes attached to the bead comprise an annealing site for the array address code. Upon release, the array address code can hybridize with the subset of the barcodes. In some embodiments, association of the cellular label and the array address code during sequencing identifies the microwell of origin of each cell within the microwell array.

In some embodiments, dual encoding schemes may be implemented by use of pre-deposited array address codes (e.g. nucleic acid barcodes that code for the location of a specific well in the array) instead of optically-encoded beads to implement dual encoding schemes. In some embodiments, array address codes may be deposited in wells using ink-jet printing techniques, microarray spotting techniques, dip-pen nanolithography techniques, and the like. In some embodiments, the array address codes may be non-specifically adsorbed to one or more inner surfaces of the microwells. In some embodiments, the array address codes may be covalently attached to one or more inner surfaces of the microwells. In some embodiments, the array address codes may be synthesized in situ by means of solid phase synthesis techniques, wherein one or more inner surfaces of the microwells are used as a solid support. In embodiments where the array address codes are covalently attached to one or more inner surfaces of the microwells, the attachment may comprise the use of cleavable linkers, e.g. acid-labile, base-labile, or photocleavable linkers, so that the array address codes may be released when desired and allowed to hybridize with a subset of the tethered stochastic labels attached to a bead. In some embodiments, the array address codes may be used in combination with the plurality of stochastic labels attached to a bead that comprises a cellular label. In some embodiments, the array address codes may be used instead of a plurality of stochastic labels attached to a bead, and may themselves comprise a cellular label, a molecular label, and one or more primer or adapter sequences.

There are provided, in some embodiments, methods of determining of the longitudinal flowcell position of some or all cells within the microwell array. Each of the plurality of beads can comprise a plurality of stochastic barcodes, a first group of optical labels, and a second group of optical labels. Each optical label in the first group of optical labels can comprise a first optical moiety and each optical label in the second group of optical labels can comprise a second optical moiety. Each of the plurality of beads is associated with an optical barcode comprising the first optical moiety and the second optical moiety, and wherein the first optical moiety and the second optical moiety are selected from a group comprising two or more spectrally-distinct optical moieties. At least two beads of the plurality of beads can comprise a unique optical barcode. The optical barcode of each of the plurality of beads can be detected in the flowcell to determine the location of each of the plurality of beads. The method can comprise detecting the optical barcode of each of the plurality of beads to determine the location of each of the plurality of beads. The method can comprise determining the microwell locations of the plurality of single cells based on the locations of the plurality of beads.

In some embodiments, methods and compositions are provided for use of optically-encoded beads in a dual encoding scheme, e.g. where individual beads are uniquely identified both by an optical code (e.g. by impregnating the beads with a spectrally-distinct set of fluorophores, quantum dots, Raman tags, up-converting phosphors, and the like; or by synthesis of an attached optical code through the use of solid-phase split-pool synthesis methodologies and a set of spectrally-distinct fluorescent building blocks) as well as a nucleic acid sequence (e.g. the cellular label) that is incorporated into the plurality of tethered stochastic labels attached to a given bead. Beads co-localized with cells exhibiting a set of predefined properties, or with more than one cell, would each be identified based on their optical code, and the sequence data arising from said beads would be subsequently identified by the corresponding cellular label sequence.

There are also provided, in some embodiments, methods of estimating the concentration of the agent at each longitudinal flowcell position (and thereby determining the agent exposure of each cell). In some embodiments, the first fluid comprises a fluorescent dye, wherein the proportion of the fluorescent dye to the agent is known. The flow cell can comprise a transparent window for optical imaging, and the method can comprise optical imaging of the flow cell after the co-injecting of the first fluid and the second fluid, wherein optical imaging comprises a measurement of the fluorescent dye in each microwell. The measurement of fluorescent dye in each microwell can enable the estimation of the concentration of the agent in each microwell. The method can further comprise deriving an estimation of a concentration of the agent each cell was exposed to based on the determination of the microwell of origin of each cell and the estimation of the concentration of the agent at each longitudinal flowcell position. The method can comprise correlation analysis of the estimated concentration of the agent each cell was exposed to and the RNA and/or DNA expression profiles of said cells. The correlation analysis can identifies one or more of the following: candidate therapeutic agents, candidate doses of candidate therapeutic agents, and cellular targets of candidate therapeutic agents.

EXAMPLES

Some aspects of the embodiments discussed above are disclosed in further detail in the following examples, which are not in any way intended to limit the scope of the present disclosure.

Example 1

Contained Cell Lysis Reaction

This example demonstrates the co-injection method can enable controlled lysis and physically sealing of microwell contents.

Calcein-stained cells distributed to microwells. A serial co-injection of a first fluid and a second fluid was performed according to the methods disclosed herein, using a first fluid comprising CHAPS lysis buffer and a second fluid comprising GC2 oil (BD CLiC library prep system). FIGS. 12A1-12C2 show exemplary bright-field images (FIGS. 12A1, 12B1, and 12C1) and fluorescent images (FIGS. 12A2, 12B2, and 12C2) of microwells 1 minute (FIGS. 12A1-12A2), 7 minutes (FIGS. 12B1-12B2), and 13 minutes (FIGS. 12C1-12C12) following a co-injection of a first fluid comprising CHAPS lysis buffer and a second fluid comprising GC2 oil.

FIGS. 12A1-12C2 show that the lysis buffer concentration in the microwells was sufficient to lyse cells. Calcein stained cells remained intact for up to 1 minute following seal with GC2 oil, and the cellular content was contained in the microwell with no clear loss of fluorescence (corresponds to no loss of calcein). This indicates that the GC2 oil seal hinders diffusion of calcein from the microwells out of the microwells. Given that the molecular weight of calcein is lower than most cellular molecules (e.g. mRNA, RNA, proteins, or DNA), the figures demonstrate that these larger molecules are also contained in the micro-wells.

Prior to the co-injection, three microwells of the array comprise a single calcein-stained cell. As seen in FIGS. 12A1-12A2, calcein-stained cells initially remained intact in the 1 minute following the seal with GC2 oil (with bright discrete points indicating calcein-stained cells were intact). As seen in FIGS. 12B1-12B2 and FIGS. 12C1-12C12, after 7 and 13 minutes respectively, the fluorescence became diffuse within the microwells of the calcein-stained cells, indicating cell lysis was successful. Further, the cellular content was contained in the microwell with no clear loss of fluorescence (corresponding to no loss of calcein). This indicates that the GC2 oil seal hinders diffusion of Calcein from the microwells to the volume or space of the fluidic channel (above the microwells). Given that the molecular weight of calcein is lower than most cellular molecules (e.g. mRNA, RNA, proteins, or DNA), the results demonstrate that these larger molecules are also contained in the microwells. Thus, the second fluid effectively sealed and contained the reaction within each microwell. Altogether, these data demonstrate the ability of a serial co-injection method provided herein to deliver reagents (e.g., lysis buffer reagents) to a microwell to initiate a reaction (e.g., cell lysis). Additionally, these data embody the unexpectedly prevention of molecular cross-talk between microwells that is achieved according to several embodiments.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for introducing one or more components to contents of microwells comprising:
   (a) introducing a first fluid into a fluidic channel comprising a ceiling, a first sidewall, and a bottom, wherein the bottom of the fluidic channel comprises a plurality of microwells, whereby the fluidic channel and each microwell of the plurality of microwells comprise the first fluid;
   (b) introducing a first displacement fluid into the fluidic channel to displace the first fluid from the fluidic channel at a first flow rate;
   (c) introducing a second fluid into the fluidic channel at a second flow rate while in contact with a second displacement fluid that is immiscible to the second fluid such that the second fluid is immediately followed by and in contact with the second displacement fluid and the second fluid and the second displacement fluid have the same flow rate,
   wherein one or more components of the second fluid enters the content in the microwell when the second fluid comes into contact with the content in the microwell for a first duration, and
   wherein the second displacement fluid displaces the second fluid from the fluidic channel and/or seals the content of the microwell.

2. The method of claim 1, comprising:
   (d) introducing a third fluid into the fluidic channel at a third flow rate while in contact with a third displacement fluid that is immiscible to the third fluid such that the third fluid is immediately followed by and in contact with the third displacement fluid and the third fluid and the third displacement fluid have the same flow rate,
   wherein one or more components of the third fluid enters the content in the microwell when the third fluid comes into contact with the content in the microwell for a second duration, and
   wherein the third displacement fluid displaces the third fluid from the fluidic channel and/or seals the content of the microwell.

3. The method of claim 1, comprising introducing a third displacement fluid immediately prior to introducing a second fluid of the plurality of second fluids.

4. The method of claim 1, comprising introducing a third displacement fluid immediately after introducing the second displacement fluid.

5. The method of claim 1, comprising introducing a third displacement fluid immediately prior to introducing the second displacement fluid.

6. The method of claim 1, comprising introducing a third fluid immediately prior to introducing a second fluid of the plurality of second fluids.

7. The method of claim 1, comprising introducing a third fluid immediately after introducing the second displacement fluid.

8. The method of claim 1, comprising introducing a third fluid immediately prior to introducing the second displacement fluid.

9. The method of claim 1, wherein the second fluid and/or the third fluid enters the content of the microwell by diffusion.

10. The method of claim 1, wherein the flow rate of the first fluid ranges from 0.001 ml/sec to 100 ml/sec.

11. The method of claim 10,
    wherein the fluidic channel further comprises an anterior position and a posterior position along a longitudinal path of the fluidic channel, the anterior position being located nearer to an inlet wherein the first fluid is introduced into the fluidic channel, and
    wherein the ratio of the flow rate of the first fluid at the anterior position relative the posterior position ranges from 1:1 to 1:10000.

12. The method of claim 10,
    wherein the first duration of the contact depends on the first speed of the second fluid in the flow channel and the longitudinal length of the second fluid in the flow channel, and/or
    wherein the second duration of the contact depends on the second speed of the third fluid in the flow channel and the longitudinal length of the third fluid in the flow channel.

13. The method of claim 12,
    wherein the longitudinal length of the second fluid in the flow channel depends on the volume of the second fluid introduced, the volume of the fluidic channel, the volume of the flowcell, or a combination thereof, and/or wherein the longitudinal length of the third fluid in the flow channel depends on the volume of the third fluid introduced, the volume of the fluidic channel, the volume of the flowcell, or a combination thereof.

14. The method of claim 1, wherein the first flow rate is a fixed flow rate, wherein the second flow rate is a fixed flow rate, and/or wherein the third flow rate is a fixed flow rate.

15. The method of claim 1, wherein the first flow rate is a variable flow rate, wherein the second flow rate is a variable flow rate, and/or wherein the third flow rate is a variable flow rate.

16. The method of claim 1, wherein the first flow rate is an increasing flow rate, wherein the second flow rate is an increasing flow rate, and/or the third flow rate is an increasing flow rate.

17. The method of claim 1, wherein the first flow rate is a decreasing flow rate, wherein the second flow rate is a decreasing flow rate, and/or wherein the third flow rate is a decreasing flow rate.

18. The method of claim 1, wherein the second fluid and the second displacement fluid are dispensed together into the fluidic channel from a container comprising both the second fluid and the second displacement fluid.

19. The method of claim 18, wherein the second fluid and the second displacement fluid are dispensed together into the fluidic channel from the container using a pump.

20. The method of claim 18, wherein the container is a pipette.

21. The method of claim 20, wherein the second fluid and the second displacement fluid are aspirated sequentially into the pipette prior to being dispensed together.

22. The method of claim 1, wherein the fluidic channel further comprises an inlet and an outlet, and wherein the second displacement fluid begins displacing the second fluid from the fluidic channel and/or sealing the contents of the microwell immediately adjacent to the inlet before the second fluid has reached the outlet.

* * * * *